US012740997B2

(12) United States Patent
Shimojo et al.

(10) Patent No.: US 12,740,997 B2
(45) Date of Patent: Sep. 22, 2026

(54) OLIGONUCLEOTIDE FOR INDUCING N-EXON SKIPPING DURING REST mRNA PRECURSOR PROCESSING

(71) Applicant: Osaka University, Osaka (JP)

(72) Inventors: Masahito Shimojo, Osaka (JP); Satoshi Obika, Osaka (JP); Keishiro Mishima, Osaka (JP); Misa Yoshida, Osaka (JP)

(73) Assignee: Osaka University, Osaka (JP)

( * ) Notice: Subject to any disclaimer, the term of this patent is extended or adjusted under 35 U.S.C. 154(b) by 509 days.

(21) Appl. No.: 18/547,071

(22) PCT Filed: Feb. 25, 2022

(86) PCT No.: PCT/JP2022/008079
§ 371 (c)(1),
(2) Date: Aug. 18, 2023

(87) PCT Pub. No.: WO2022/181807
PCT Pub. Date: Sep. 1, 2022

(65) Prior Publication Data

US 2024/0148775 A1 May 9, 2024

(30) Foreign Application Priority Data

Feb. 25, 2021 (JP) ................................ 2021-029327

(51) Int. Cl.
*C07H 21/02* (2006.01)
*A61K 31/713* (2006.01)
*A61P 35/00* (2006.01)
*C12N 15/113* (2010.01)

(52) U.S. Cl.
CPC ............ *A61K 31/713* (2013.01); *A61P 35/00* (2018.01); *C12N 15/113* (2013.01)

(58) Field of Classification Search
CPC .......................... C12N 15/113; C12N 2310/11
See application file for complete search history.

(56) References Cited

U.S. PATENT DOCUMENTS

| | | | |
|---|---|---|---|
| 2012/0059042 | A1 | 3/2012 | Platenburg et al. |
| 2012/0208991 | A1 | 8/2012 | Obika et al. |
| 2015/0266917 | A1 | 9/2015 | Obika et al. |
| 2017/0044528 | A1 | 2/2017 | Obika et al. |
| 2021/0277398 | A1 | 9/2021 | Shimojo |

FOREIGN PATENT DOCUMENTS

| | | | |
|---|---|---|---|
| JP | 2011520444 | A | 7/2011 |
| JP | 201443462 | A | 3/2014 |
| WO | 2011031998 | A1 | 3/2011 |
| WO | 2011052436 | A1 | 5/2011 |
| WO | 2014046212 | A1 | 3/2014 |
| WO | 2015012175 | A1 | 1/2015 |
| WO | 2015125783 | A1 | 8/2015 |
| WO | 2016089928 | A1 | 6/2016 |
| WO | 2018139679 | A1 | 8/2018 |
| WO | 2020027227 | A1 | 2/2020 |

OTHER PUBLICATIONS

Stein (The Journal of Clinical Investigation, 2001, 108, 5, 641-644).*

Bushra Raj et al., Molecular Cell, vol. 43, pp. 843-850, Sep. 2, 2011.

Cuilin Li et al., Molecular Medicine Reports, vol. 16, pp. 3707-3712, 2017.

PCT/JP2022/008079; PCT International Search Report of the International Searching Authority dated Apr. 12, 2022 and its English translation.

Chen, Guo-Lin et al. "Extensive Alternative Splicing of the Repressor Element Silencing Transcription Factor Linked to Cancer". PLoS ONE. Apr. 16, 2013. vol. 8. issue 4. e62217. pp. 1-11.

Ortuno-Pineda, Carlos et al. "Binding of hnRNP Hand U2AF65 to Respective G-codes and a Poly-Uridine Tract Collaborate in the N50-5'ss Selection of the Rest N Exon in H69 Cells". PLoS ONE. Jul. 5, 2012. vol. 7. issue 7. e40315. pp. 1-11.

Zhang, Donghong et al. "Non-CpG methylation by DNMT3B facilitates REST binding and gene silencing in developing mouse hearts". Nucleic Acids Research. Dec. 12, 2016. vol. 45. No. 6. pp. 3102-3115.

Conference Abstracts and Poster of 16th Annual Meeting of the Oligonucleotide Therapeutics Society (2020 Virtual Conference) Sep. 27-30, 2020 with the Poster, Abstract and the Annual Meeting homepage.

M. Kuwahara et al., Nucleic Acids Res., 2008, vol. 36, No. 13, pp. 4257-4265.

Tetrahedron Letters, 1981, vol. 22. pp. 1859-1862.

Nucleic Acids Research, Dec. 12, 2016, vol. 45, No. 6, p. 3102-3115.

Office Action for corresponding Japanese Patent Application No. 2023-502564 dated Dec. 9, 2025 and its English Machine Translation.

PLoS ONE, 2012 Date: Jul. 2005, vol. 7, Issue 7, 640315, p. 1-11.

PLoS ONE, Jan. 16, 2013, 04, vol. 8, Issue 4, e62217, p. 1-11.

* cited by examiner

*Primary Examiner* — Amy Rose Hudson

(74) *Attorney, Agent, or Firm* — Renner, Otto, Boisselle & Sklar, LLP

(57) ABSTRACT

An oligonucleotide or a pharmacologically acceptable salt thereof according to the present invention contains a nucleotide sequence complementary to a continuous sequence of at least 12 bases in a target region constituted by a base sequence of SEQ ID No. 1, and induces N-exon skipping in human REST pre-mRNA processing. Such oligonucleotides are useful for manufacturing medicines for treatment of cancer, for example.

9 Claims, 16 Drawing Sheets

Specification includes a Sequence Listing.

[Fig. 1]
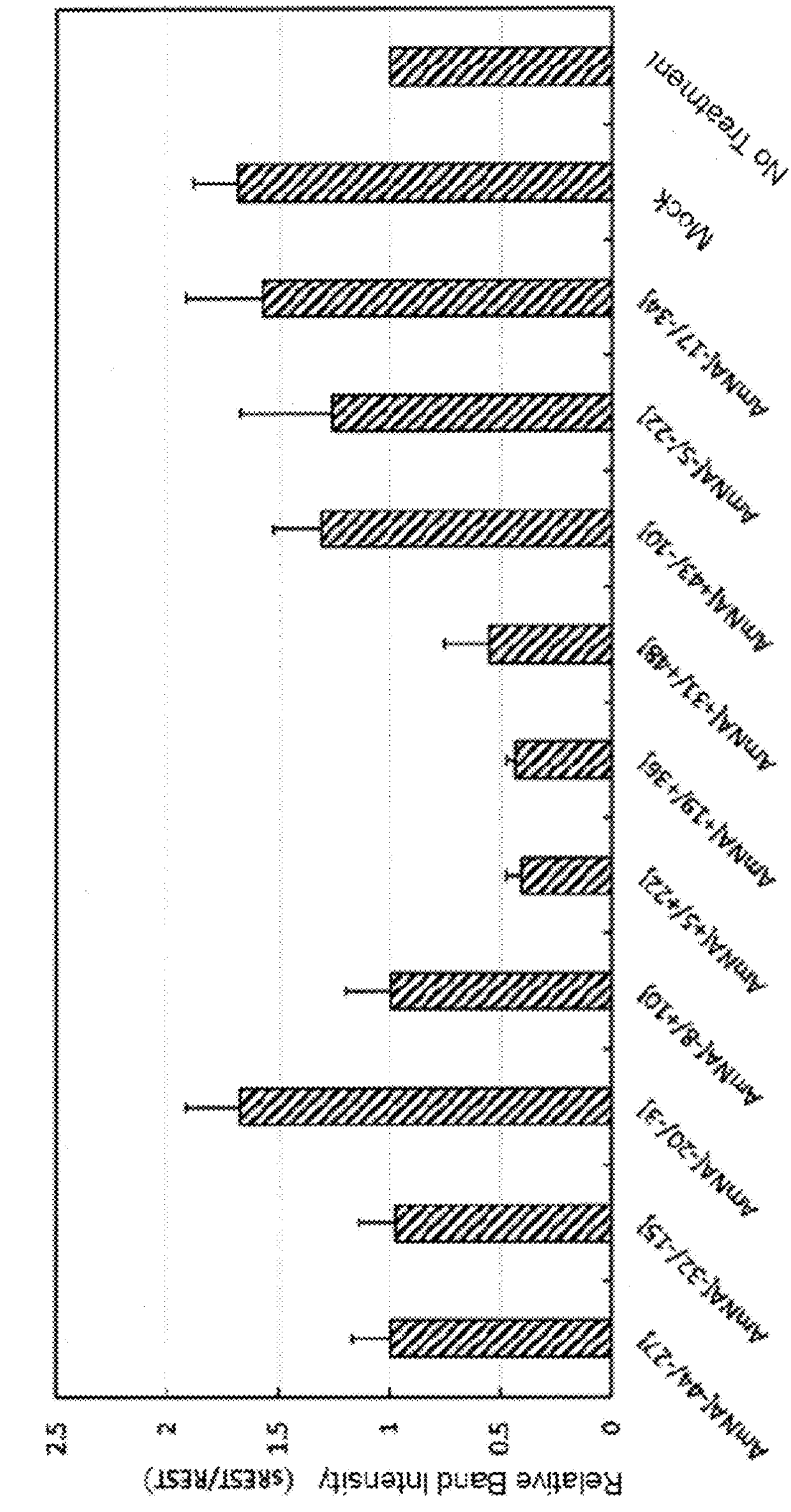

[Fig. 2]
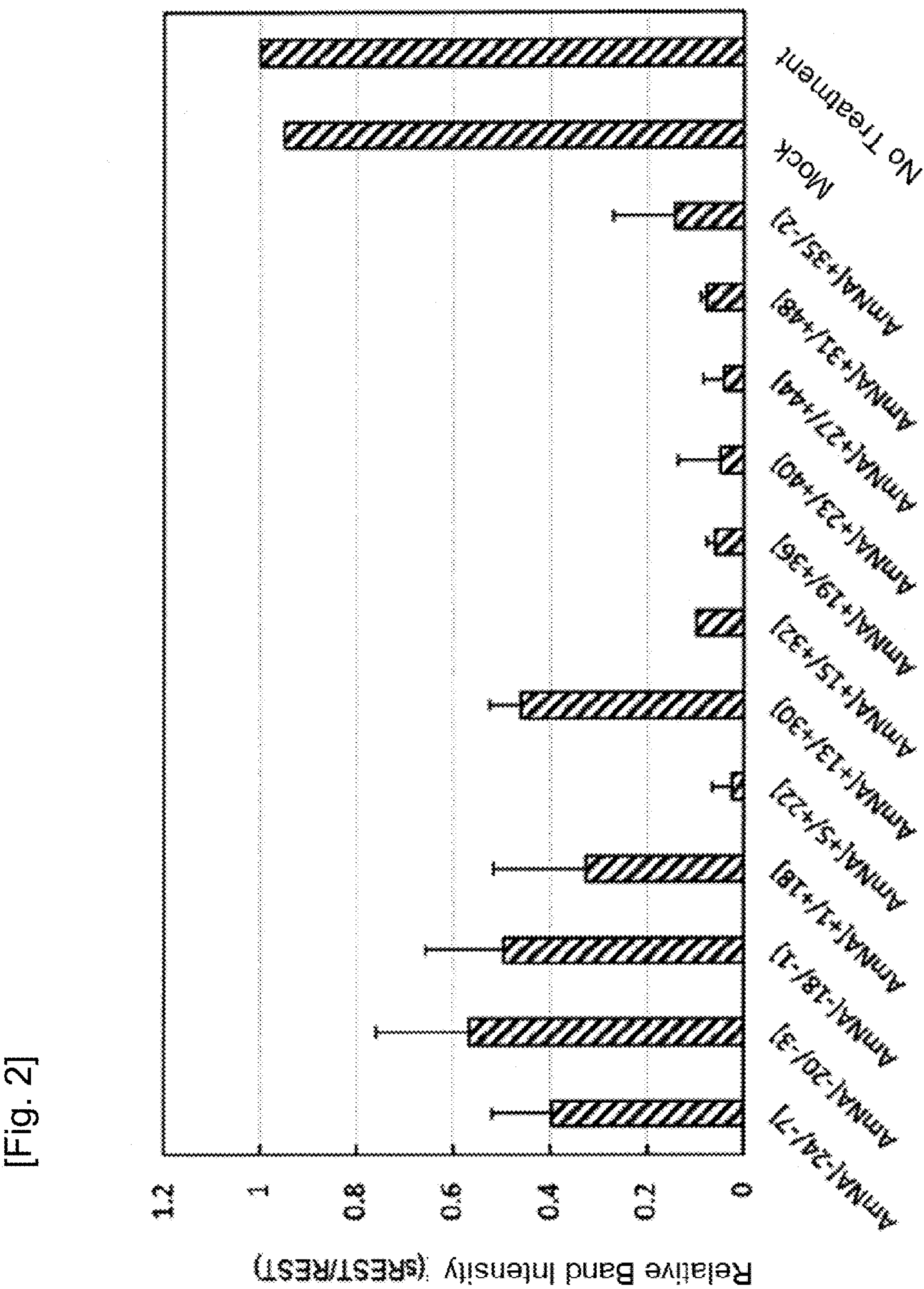

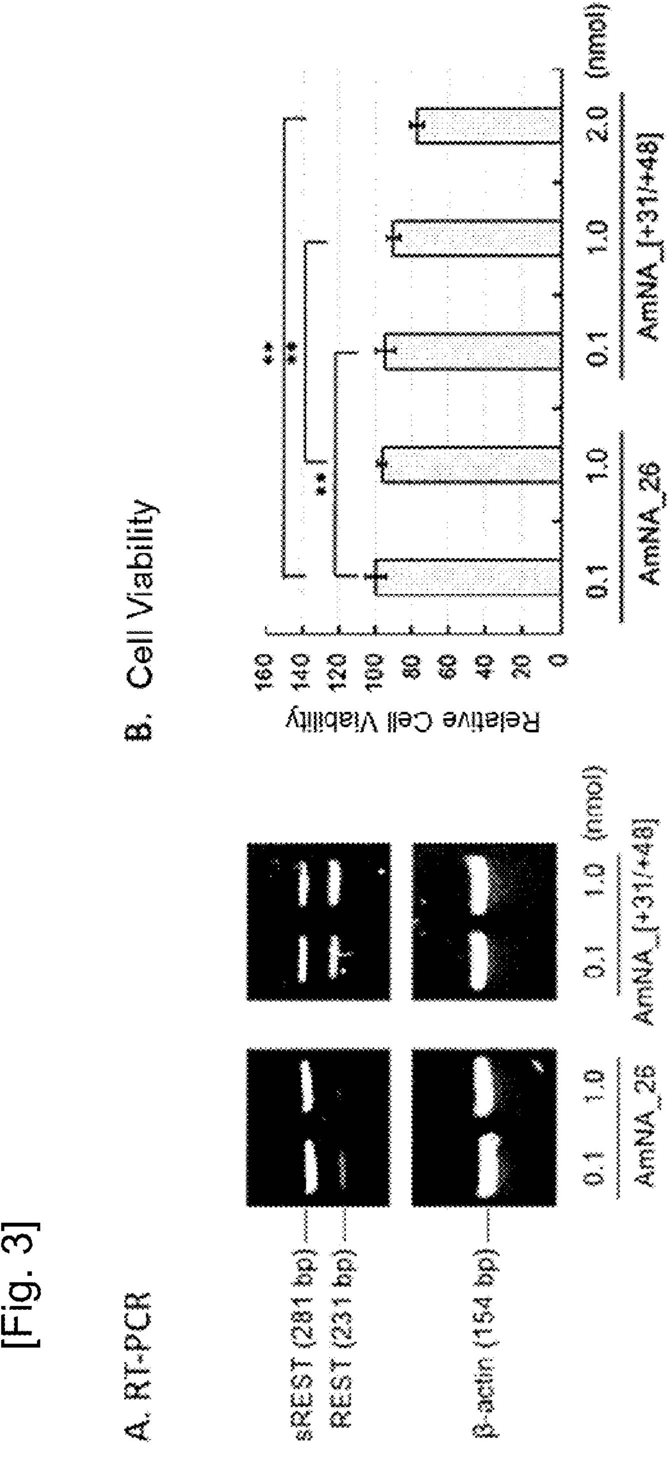
[Fig. 3]
A. RT-PCR
sREST (281 bp)
REST (231 bp)
β-actin (154 bp)
0.1 1.0
AmNA_26
0.1 1.0 (nmol)
AmNA_[+31/+48]
B. Cell Viability
Relative Cell Viability
160
140
120
100
80
60
40
20
0
**
**
**
0.1 1.0
AmNA_26
0.1 1.0 2.0 (nmol)
AmNA_[+31/+48]

[Fig. 4]
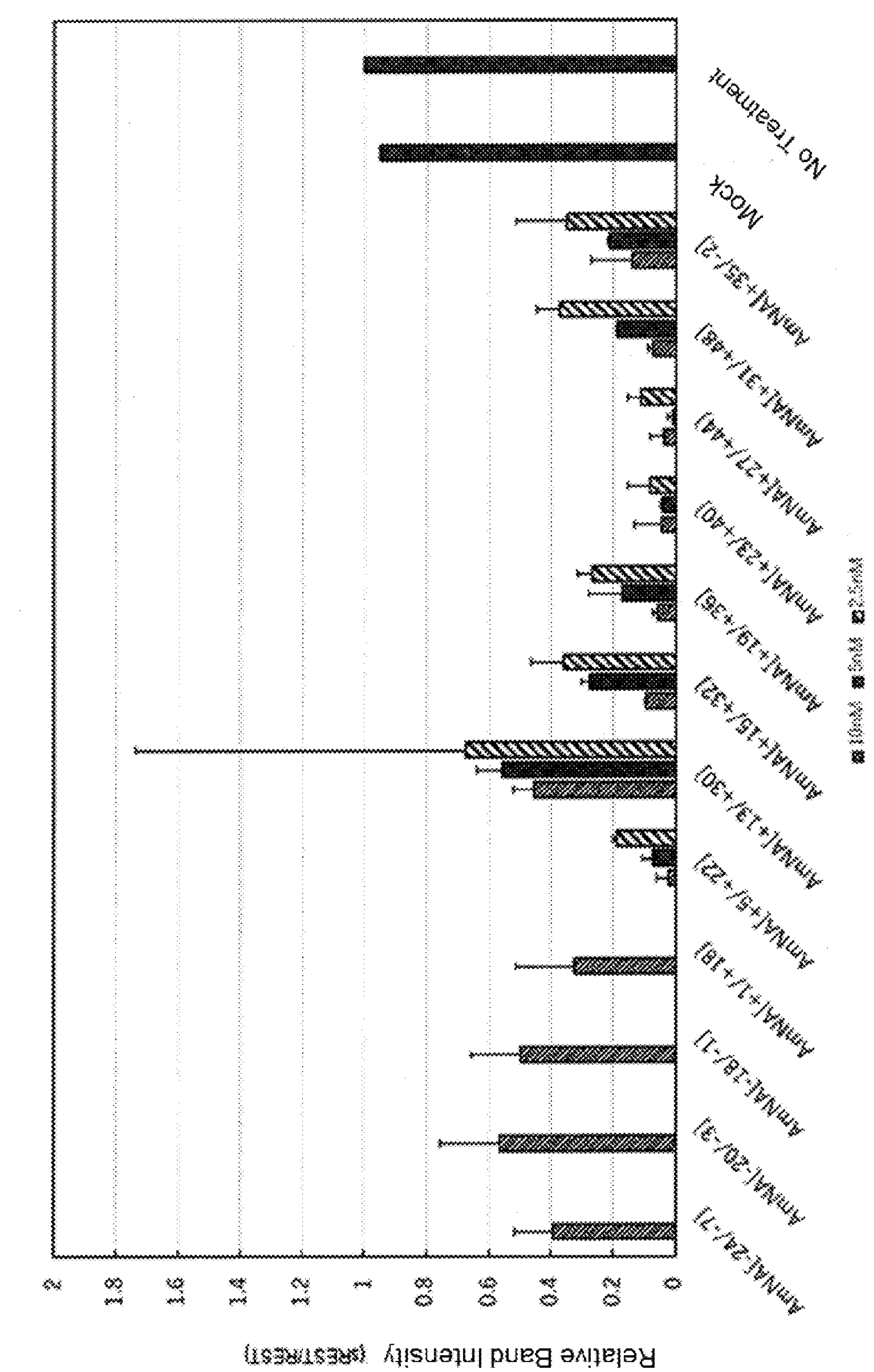

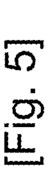
[Fig. 5]
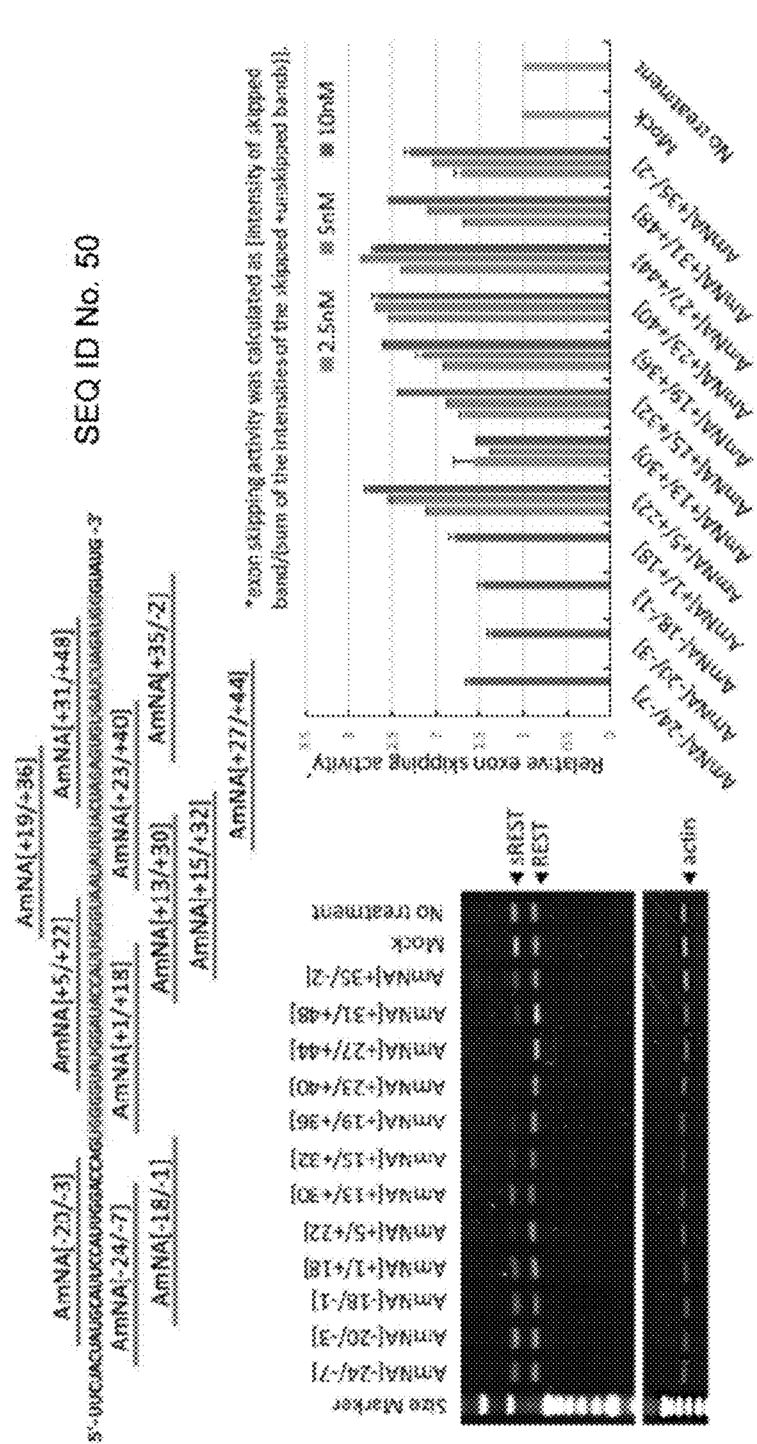

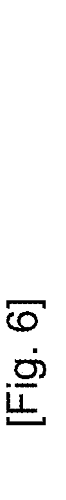
[Fig. 6]
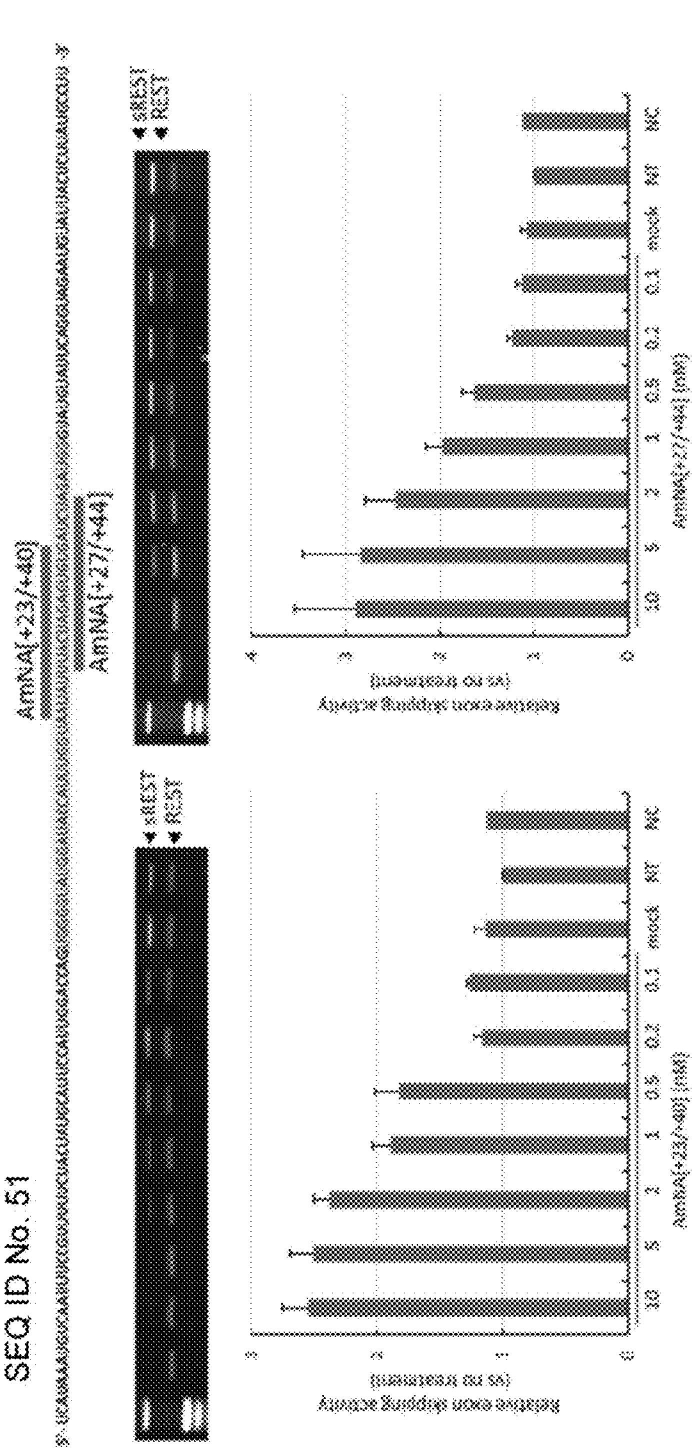

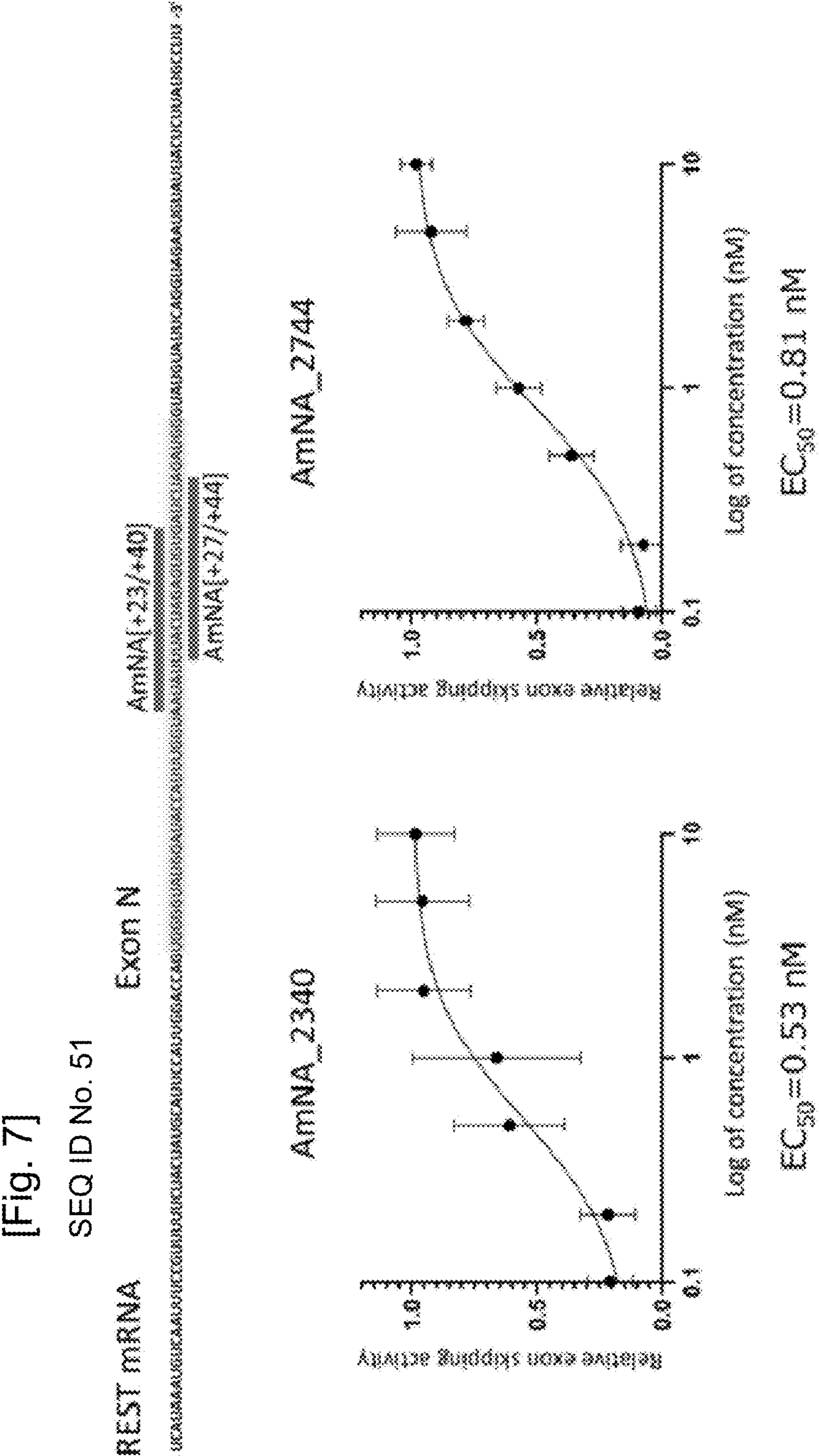
[Fig. 7]

[Fig. 8]
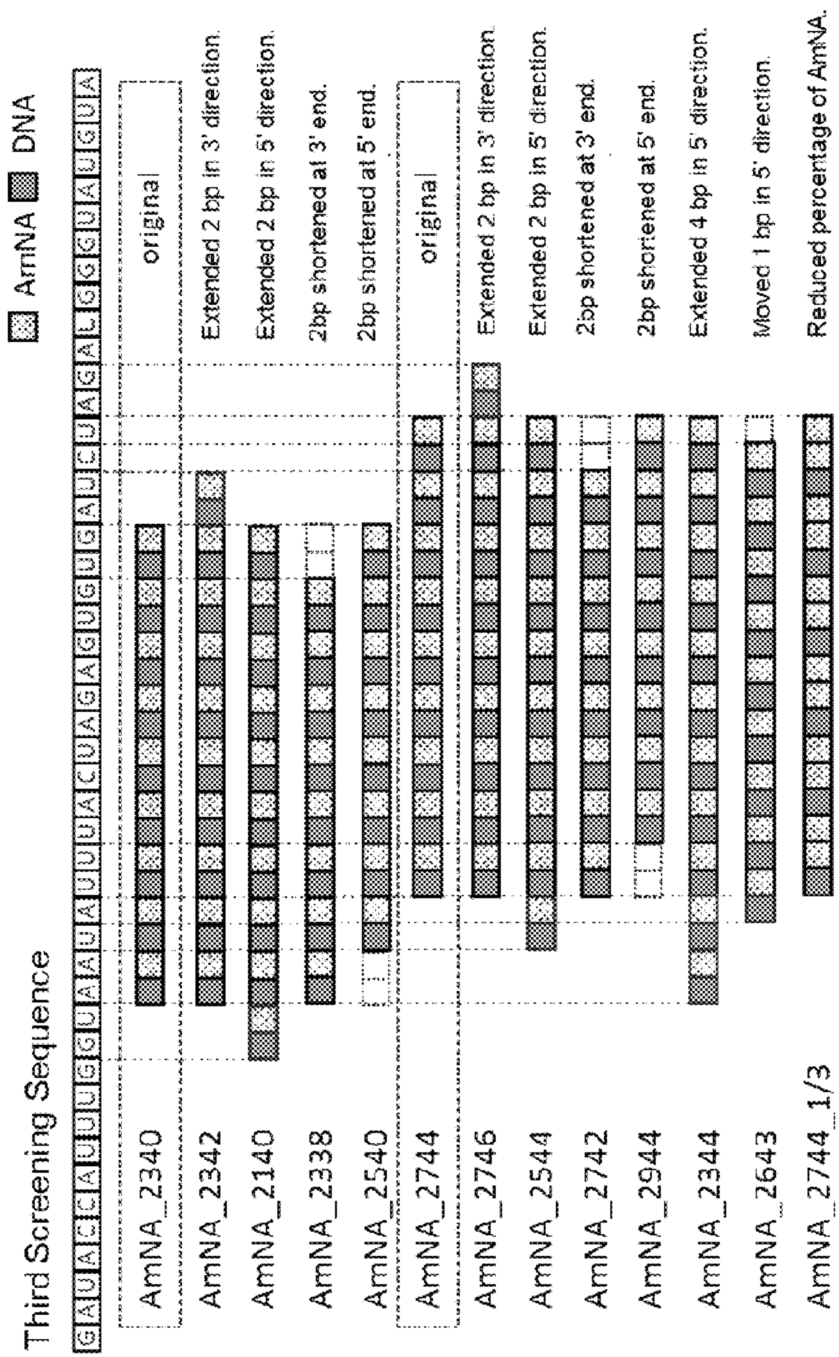

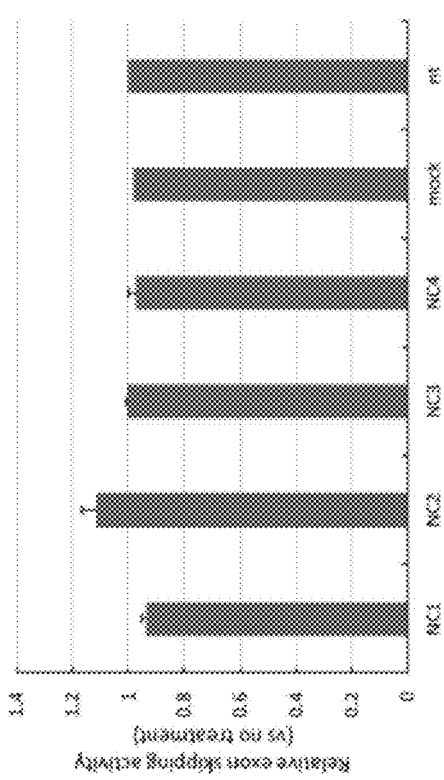
[Fig. 9]
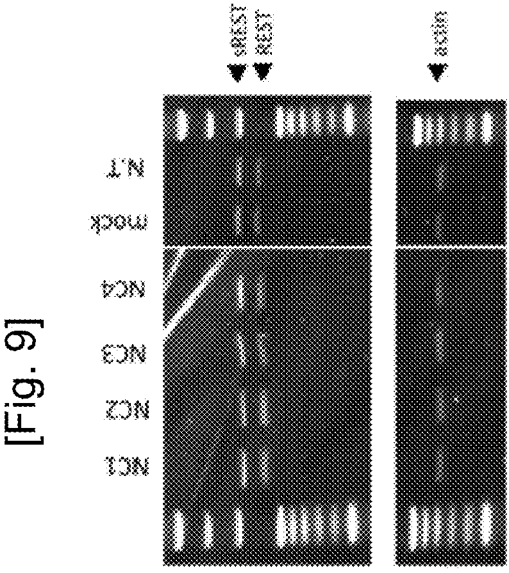

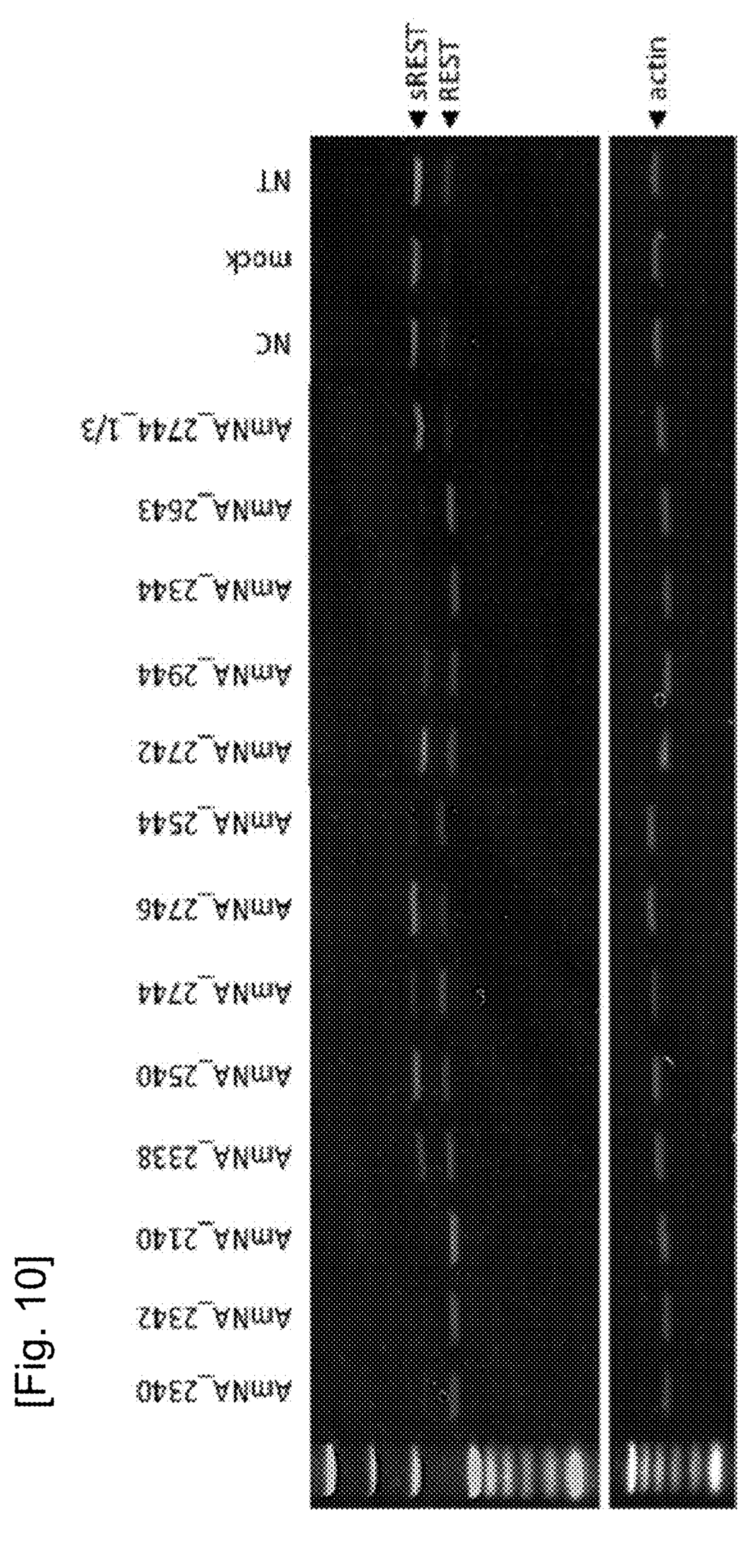
[Fig. 10]

[Fig. 11]
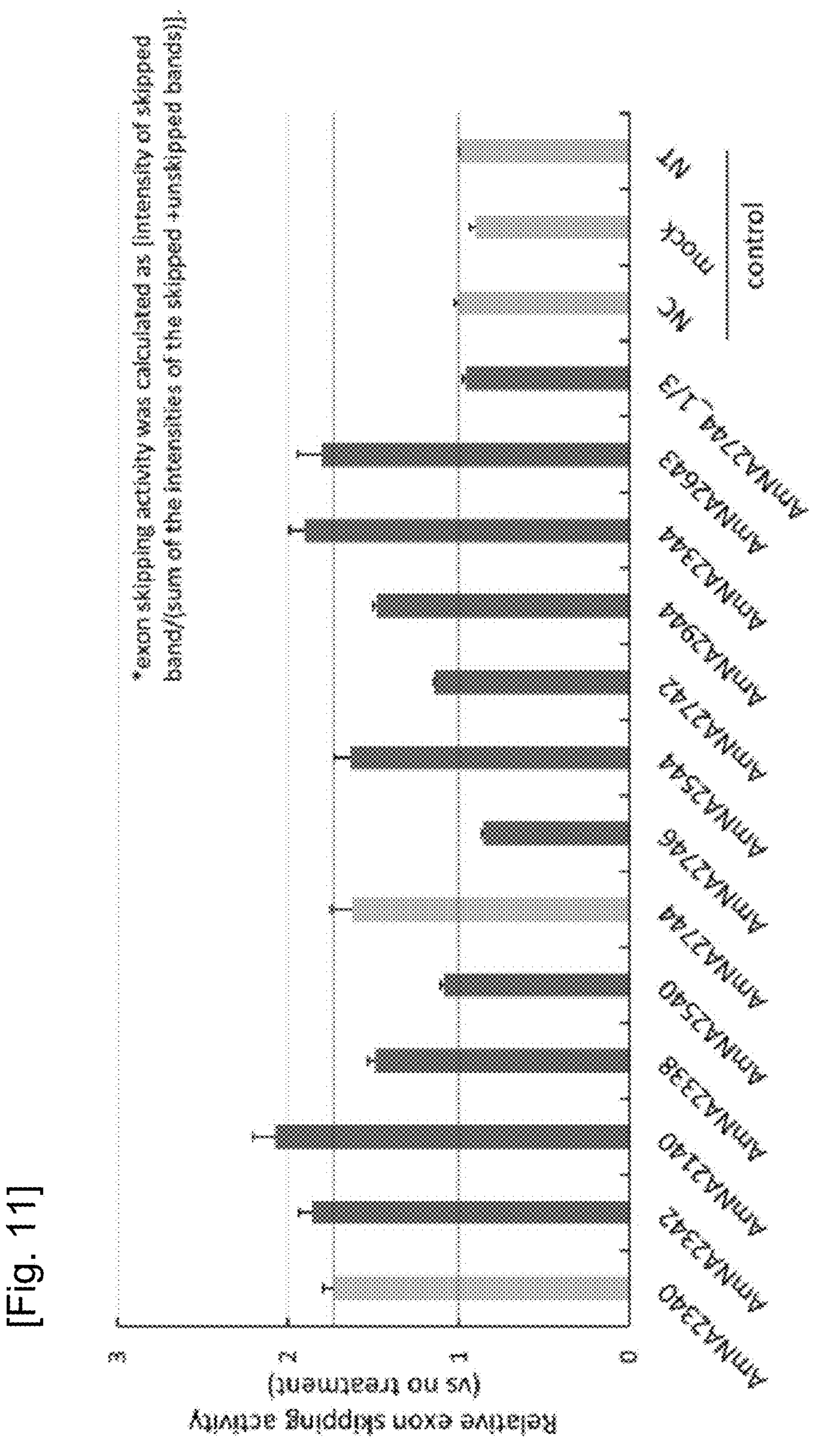

[Fig. 12]
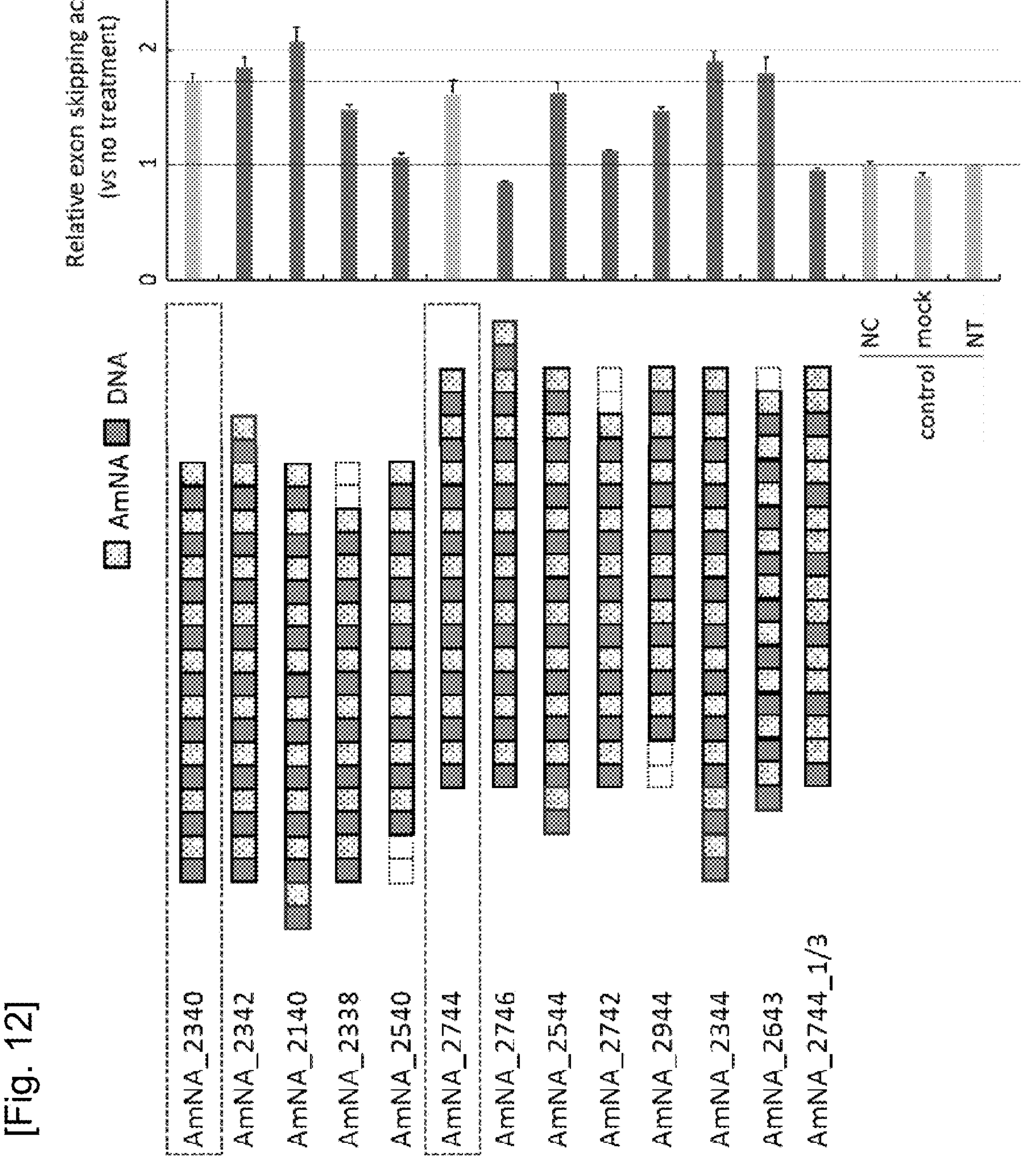

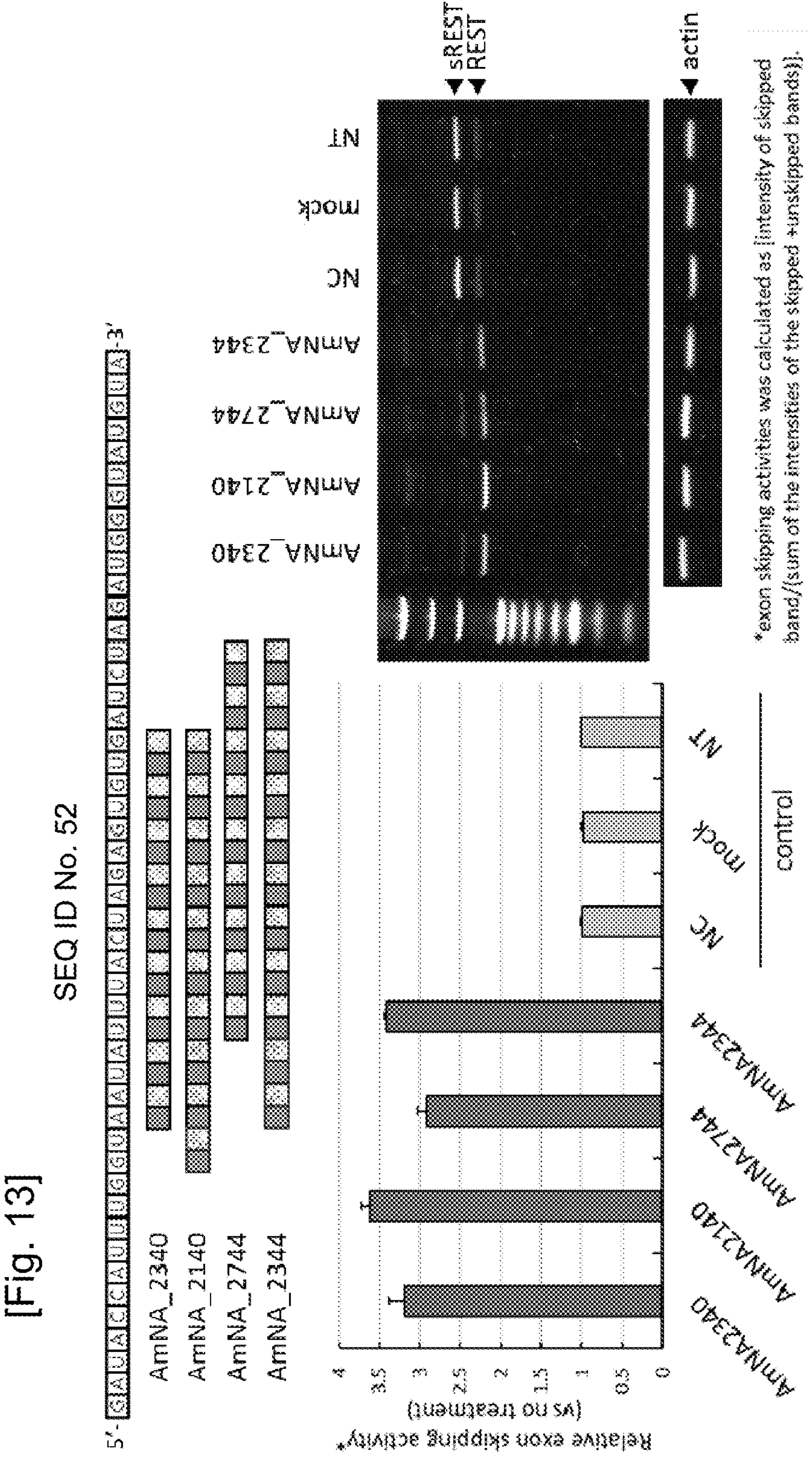
[Fig. 13]
SEQ ID No. 52
5'-
-3'
AmNA_2340
AmNA_2140
AmNA_2744
AmNA_2344
Relative exon skipping activity*
(vs no treatment)
4
3.5
3
2.5
2
1.5
1
0.5
0
AmNA2340
AmNA2140
AmNA2744
AmNA2344
NC
mock
NT
control
sREST
REST
actin
*exon skipping activities was calculated as [intensity of skipped band/(sum of the intensities of the skipped +unskipped bands)].

[Fig. 14]
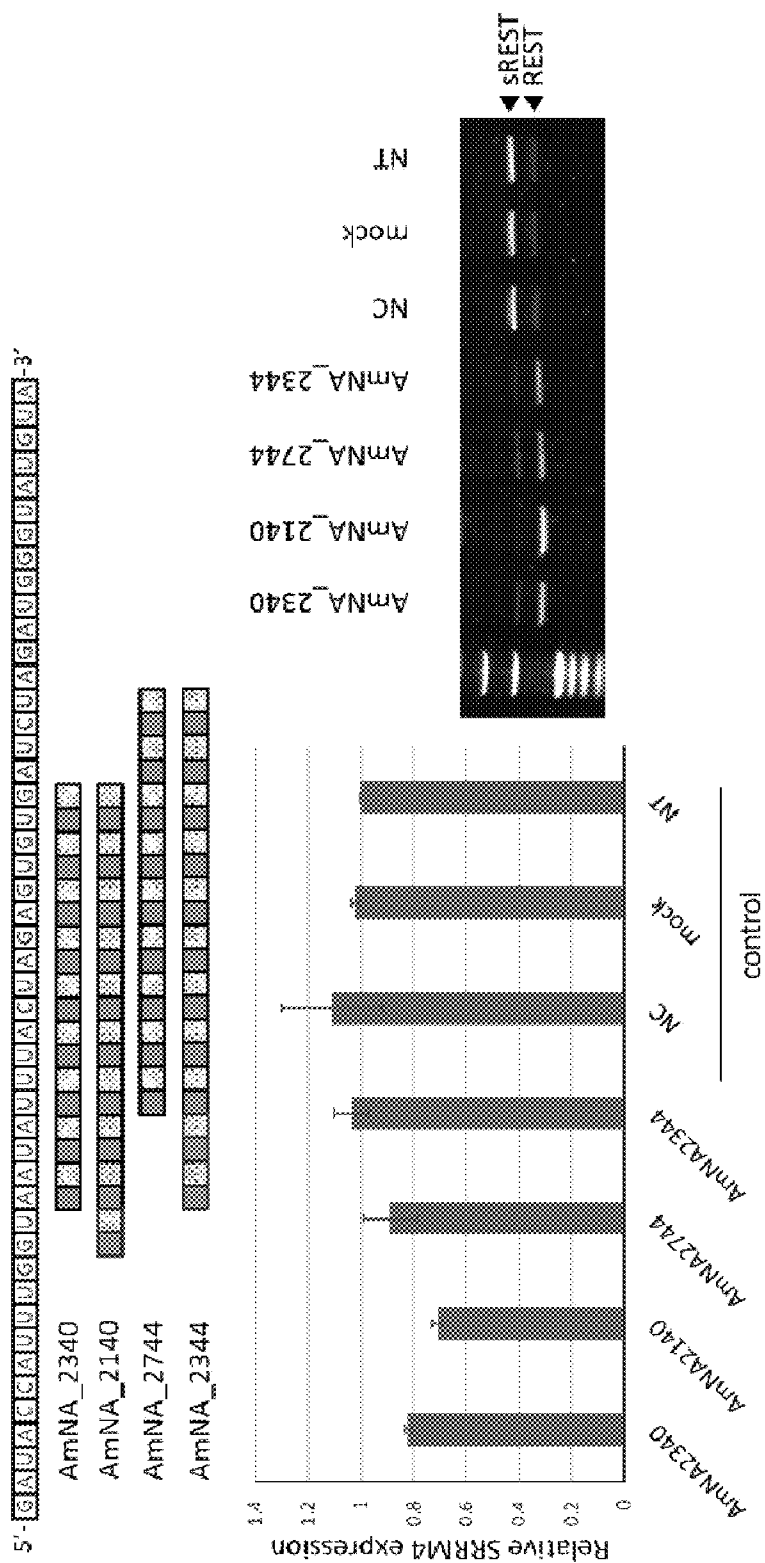

[Fig. 15]
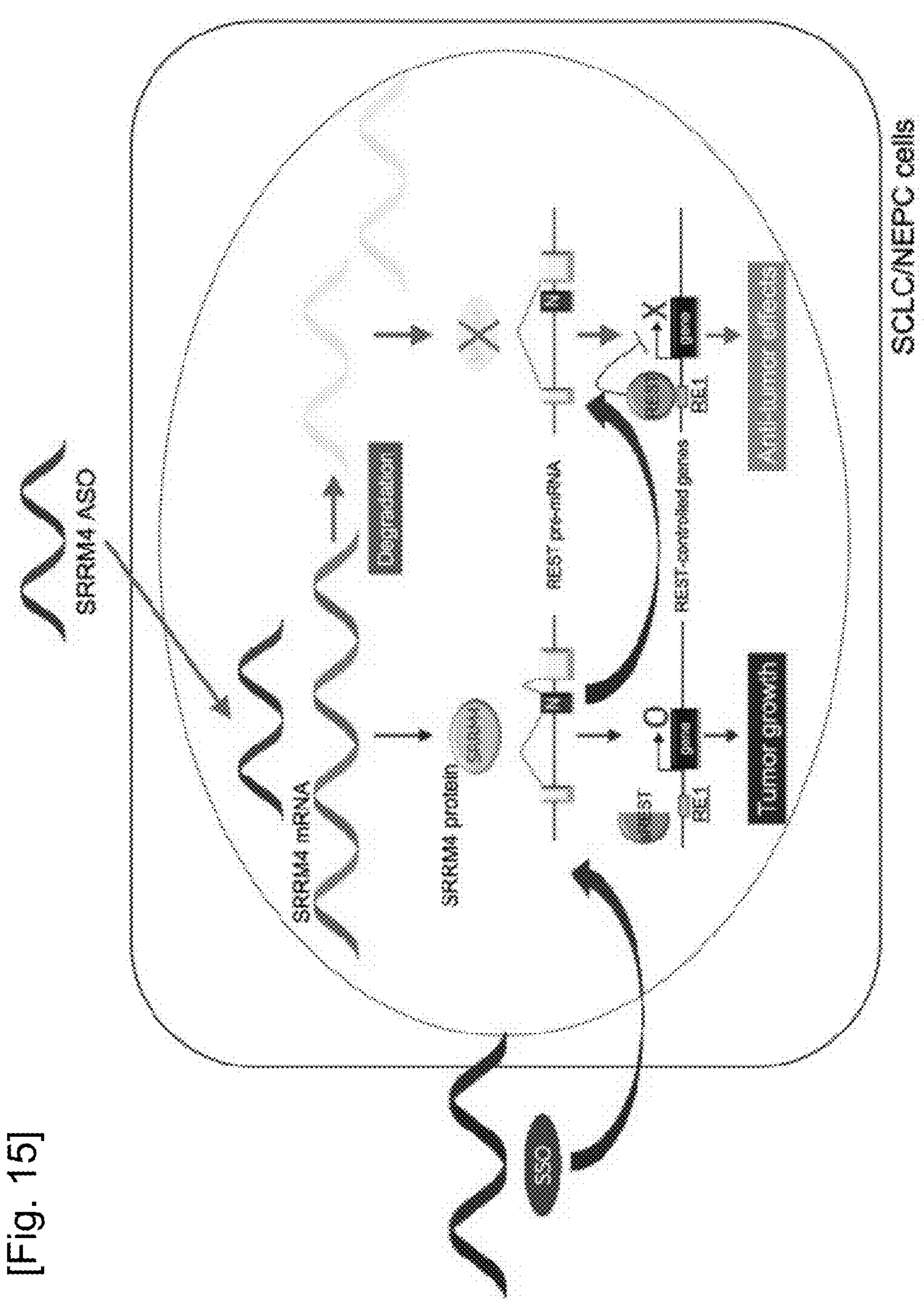

[Fig. 16]
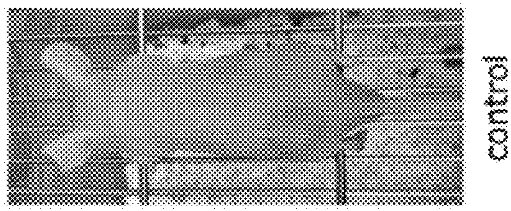
control
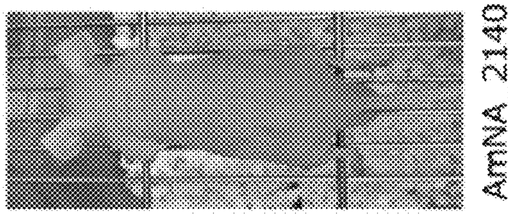
AmNA_2140
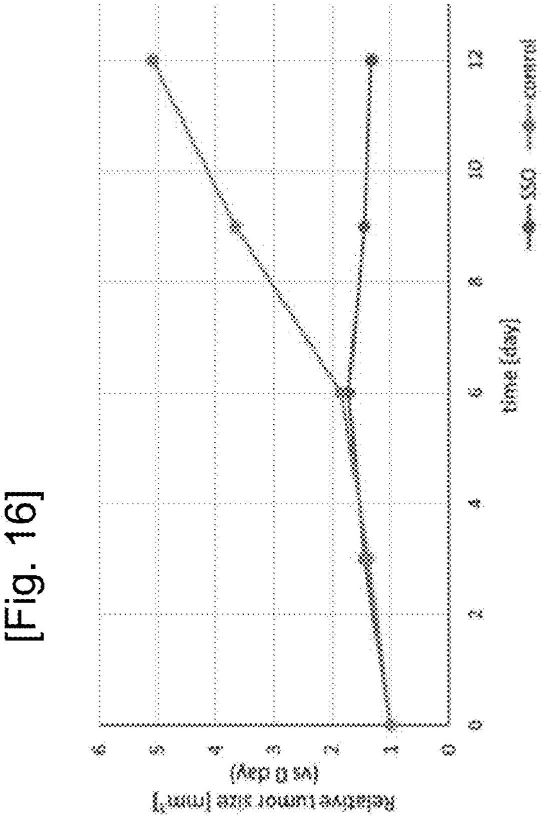

OLIGONUCLEOTIDE FOR INDUCING N-EXON SKIPPING DURING REST mRNA PRECURSOR PROCESSING

TECHNICAL FIELD

The present invention relates to an oligonucleotide that skips N-exon in processing of precursor mRNA (pre-mRNA) of transcriptional repressor REST (RE1-silencing transcription factor) or a pharmacologically acceptable salt thereof, and a pharmaceutical composition containing the same.

BACKGROUND ART

It has been reported that many diseases, cancers, and neurogenerative diseases are associated with gene splicing abnormalities. Out of lung cancers, which are the main cause of cancer-related death, the main treatment policy of small cell lung carcinoma (SCLC) has not changed significantly, and development of new therapeutic agents is urgently needed, for example. Further, cytotoxic chemotherapeutic agents are used in the current SCLC treatment. However, resistance to a pharmaceutical agent in the case of recurrence is a serious problem.

Antisense oligonucleotide (ASO) therapeutics targeting Serine/Arginine Repetitive Matrix 4 (SRRM4) is being developed for clinical trials as a molecular target therapeutic agent (Patent Document 1).

SCLC pathophysiology includes a reduction in the transcriptional repressor REST, which is a tumor suppressor, and abnormal expression of the REST isoform (sREST). Splicing of the transcriptional repressor REST is activated by SRRM4. It has been reported that the transcriptional repressor REST is a master molecule of nervous system genes and a tumor suppressor.

In the research so far, it was believed that SRRM4 antisense oligonucleotide (SRRM4_ASO), which suppresses SRRM4 and exhibits anti-tumor effects, facilitates alterations in the splicing of the tumor suppressor REST, and the resulting increase in the REST expression induces the death of cancer cells. Further, with regard to sREST that is abnormally expressed in SCLC, it has been revealed that SCLC cell death can be induced by directly facilitating splicing alterations such that REST is expressed from sREST (Non-Patent Document 1).

RELATED ART DOCUMENTS

Patent Documents

Patent Document 1: WO2020/027227

Non-Patent Documents

Non-Patent Document 1: Conference Abstracts and Poster of 16$^{th}$ Annual Meeting of the Oligonucleotide Therapeutics Society (2020 Virtual Conference) Sep. 27-30, 2020

SUMMARY OF INVENTION

Problem to be Solved by the Invention

The present invention was made to address the above problems and it is an object thereof to provide an oligonucleotide capable of appropriately inducing REST N-exon skipping or a pharmacologically acceptable salt thereof, and a pharmaceutical composition containing the same.

Means for Solving the Problem

The present invention provides an oligonucleotide or a pharmacologically acceptable salt thereof comprising a nucleotide sequence complementary to a continuous sequence of at least 12 bases in a target region constituted by a base sequence of SEQ ID No. 1;

wherein the oligonucleotide or pharmacologically acceptable salt thereof induces N-exon skipping in human REST pre-mRNA processing.

In one embodiment, the oligonucleotide has a length of 12 to 35 bases.

In one embodiment, the oligonucleotide or pharmacologically acceptable salt thereof has at least one nucleoside structure represented by a formula (I) below:

[Chemical Formula 1]

(I)

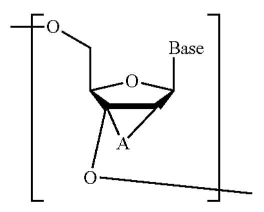

where in the formula (I),

Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, A represents a divalent group represented by the following formulae:

[Chemical Formula 2]

(a-1)

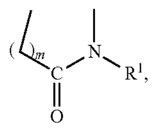

(a-2)

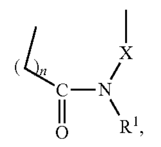

(b-1)

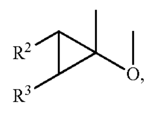

-continued (c-1)

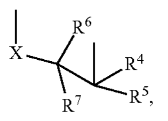

(c-2)

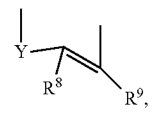

(d-1)

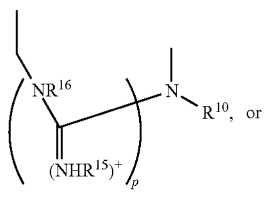

or (e-1)

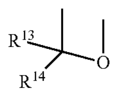

$R^1$ represents a hydrogen atom, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the α group and may have a heteroatom, an aralkyl group with an aryl moiety having 3 to 12 carbon atoms that may have any one or more substituents selected from the α group and may have a heteroatom, or an amino group protecting group for nucleic acid synthesis;

$R^2$ and $R^3$ each independently represent a hydrogen atom; an alkyl group having 1 to 7 carbon atoms that may form a branch or a ring and may have undergone substitution by an aryl group having 3 to 12 carbon atoms that may have a heteroatom; or an aralkyl group with an aryl moiety having 3 to 12 carbon atoms that may have a heteroatom; or $R^2$ and $R^3$ together represent $-(CH_2)_q-$, where q is an integer of 2 to 5;

$R^4$ and $R^5$ each independently represent one selected from the group consisting of a hydrogen atom; a hydroxy group; an alkyl group having 1 to 7 carbon atoms that may form a branch or a ring; an alkoxy group having 1 to 7 carbon atoms that may form a branch or a ring; an amino group; and an amino group protected by a protecting group for nucleic acid synthesis, alternatively, $R^4$ and $R^5$ together represent $=C(R^{11})R^{12}$, where $R^{11}$ and $R^{12}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a linear or branched alkoxy group having 1 to 6 carbon atoms, a linear or branched alkylthio group having 1 to 6 carbon atoms, a cyanoalkoxy group having 1 to 6 carbon atoms, or a linear or branched alkylamino group having 1 to 6 carbon atoms;

$R^6$ and $R^7$ each independently represent a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^8$ represents a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^9$ represents a hydrogen atom, a hydroxy group, an alkyl group having 1 to 7 carbon atoms that may form a branch or a ring, an alkoxy group having 1 to 7 carbon atoms that may form a branch or a ring, an amino group, or an amino group protected by a protecting group for nucleic acid synthesis;

$R^{10}$ represents a hydrogen atom, an alkyl group having 1 to 7 carbon atoms that may form a branch or a ring, an amino group protecting group, or the following,

[Chemical Formula 3]

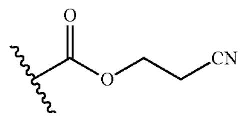

or, $-(C{=}(NHR^{17})^+)-NR^{18}R^{19}$, where $R^{17}$, $R^{18}$, and $R^{19}$ each independently represent a hydrogen atom, an alkyl group having 1 to 7 carbon atoms that may form a branch or a ring, an amino group protecting group, or the following;

[Chemical Formula 4]

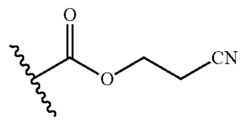

$R^{13}$ and $R^{14}$ each independently represent one selected from the group consisting of a hydrogen atom; a hydroxy group; an alkyl group having 1 to 7 carbon atoms that may form a branch or a ring; an alkoxy group having 1 to 7 carbon atoms that may form a branch or a ring; an amino group; and an amino group protected by a protecting group for nucleic acid synthesis;

m is an integer of 0 to 2;

n is an integer of 0 to 1;

when $R^{10}$ represents a hydrogen atom, an alkyl group having 1 to 7 carbon atoms that may form a branch or a ring, an amino group protecting group, or the following,

[Chemical Formula 5]

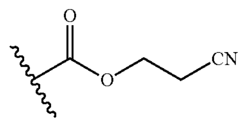

p is 1, and $R^{15}$ and $R^{16}$ each independently represent a hydrogen atom, an alkyl group having 1 to 7 carbon atoms that may form a branch or a ring, an amino group protecting group, or the following,

[Chemical Formula 6]

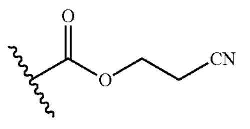

or, when $R^{10}$ represents —(C═(NH$R^{17}$)$^+$)—N$R^{18}R^{19}$, p is 0;

X is an oxygen atom, a sulfur atom, or an amino group; and

Y is an oxygen atom or a sulfur atom.

In one embodiment, a bond between nucleotides that constitute the oligonucleotide contains a phosphorothioate.

In one embodiment, the base sequence of the oligonucleotide includes any of the base sequences of SEQ ID Nos. 3 to 11 and SEQ ID Nos. 40 to 49.

In one embodiment, the nucleoside structure represented by the formula (I) is represented by

[Chemical Formula 7]

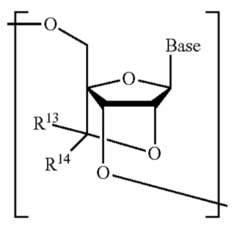

where both $R^{13}$ and $R^{14}$ are hydrogen atoms; or

[Chemical Formula 8]

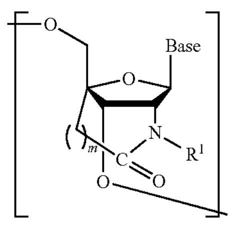

where m is 0, and $R^1$ represents a hydrogen atom, a methyl group, an ethyl group, an n-propyl group, an isopropyl group, a phenyl group, or a benzyl group.

The present invention also provides a pharmaceutical composition comprising the above oligonucleotide or pharmacologically acceptable salt thereof.

In one embodiment, the pharmaceutical composition is a cancer therapeutic agent.

In one embodiment, the pharmaceutical composition is used to treat at least one cancer selected from the group consisting of small cell lung cancer, prostate cancer, and breast cancer.

In one embodiment, the pharmaceutical composition is a heart failure therapeutic agent.

The present invention also provides a method for treating cancer or heart failure in a mammal which comprises administering to the mammal an effective amount of the above oligonucleotide or pharmacologically acceptable salt thereof.

The present invention further provides the above oligonucleotides or pharmacologically acceptable salts thereof for use in the treatment of cancer or heart failure.

The present invention also provides the above oligonucleotides or pharmacologically acceptable salts thereof for producing a therapeutic agent treatment of cancer or heart failure.

Effects of the Invention

An oligonucleotide according to the present invention is capable of inducing N-exon skipping in the REST pre-mRNA processing. Also, anti-tumor effects can be exhibited in vivo. This makes the oligonucleotide useful for the development of a pharmaceutical composition for treating or preventing diseases (e.g., cancer such as small cell lung cancer, or heart failure) associated with REST processing (splicing).

BRIEF DESCRIPTION OF DRAWINGS

FIG. 1 is a graph showing an expression ratio of sREST to REST (sREST/REST) when various antisense oligonucleotides were added to SCLC cells in primary screening.

FIG. 2 is a graph showing an expression ratio of sREST to REST (sREST/REST) when various antisense oligonucleotides were added to prostate cancer cells.

FIG. 3A is a photograph of RT-PCR results showing splicing alterations (N-exon skipping) induced by oligonucleotides (SSOs) targeting REST, and FIG. 3B is a graph showing results of evaluating cell viability.

FIG. 4 is a graph showing that N-exon skipping is dependent on the concentration of oligonucleotides (SSOs) targeting REST.

FIG. 5 shows a positional relationship of oligonucleotides (SSOs) targeting REST in REST pre-mRNA (upper figure), and a graph showing that N-exon skipping is dependent on the concentration of SSOs (lower figure). The base sequence in FIG. 5 is represented by SEQ ID No. 50.

FIG. 6 shows a positional relationship of oligonucleotides (SSOs) targeting REST (specifically, AmNA[+23/+40] (also referred to as "AmNA_2340" hereinafter) and AmNA[+27/+44] (also referred to as "AmNA_2744" hereinafter)) in REST pre-mRNA (upper figure), and a graph showing that N-exon skipping is dependent on the concentration of SSOs (lower figure). The base sequence in FIG. 6 is represented by SEQ ID No. 51.

FIG. 7 shows a positional relationship of oligonucleotides (SSOs) targeting REST (specifically, AmNA[+23/+40] and AmNA[+27/+44]) in REST pre-mRNA (upper figure), and a graph showing the results of analyses of EC50 (Effect Concentration 50; 50% effective concentration) of SSOs (lower figure).

FIG. 8 is a schematic diagram showing SSO sequence lengths and the like in SSO optimization study based on AmNA_2340 and AmNA_2744 in Example 9. The base sequence in FIG. 8 is represented by SEQ ID No. 52.

FIG. 9 shows the results obtained when four negative controls (NC) were designed from a scrambled sequence of AmNA[+35/−2], and alterations in REST splicing caused by NCs were checked using VCaP cells. Because it is preferable that NC does not alter splicing, it was determined that NC3 whose relative exon skipping activity was closest to 1 was determined to be used as NC thereafter.

FIG. 10 is a photograph of RT-PCR results showing splicing alterations (N-exon skipping) induced by oligonucleotides (SSOs) targeting REST.

FIG. 11 is a graph showing results obtained by quantifying relative exon skipping activity using the photograph shown in FIG. 10.

FIG. 12 shows a summary of the results of SSO analysis based on FIGS. 8, 10, and 11.

FIG. 13 shows a positional relationship of oligonucleotides (SSOs) targeting REST in REST pre-mRNA (upper figure), and a photograph of RT-PCR results showing splicing alterations (N-exon skipping) induced by SSOs and a graph showing results obtained by quantifying relative exon skipping activity using the photograph (lower figure).

FIG. 14 shows a positional relationship of oligonucleotides (SSOs) targeting REST in REST pre-mRNA (upper figure), and a graph showing results obtained by quantifying relative SRRM4 expression levels induced by SSOs (lower figure).

FIG. 15 is a schematic diagram showing that, in SCLC/NEPC cells, REST N-exon skipping is controlled by SRRM4 protein, and REST N-exon skipping is controlled by an oligonucleotide (SSO) targeting REST.

FIG. 16 shows results obtained by measuring the tumor size (N417 cells) in vivo using mice. The figure on the right side show an appearance of the mouse tumor 23 days after administration of the tumor to the mouse, and the figure on the left side shows the time course of the tumor size after administration of SSO (AmNA_2140) and physiological saline to the mise. The tumor size was calculated by measuring the long diameter and the short diameter with vernier calipers and using the formula "the tumor size=(long diameter×short diameter$^2$)/2" according to a standard method.

DESCRIPTION OF EMBODIMENTS

Definitions of Terms

First, terms used in this specification are defined.

The term "alkyl group having 1 to 3 carbon atoms" as used herein encompasses any alkyl group having 1 to 3 carbon atoms. Specific examples thereof include a methyl group, an ethyl group, an n-propyl group, and an isopropyl group.

The term "linear alkyl group having 1 to 6 carbon atoms" as used herein encompasses any linear alkyl group having 1 to 6 carbon atoms. Specific examples thereof include a methyl group, an ethyl group, an n-propyl group, an n-butyl group, an n-pentyl group, and an n-hexyl group.

The term "linear alkoxy group having 1 to 6 carbon atoms" as used herein encompasses an alkoxy group having any linear alkyl group having 1 to 6 carbon atoms. Examples thereof include a methyloxy group, an ethyloxy group, and an n-propyloxy group. The term "linear or branched alkoxy group having 1 to 6 carbon atoms" as used herein encompasses an alkoxy group having any linear or branched alkyl group having 1 to 6 carbon atoms. Examples thereof include a methyloxy group, an ethyloxy group, an n-propyloxy group, an isopropyloxy group, an n-butyloxy group, an isobutyloxy group, a tert-butyloxy group, an n-pentyloxy group, and an isopentyloxy group.

The term "linear alkylthio group having 1 to 6 carbon atoms" as used herein encompasses alkylthio groups having any linear alkyl group having 1 to 6 carbon atoms. Examples thereof include a methylthio group, an ethylthio group, and an n-propylthio group. The term "linear or branched alkylthio group having 1 to 6 carbon atoms" as used herein encompasses an alkylthio group having any linear or branched alkyl group having 1 to 6 carbon atoms. Examples thereof include a methylthio group, an ethylthio group, an n-propylthio group, an isopropylthio group, an n-butylthio group, an isobutylthio group, a tert-butylthio group, an n-pentylthio group, and an isopentylthio group.

The term "cyanoalkoxy group having 1 to 6 carbon atoms" as used herein encompasses a group obtained by substituting at least one hydrogen atom included in the linear alkoxy group having 1 to 6 carbon atoms with a cyano group.

The term "linear alkylamino group having 1 to 6 carbon atoms" as used herein encompasses a group obtained by substituting one or two hydrogen atoms included in an amino group with a linear alkyl group having 1 to 6 carbon atoms. Examples thereof include a methylamino group, a dimethylamino group, an ethylamino group, a methylethylamino group, and a diethylamino group. The term "linear or branched alkylamino group having 1 to 6 carbon atoms" as used herein encompasses a group obtained by substituting one or two hydrogen atoms included in an amino group with any linear or branched alkyl group having 1 to 6 carbon atoms. Examples thereof include a methylamino group, a dimethylamino group, an ethylamino group, a methylethylamino group, a diethylamino group, an n-propylamino group, a di-n-propylamino group, an isopropylamino group, and a diisopropylamino group.

The term "alkyl group having 1 to 7 carbon atoms that may form a branch or a ring" as used herein encompasses any linear alkyl groups having 1 to 7 carbon atoms, any branched alkyl groups having 3 to 7 carbon atoms, and any cyclic alkyl groups having 3 to 7 carbon atoms. Such groups may also be referred to as merely as "lower alkyl groups". Examples of any linear alkyl groups having 1 to 7 carbon atoms include a methyl group, an ethyl group, an n-propyl group, an n-butyl group, an n-pentyl group, an n-hexyl group, and an n-heptyl group; examples of any branched alkyl groups having 3 to 7 carbon atoms include an isopropyl group, an isobutyl group, a tert-butyl group, and an isopentyl group; and examples of any cyclic alkyl groups having 3 to 7 carbon atoms include a cyclobutyl group, a cyclopentyl group, and a cyclohexyl group.

The term "alkenyl group having 2 to 7 carbon atoms that may form a branch or a ring" as used herein encompasses any linear alkenyl groups having 2 to 7 carbon atoms, any branched alkenyl groups having 3 to 7 carbon atoms, and any cyclic alkenyl groups having 3 to 7 carbon atoms. Such groups may also be referred to as merely as "lower alkenyl groups". Examples of any linear alkenyl groups having 2 to 7 carbon atoms include an ethenyl group, a 1-propenyl group, a 2-propenyl group, a 1-butenyl group, a 2-butenyl group, a 1-pentenyl group, a 2-pentenyl group, a 3-pentenyl group, a 4-pentenyl group, and a 1-hexenyl group; examples of any branched alkenyl groups having 3 to 7 carbon atoms include an isopropenyl group, a 1-methyl-1-propenyl group, a 1-methyl-2-propenyl group, a 2-methyl- 1 -propenyl group, a 2-methyl-2-propenyl group, and a 1-methyl-2-butenyl group; and examples of any cyclic alkenyl groups having 3 to 7 carbon atoms include a cyclobutenyl group, a cyclopentenyl group, and a cyclohexenyl group.

The term "alkoxy group having 1 to 7 carbon atoms that may form a branch or a ring" as used herein encompasses any linear alkoxy groups having 1 to 7 carbon atoms, any branched alkoxy groups having 3 to 7 carbon atoms, and any cyclic alkoxy groups having 3 to 7 carbon atoms. Such groups may also be referred to as merely as "lower alkoxy groups". Examples of any linear alkoxy groups having 1 to 7 carbon atoms include a methoxy group, an ethoxy group, an n-propoxy group, an n-butyloxy, an n-pentyloxy group, an n-hexyloxy group, and an n-heptyloxy group, and examples of any branched alkoxy groups having 3 to 7 carbon atoms include an isopropoxy group, an isobutyloxy group, a tert-butyloxy group, and an isopentyloxy group, and examples of any cyclic alkoxy groups having 3 to 7 carbon atoms include a cyclobutyloxy group, a cyclopentyloxy group, and a cyclohexyloxy group.

The term "aryl group having 3 to 12 carbon atoms that may have a heteroatom" as used herein encompasses any aryl groups having 6 to 12 carbon atoms that are constituted by only a hydrocarbon, and any heteroaryl groups having 3 to 12 carbon atoms obtained by substituting at least one carbon atom included in the ring structure of the above-mentioned aryl groups with a heteroatom (e.g., a nitrogen atom, an oxygen atom, or a sulfur atom, or a combination thereof). Examples of the aryl groups having 6 to 12 carbon atoms include a phenyl group, a naphthyl group, an indenyl group, and an azulenyl group; and examples of any heteroaryl groups having 3 to 12 carbon atoms include a pyridyl group, a pyrrolyl group, a quinolyl group, an indolyl group, an imidazolyl group, a furyl group, and a thienyl group.

Examples of the term "aralkyl group with an aryl moiety having 3 to 12 carbon atoms that may have a heteroatom" as used herein include a benzyl group, a phenethyl group, a naphthylmethyl group, a 3-phenylpropyl group, a 2-phenylpropyl group, a 4-phenylbutyl group, a 2-phenylbutyl group, a pyridylmethyl group, an indolylmethyl group, a furylmethyl group, a thienylmethyl group, a pyrrolylmethyl group, a 2-pyridylethyl group, a 1-pyridylethyl group, and a 3-thienylpropyl group.

Examples of the term "acyl group" as used herein include aliphatic acyl groups and aromatic acyl groups. Specifically, examples of the aliphatic acyl groups include alkylcarbonyl groups such as a formyl group, an acetyl group, a propionyl group, a butyryl group, an isobutyryl group, a pentanoyl group, a pivaloyl group, a valeryl group, an isovaleryl group, an octanoyl group, a nonanoyl group, a decanoyl group, a 3-methylnonanoyl group, an 8-methylnonanoyl group, a 3-ethyloctanoyl group, a 3,7-dimethyloctanoyl group, an undecanoyl group, a dodecanoyl group, a tridecanoyl group, a tetradecanoyl group, a pentadecanoyl group, a hexadecanoyl group, a 1 -methylpentadecanoyl group, a 14-methylpentadecanoyl group, a 13,13-dimethyltetradecanoyl group, a heptadecanoyl group, a 15-methylhexadecanoyl group, an octadecanoyl group, a 1-methylheptadecanoyl group, a nonadecanoyl group, an eicosanoyl group, and a heneicosanoyl group; carboxylated alkylcarbonyl groups such as a succinoyl group, a glutaroyl group, and an adipoyl group; halogeno lower-alkyl-carbonyl groups such as a chloroacetyl group, a dichloroacetyl group, a trichloroacetyl group, and a trifluoroacetyl group; lower-alkoxy-lower-alkyl-carbonyl groups such as a methoxyacetyl group; and unsaturated alkylcarbonyl groups such as an (E)-2-methyl-2-butenoyl group. Examples of the aromatic acyl groups include arylcarbonyl groups such as a benzoyl group, an α-naphthoyl group, and a β-naphthoyl group; halogeno arylcarbonyl groups such as a 2-bromobenzoyl group and a 4-chlorobenzoyl group; low-alkylated arylcarbonyl groups such as a 2,4,6-trimethylbenzoyl group and a 4-toluoyl group; low-alkoxylated arylcarbonyl groups such as a 4-anisoyl group; carboxylated arylcarbonyl groups such as a 2-carboxybenzoyl group, a 3-carboxybenzoyl group, and a 4-carboxybenzoyl group; nitrated arylcarbonyl groups such as a 4-nitrobenzoyl group and a 2-nitrobenzoyl group; low-alkoxycarbonylated arylcarbonyl groups such as a 2-(methoxycarbonyl)benzoyl group; and arylated arylcarbonyl groups such as a 4-phenylbenzoyl group. A formyl group, an acetyl group, a propionyl group, a butyryl group, an isobutyryl group, a pentanoyl group, a pivaloyl group, and a benzoyl group are favorable.

Examples of the term "silyl group" as used herein include tri-lower-alkyl-silyl groups such as a trimethylsilyl group, a triethylsilyl group, an isopropyldimethylsilyl group, a t-butyldimethylsilyl group, a methyldiisopropylsilyl group, a methyldi-t-butylsilyl group, and a triisopropylsilyl group; and tri-lower-alkyl-silyl groups that have undergone substitution by one or two aryl groups, such as a diphenylmethylsilyl group, a butyldiphenylbutylsilyl group, a diphenylisopropylsilyl group, and a phenyldiisopropylsilyl group. A trimethylsilyl group, a triethylsilyl group, a triisopropylsilyl group, a t-butyldimethylsilyl group, and a t-butyldiphenylsilyl group are favorable, and a trimethylsilyl group is more favorable.

Examples of the term "halogen atom" as used herein include a fluorine atom, a chlorine atom, a bromine atom, and an iodine atom. A fluorine atom or a chlorine atom is favorable.

The term "halide ion" as used herein include a fluoride ion, chloride ion, bromide ion, and iodide iron. A fluoride ion or chloride ion is favorable.

"Protecting groups" in the terms "amino group protecting group for nucleic acid synthesis", "hydroxy group protecting group for nucleic acid synthesis", "hydroxy group protected by a protecting group for nucleic acid synthesis", "phosphate group protected by a protecting group for nucleic acid synthesis", and "mercapto group protected by a protecting group for nucleic acid synthesis" as used herein are not particularly limited as long as they can stably protect an amino group, a hydroxy group, a phosphate group, or a mercapto group during nucleic acid synthesis. Specifically, the protecting groups are stable under an acidic or neutral condition and can be cleaved using chemical techniques such as hydrogenolysis, hydrolysis, electrolysis, and photolysis. Examples of such protecting groups include lower alkyl groups, lower alkenyl groups, acyl groups, tetrahydropyranyl or tetrahydrothiopyranyl groups, tetrahydrofuranyl or tetrahydrothiofuranyl groups, silyl groups, lower-alkoxy-methyl groups, low-alkoxylated lower-alkoxy-methyl groups, halogeno lower-alkoxy-methyl groups, low-alkoxylated ethyl groups, halogenated ethyl groups, methyl groups that have undergone substitution by 1 to 3 aryl groups, "methyl groups that have undergone substitution by 1 to 3 aryl groups in which an aryl ring has undergone substitution by a lower alkyl group, lower alkoxy group, halogen atom, or cyano group", lower-alkoxy-carbonyl groups, "aryl groups that have undergone substitution by a halogen atom, lower alkoxy group, or nitro group", "lower-alkoxy-carbonyl groups that have undergone substitution by a halogen atom or tri-lower-alkyl-silyl group", alkenyloxycarbonyl groups, "aralkyloxycarbonyl groups in which an aryl ring may have undergone substitution by a lower alkoxy group or nitro group", "lower alkoxycarbonyl groups substituted by a cyano group", and "benzenesulfonyl groups that have undergone substitution by 1 to 4 nitro groups".

More specific examples of the tetrahydropyranyl or tetrahydrothiopyranyl groups include a tetrahydropyran-2-yl group, a 3-bromotetrahydropyran-2-yl group, a 4-methoxytetrahydropyran-4-yl group, a tetrahydrothiopyran-4-yl group, and a 4-methoxytetrahydrothiopyran-4-yl group. Examples of the tetrahydrofuranyl or tetrahydrothiofuranyl groups include a tetrahydrofuran-2-yl group and a tetrahydrothiofuran-2-yl group. Examples of the lower-alkoxy-methyl groups include a methoxymethyl group, a 1,1-dimethyl-l-methoxymethyl group, an ethoxymethyl group, a propoxymethyl group, an isopropoxymethyl group, a butoxymethyl group, and a t-butoxymethyl group. An example of the low-alkoxylated lower-alkoxy-methyl groups is a 2-methoxyethoxymethyl group. Examples of the halogeno lower-alkoxy-methyl groups include a 2,2,2-trichloroethoxymethyl group and a bis(2-chloroethoxy) methyl group. Examples of the low-alkoxylated ethyl groups include a 1-ethoxyethyl group and a 1-(isopropoxy)ethyl group. An example of the halogenated ethyl groups is a 2,2,2-trichloroethyl group. Examples of the methyl groups that have undergone substitution by 1 to 3 aryl groups include a benzyl group, an α-naphthylmethyl group, a β-naphthylmethyl group, a diphenylmethyl group, a triphenylmethyl group, an α-naphthyldiphenylmethyl group, and a 9-anthrylmethyl group. Examples of the "methyl groups that have undergone substitution by 1 to 3 aryl groups in which an aryl ring has undergone substitution by a lower alkyl group, lower alkoxy group, halogen atom, or cyano group" include a 4-methylbenzyl group, a 2,4,6-trimethylbenzyl group, a 3,4,5-trimethylbenzyl group, a 4-methoxybenzyl group, a 4-methoxyphenyldiphenylmethyl group, a 4,4'-dimethoxytriphenylmethyl group, a 2-nitrobenzyl group, a 4-nitrobenzyl group, a 4-chlorobenzyl group, a 4-bromobenzyl group, and a 4-cyanobenzyl group. Examples of the lower-alkoxy-carbonyl groups include a methoxycarbonyl group, an ethoxycarbonyl group, a t-butoxycarbonyl group, and an isobutoxycarbonyl group. Examples of the "aryl groups that have undergone substitution by a halogen atom, lower alkoxy group, or nitro group" include a 4-chlorophenyl group, a 2-fluorophenyl group, a 4-methoxyphenyl group, a 4-nitrophenyl group, and a 2,4-dinitrophenyl group. Examples of the "lower-alkoxy-carbonyl groups that have undergone substitution by a halogen atom or tri-lower-alkyl-silyl group" include a 2,2,2-trichloroethoxycarbonyl group and 2-trimethylsilylethoxycarbonyl group. Examples of the alkenyloxycarbonyl groups include a vinyloxycarbonyl group and an aryloxycarbonyl group. Examples of the "aralkyloxycarbonyl groups in which an aryl ring may have undergone substitution by a lower alkoxy group or nitro group" include a benzyloxycarbonyl group, a 4-methoxybenzyloxycarbonyl group, a 3,4-dimethoxybenzyloxycarbonyl group, a 2-nitrobenzyloxycarbonyl group, and a 4-nitrobenzyloxycarbonyl group. Examples of the "lower-alkoxy-carbonyl groups that have undergone substitution by a cyano group" include a cyanoethoxycarbonyl group. Examples of the "benzenesulfonyl groups that have undergone substitution by 1 to 4 nitro groups" include a 2-nitrobenzenesulfonyl group and a 2,4-dinitrobenzenesulfonyl group.

Preferable examples of the "hydroxy group protecting group for nucleic acid synthesis" include aliphatic acyl groups, aromatic acyl groups, methyl groups that have undergone substitution by 1 to 3 aryl groups, "methyl groups that have undergone substitution by 1 to 3 aryl groups in which an aryl ring has undergone substitution by a lower alkyl, lower alkoxy, halogen, or cyano group", and silyl groups. More preferable examples thereof include an acetyl group, a benzoyl group, a benzyl group, a p-methoxybenzoyl group, a dimethoxytrityl group, a monomethoxytrityl group, and a tert-butyldiphenylsilyl group. Favorable examples of the protecting group used for the "hydroxy group protected by a protecting group for nucleic acid synthesis" include aliphatic acyl groups, aromatic acyl groups, "methyl groups that have undergone substitution by 1 to 3 aryl groups", "aryl groups that have undergone substitution by a halogen atom, lower alkoxy group, or nitro group", lower alkyl groups, and lower alkenyl groups. More favorable examples thereof include a benzoyl group, a benzyl group, a 2-chlorophenyl group, a 4-chlorophenyl group, and a 2-propenyl group. An acyl group is favorable as the "amino group protecting group for nucleic acid synthesis", and a benzoyl group is more favorable. Favorable examples of the "protecting group" used for the "phosphate group protected by a protecting group for nucleic acid synthesis" include lower alkyl groups, lower alkyl groups that have undergone substitution by a cyano group, aralkyl groups, "aralkyl groups in which an aryl ring has undergone substitution by a nitro group or halogen atom", and "aryl groups that have undergone substitution by a lower alkyl group, halogen atom, or nitro group". Alternatively, more favorable examples thereof include a 2-cyanoethyl group, a 2,2,2-trichloroethyl group, a benzyl group, a 2-chlorophenyl group, and a 4-chlorophenyl group. One or more protecting groups may constitute the "phosphate group protected by a protecting group for nucleic acid synthesis". Aliphatic acyl groups and aromatic acyl groups are favorable as the "protecting group" used for the "mercapto group protected by a protecting group for nucleic acid synthesis", and a benzoyl group is more favorable.

Examples of the "amino group protecting group" relating to the $R^{10}$ group in this specification include an acetyl group, a tert-butoxycarbonyl (Boc) group, and a 9-fluorenylmethyloxycarbonyl (Fmoc) group.

In this specification, among groups represented by $—P(R^{24})R^{25}$, where $R^{24}$ and $R^{25}$ each independently represent a hydroxy group, a hydroxy group protected by a protecting group for nucleic acid synthesis, a mercapto group, a mercapto group protected by a protecting group for nucleic acid synthesis, an amino group, a linear or branched alkoxy group having 1 to 6 carbon atoms, a linear or branched alkylthio group having 1 to 6 carbon atoms, a cyanoalkoxy group having 1 to 6 carbon atoms, or a linear or branched alkylamino group having 1 to 6 carbon atoms, a group in which $R^{24}$ can be represented by $—OR^{24a}$ and $R^{25}$ can be represented by $—N(R^{25a})_2$ is referred to as a "phosphoramidite group". Favorable examples of the phosphoramidite group include a group represented by a formula $—P(OC_2H_4CN)(N(iPr)_2)$ and a group represented by a formula $—P(OCH_3)(N(iPr)_2)$. In these formulae, iPr represents an isopropyl group.

The term "nucleoside" as used herein refers to "nucleosides" in which a purine base or a pyrimidine base binds to sugar, as well as "nucleosides" in which a heteroaromatic ring or an aromatic hydrocarbon ring other than purine and pyrimidine that can serve as a substitute for a purine or pyrimidine base binds to sugar. Nucleosides of a natural type are also referred to as "natural nucleosides". "Modified non-natural nucleosides" are also referred to as "modified nucleosides", and in particular, nucleotides with sugar moieties modified are referred to as "sugar-modified nucleosides". A "nucleotide" refers to a compound in which a phosphate group binds to sugar of a nucleoside.

The term "oligonucleotide" as used herein refers to a polymer of "nucleotides" in which, for example, two to fifty of the same or different "nucleosides" are bound via phosphodiester bonds or other bonds, and includes natural and non-natural polymers thereof. Favorable examples of non-natural "oligonucleotide" include sugar derivatives with sugar moieties modified; thioated derivatives with phosphate diester moieties thioated; esters with terminal phosphate moieties esterificated; and amides in which amino groups on purine bases are amidated. More favorable examples thereof include sugar derivatives with sugar moieties modified.

The term "salt thereof" as used herein refers to a salt of a compound represented by a formula (II) described later. Examples of such salt include metal salts including alkali metal salts such as sodium salts, potassium salts, and lithium salts, alkali earth metal salts such as calcium salts and magnesium salts, and aluminum salts, iron salts, zinc salts, copper salts, nickel salts, and cobalt salts; amine salts including inorganic salts such as ammonium salts, and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts; inorganic acid salts including halide hydroacid salts such as hydrofluoric acid salts, hydrochloric acid salt, hydrobromic acid salts, and hydroiodic acid salts, nitrates, perchlorates, sulfates, and phosphates; organic acid salts including lower-alkane-sulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates and maleates; and amino acid salts such as glycine salts, lysine salts, arginine salts, ornithine salts, glutamates, and aspartates.

The term "pharmacologically acceptable salt thereof" as used herein refers to a salt of an oligonucleotide containing at least one nucleoside structure represented by a formula (I) below, and a physiologically and pharmaceutically acceptable salt of an oligonucleotide, i.e., a salt that retains a desired biological activity of the oligonucleotide and does not impart an undesired toxicological effect. Examples of such salts include metal salts including alkali metal salts such as sodium salts, potassium salts, and lithium salts, alkali earth metal salts such as calcium salts and magnesium salts, and aluminum salts, iron salts, zinc salts, copper salts, nickel salts, and cobalt salts; amine salts including inorganic salts such as ammonium salts, and organic salts such as t-octylamine salts, dibenzylamine salts, morpholine salts, glucosamine salts, phenylglycine alkylester salts, ethylenediamine salts, N-methylglucamine salts, guanidine salts, diethylamine salts, triethylamine salts, dicyclohexylamine salts, N,N'-dibenzylethylenediamine salts, chloroprocaine salts, procaine salts, diethanolamine salts, N-benzyl-phenethylamine salts, piperazine salts, tetramethylammonium salts, and tris(hydroxymethyl)aminomethane salts; inorganic acid salts including halide hydroacid salts such as hydrofluoric acid salts, hydrochloric acid salt, hydrobromic acid salts, and hydroiodic acid salts, nitrates, perchlorates, sulfates, and phosphates; organic acid salts including lower-alkane-sulfonates such as methanesulfonates, trifluoromethanesulfonates, and ethanesulfonates, arylsulfonates such as benzenesulfonates and p-toluenesulfonates, acetates, malates, fumarates, succinates, citrates, tartrates, oxalates and maleates; and amino acid salts such as glycine salts, lysine salts, arginine salts, ornithine salts, glutamates, and aspartates.

Oligonucleotide

Hereinafter, the present invention will be described in detail.

An oligonucleotide according to the present invention has the activity of inducing N-exon skipping in the REST pre-mRNA processing. Such an oligonucleotide may be a pharmacologically acceptable salt thereof. Regarding the REST gene, the base sequence information of the human REST gene is available as NCBI Reference Sequence: NG_029447.1 Homo sapiens RE1 silencing transcription factor (REST), RefSeqGene on chromosome 4. The base sequence of SEQ ID No. 1 in the sequence list corresponds to a base sequence from position 24740 to position 24789 of the human REST gene, and spans the entire length of N-exon. N-exon is located between exon 3 and exon 4.

The "activity of inducing N-exon skipping in the REST pre-mRNA processing" as used herein means that an oligonucleotide binds to REST pre-mRNA and induces N-exon skipping during processing of the pre-mRNA, as a result of which the expression of REST is facilitated and/or the expression of sREST, which is a mutant, is suppressed. An oligonucleotide is an antisense oligonucleotide (ASO) to REST mRNA or pre-mRNA. This oligonucleotide is also referred to as "Splice-Switching Oligonucleotide (SSO)" because the oligonucleotide has the activity of inducing N-exon skipping, thereby controlling REST expression and sREST expression through pre-mRNA splicing.

The activity of inducing N-exon skipping can be obtained by measuring REST and sREST expression levels and an expression ratio of sREST to REST using a known method (e.g., reverse transcription polymerase chain reaction (RT-PCR)). Oligonucleotides having N-exon skipping activity may be concentration dependent, for example, in in vitro mRNA expression experiments as described in Example 3 or Example 4 below or experiments equivalent thereto, and the N-exon skipping activity can be checked by measuring the ratio of sREST to REST (sREST/REST) or a percentage of REST to "the sum of REST and sREST" ("% exclusion") based on band intensity. The higher the skipping inducing activity is, the lower the "sREST/REST" is, and the higher the "% exclusion" is. The "sREST/REST" is lower than that in a case where no antisense oligonucleotide is added (control), and when the "sREST/REST" in the control is set to 1 (in other words, the "sREST/REST" of an oligonucleotide is divided by the "sREST/REST" of the control), the "sREST/REST" is 0.8 or less, preferably 0.7 or less, more preferably 0.6 or less, and even more preferably 0.4 or less, and may be 0.2 or less, for example. Further, in this specification, the "relative exon skipping activity" can be calculated by dividing "% exclusion" of the oligonucleotide by "% exclusion" of the control. The "relative exon skipping activity" is 1.2 or more, preferably 1.4 or more, more preferably 1.6 or more, even more preferably 1.8 or more, and may be 2.0 or more, for example.

Furthermore, the wording "oligonucleotide "binds" to REST pre-mRNA" means that different single-stranded oligonucleotides or nucleic acids can form a nucleic acid constituted by two or more strands through nucleobase complementarity. Favorably, a double-stranded nucleic acid can be formed. There is no particular limitation on a melting temperature ($T_m$) of a double-stranded or higher stranded nucleic acid, which is an indicator of thermal stability of binding. The melting temperature ($T_m$) of a double-stranded nucleic acid can be determined, for example, as follows: an oligonucleotide and a target RNA are mixed in equal molar amounts in a buffer solution (8.1 mM $Na_2HPO_4$, 2.68 mM KCl, 1.47 mM $KH_2PO_4$, pH7.2), heated at 95° C. for 5 minutes, and annealed to room temperature to form a double-stranded nucleic acid. A change in absorbance (A) at 260 nm with temperature (T) is measured when the double-stranded nucleic acid is heated from 20° C. to 95° C. at a temperature increase rate of 0.5° C./min, a graph of dA/dT vs T is created based on the measurement results, and in the graph, the temperature at which the value of dA/dT is the largest, i.e., the temperature at which the change in A due to T is the largest, is used as $T_m$ of the double-stranded nucleic acid. The melting temperature ($T_m$) is 40° C. or more, for example, and preferably 50° C. or more.

The term "complementary" used herein means that two different single-stranded oligonucleotides or nucleic acids are in a pairing relationship that allows the two different single-stranded oligonucleotides or nucleic acids to form a double-stranded nucleic acid. Base sequences of a double-strand forming region are preferably completely complementary, but may have one or several mismatches as long as they can form the double-stranded nucleic acid and have N-exon skipping action. One or several mismatches refer to one to four mismatches, preferably one to three mismatches, and more preferably one or two mismatches, depending on the length of an oligonucleotide. The oligonucleotide according to the present invention is preferably complementary to 80% or more, 90% or more, 95% or more, 96% or more, 97% or more, 98% or more, or 99% or more of the base sequence of the double-strand forming region, or may be completely (100%) complementary thereto.

Examples of the oligonucleotide having the activity of inducing N-exon skipping in the REST pre-mRNA processing (splicing) includes antisense oligonucleotides (ASOs) targeting the REST gene. The term "antisense oligonucleotide (ASO)" refers to a single-stranded oligonucleotide that can bind to RNA (e.g., mRNA or pre-mRNA)/DNA of a target gene, has the activity of controlling the expression of the target gene (including splicing control), and is complementary to a sequence of RNA (e.g., mRNA or pre-mRNA)/DNA of the target gene. The antisense oligonucleotide (ASO) according to the present invention refers to a "Splice-Switching Oligonucleotide (SSO)" in that it is capable of target gene splicing control.

The oligonucleotide according to the present invention can bind to a target region, which is at least a portion of SEQ ID No. 1. Also, the oligonucleotide according to the present invention can bind to a target region, which is at least a portion of SEQ ID No. 38 or 39. The sequences represented by SEQ ID Nos. 38 and 39 are both partial regions of SEQ ID No. 1. A predetermined "target region" refers to a region of pre-mRNA represented by any one of SEQ ID Nos. 1, 38, and 39, for example. The target region is preferably a region associated with the activity of inducing N-exon skipping in REST. With the oligonucleotide according to the present invention, a target region has, for example, at least a length of 12 bases, and a length of 12, 13, 14, 15, 16, 17, 18, 19, 20, 21, 22, 23, 24, 25, 26, 27, 28, 29, 30, 31, 32, 33, 34, or 35 bases, for example, but the number of bases in the region is not limited thereto. The wording "a nucleic acid molecule or an oligonucleotide "binds to a target region"" indicates that the nucleic acid molecule or oligonucleotide does not need to form two or more strands (preferably double strands) with the entire target region, and may form two or more strands (preferably double strands) with a partial region of the target region, as long as the nucleic acid molecule or oligonucleotide exhibits the activity of inducing N-exon skipping during REST pre-mRNA processing. An oligonucleotide having the activity of inducing N-exon skipping of REST pre-mRNA is, for example, complementary to the nucleotide sequence of the target region, which is at least a portion of SEQ ID No. 1, and preferably has complete complementarity.

The oligonucleotide (e.g., antisense oligonucleotide) according to the present invention has at least a length of 12 bases, and a length of 12, 13, 14, 15, 16, 17, 18, 19, 20, 21, 22, 23, 24, 25, 26, 27, 28, 29, 30, 31, 32, 33, 34, or 35 bases, for example. Oligonucleotides having the above length can more effectively bind to REST pre-mRNA and effectively induce N-exon skipping.

The oligonucleotide (e.g., antisense oligonucleotide) according to the present invention is an oligonucleotide having the activity of inducing N-exon skipping of REST pre-mRNA, and includes a sequence that is complementary to at least 12 bases of the target region constituted by the base sequence of SEQ ID No. 1, for example. The oligonucleotide does not need to be entirely complementary to the target region constituted by the base sequence of SEQ ID No. 1, and a portion of the oligonucleotide may be complementary to a peripheral region (e.g., a portion extended by 1 to 5 bases to the 5'-end side and/or 3'-end side of the target region) (represented by SEQ ID No. 2), for example. The same applies to SEQ ID Nos. 38 and 39. In an embodiment, the sequence of an antisense oligonucleotide based on a selected target region, such as the oligonucleotide (e.g., antisense oligonucleotide) according to the present invention, can be designed using a method commonly used by persons skilled in the art.

The following sequences (bases are aligned in a direction from 5' toward 3') are examples of the base sequence of the antisense oligonucleotide (Numerical values in the square brackets [ ] indicate a sequence targeted by the oligonucleotide, and the sequence is indicated by the positions of the 5'-end and the 3'-end where the position of the base at the 5'-end of the sequence of SEQ ID No. 1 in human REST pre-mRNA is 1 and the number of bases toward the 3'-end side is regarded as +(positive). Note that, when the number of bases outside the base at the 5'-end or the 3'-end of the sequence of SEQ ID No. 1 is expressed by a value with a −(negative) sign, and a negative value alone indicates the number of bases from the 5'-end, whereas a negative value with (3') added thereto indicates the number of bases from the 3' -end.):

(SEQ ID No. 3)
aatggtatccataccca
[+1/+18]

(SEQ ID No. 4)
accaaatggtatccatac
[+5/+22]

(SEQ ID No. 5)
taaatattaccaaatggt
[+13/+30]

(SEQ ID No. 6)
agtaaatattaccaaatg
[+15/+32]

(SEQ ID No. 7)
ctctagtaaatattacca
[+19/+36]

(SEQ ID No. 8)
cacactctagtaaatatt
[+23/+40]

(SEQ ID No. 9)
agatcacactctagtaaa
[+27/+44]

(SEQ ID No. 10)
atctagatcacactctag
[+31/+48]

-continued

```
                         (SEQ ID No. 11)
acccatctagatcacact
[+35/-2(3')]

                         (SEQ ID No. 40)
atcacactctagtaaatatt
[+23/+42]

                         (SEQ ID No. 41)
cacactctagtaaatattac
[+21/+40]

                         (SEQ ID No. 42)
cactctagtaaatatt
[+23/+38]

                         (SEQ ID No. 43)
cacactctagtaaata
[+25/+40]

                         (SEQ ID No. 44)
ctagatcacactctagtaaa
[+27/+46]

                         (SEQ ID No. 45)
agatcacactctagtaaata
[+25/+44]

                         (SEQ ID No. 46)
atcacactctagtaaa
[+27/+42]

                         (SEQ ID No. 47)
agatcacactctagta
[+29/+44]

                         (SEQ ID No. 48)
agatcacactctagtaaatatt
[+23/+44]

                         (SEQ ID No. 49)
gatcacactctagtaaat
[+26/+43]
```

One to several bases (e.g., two or three bases) may be added or deleted to/from the 5'-end and/or the 3'-end of the above sequence as long as the activity of inducing N-exon skipping in REST processing is exhibited. The added base can be a base that is complementary to a base of the sequence represented by SEQ ID No. 2 (representing a base sequence of a region that is adjacent to the target region) that is adjacent to the target region (SEQ ID No. 1) of the sequence to which the base is added.

The oligonucleotide according to the present invention encompasses oligonucleotides containing natural DNA (unmodified oligonucleotides) and oligonucleotides containing chemically modified DNA Such modifications may alter the activity of the oligonucleotide, e.g., increase affinity for target nucleic acids, or increase resistance to nucleases. Increasing the affinity of the oligonucleotide for the targets may allow the use of shorter oligonucleotides.

The oligonucleotide according to the present invention may contain at least one sugar-modified nucleoside at any position. When the oligonucleotide contains such a sugar-modified nucleoside, the percentage of the number of sugar-modified nucleotides to all of the nucleosides constituting the oligonucleotide is, for example, 30% or more, preferably 40% or more, and more preferably 50% or more. This sugar-modified nucleoside has a bridging moiety as described later between the 2'-position and the 4'-position of the sugar ring.

In an embodiment, the oligonucleotide according to the present invention contains, as a sugar-modified nucleoside, at least one nucleoside structure represented by a formula (I) below:

[Chemical Formula 9]

(1)

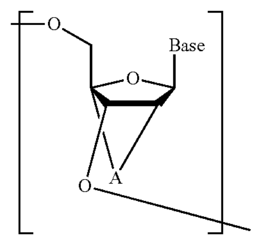

where

Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, A represents a divalent group represented by the following formulae,

[Chemical Formula 10]

(a-1)

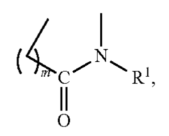

(a-2)

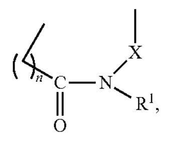

(b-1)

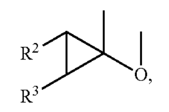

(c-1)

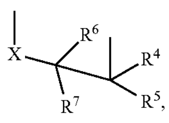

(c-2)

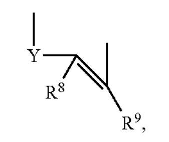

-continued (d-1)

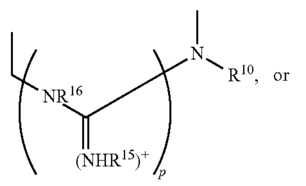

$R^{10}$, or (e-1)

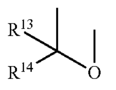

$R^1$ represents a hydrogen atom, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the α group and may have a heteroatom, an aralkyl group with an aryl moiety having 3 to 12 carbon atoms that may have any one or more substituents selected from the α group and may have a heteroatom, or an amino group protecting group for nucleic acid synthesis;

$R^2$ and $R^3$ each independently represent a hydrogen atom; an alkyl group having 1 to 7 carbon atoms that may form a branch or a ring and may have undergone substitution by an aryl group having 3 to 12 carbon atoms that may have a heteroatom; or an aralkyl group with an aryl moiety having 3 to 12 carbon atoms that may have a heteroatom; or $R^2$ and $R^3$ together represent $-(CH_2)_q-$, where q is an integer of 2 to 5;

$R^4$ and $R^5$ each independently represent one selected from the group consisting of a hydrogen atom; a hydroxy group; an alkyl group having 1 to 7 carbon atoms that may form a branch or a ring; an alkoxy group having 1 to 7 carbon atoms that may form a branch or a ring; an amino group; and an amino group protected by a protecting group for nucleic acid synthesis, alternatively, $R^4$ and $R^5$ together represent $=C(R^{11})R^{12}$, where $R^{11}$ and $R^{12}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a linear or branched alkoxy group having 1 to 6 carbon atoms, a linear or branched alkylthio group having 1 to 6 carbon atoms, a cyanoalkoxy group having 1 to 6 carbon atoms, or a linear or branched alkylamino group having 1 to 6 carbon atoms;

$R^6$ and $R^7$ each independently represent a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^8$ represents a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^9$ represents a hydrogen atom, a hydroxy group, an alkyl group having 1 to 7 carbon atoms that may form a branch or a ring, an alkoxy group having 1 to 7 carbon atoms that may form a branch or a ring, an amino group, or an amino group protected by a protecting group for nucleic acid synthesis;

$R^{10}$ represents a hydrogen atom, an alkyl group having 1 to 7 carbon atoms that may form a branch or a ring, an amino group protecting group, or the following

[Chemical Formula 11]

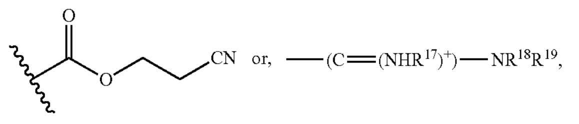

or, $-(C{=}(NHR^{17})^+)-NR^{18}R^{19}$, where $R^{17}$, $R^{18}$, and $R^{19}$ each independently represent a hydrogen atom, an alkyl group having 1 to 7 carbon atoms that may form a branch or a ring, an amino group protecting group, or the following;

[Chemical Formula 12]

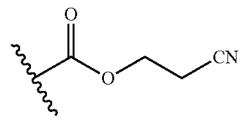

$R^{13}$ and $R^{14}$ each independently represent one selected from the group consisting of a hydrogen atom; a hydroxy group; an alkyl group having 1 to 7 carbon atoms that may form a branch or a ring; an alkoxy group having 1 to 7 carbon atoms that may form a branch or a ring; an amino group; and an amino group protected by a protecting group for nucleic acid synthesis;

m is an integer of 0 to 2; and n is an integer of 0 to 1;

when $R^{10}$ represents a hydrogen atom, an alkyl group having 1 to 7 carbon atoms that may form a branch or a ring, an amino group protecting group, or the following,

[Chemical Formula 13]

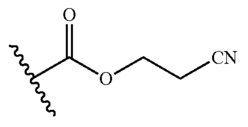

p is 1, and $R^{15}$ and $R^{16}$ each independently represent a hydrogen atom, an alkyl group having 1 to 7 carbon atoms that may form a branch or a ring, an amino group protecting group, or the following,

[Chemical Formula 14]

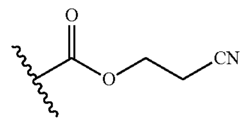

alternatively, $R^{10}$ represents $-(C{=}(NHR^{17})^+)-NR^{18}R^{19}$, where $R^{17}$, $R^{18}$, and $R^{19}$ each independently represent a hydrogen atom, an alkyl group having 1 to 7 carbon atoms that may form a branch or a ring, an amino group protecting group, or the following,

[Chemical Formula 15]

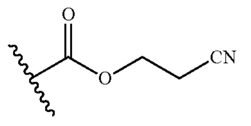

p is 0;

X is an oxygen atom, a sulfur atom, or an amino group; and

Y is an oxygen atom or a sulfur atom.

In an embodiment, the nucleoside structure represented by the formula (I) above is a structure represented by the following:

[Chemical Formula 16]

(I-1)

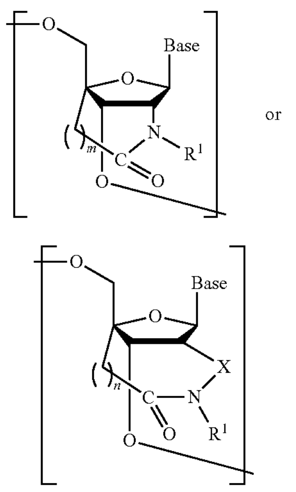

or (I-2)

where Base, $R^1$, X, m, and n in the formulae (I-1) and (I-2) are the same as described above for the formula (I). An amide (—CONR$^1$—) is introduced into a bridge between the 2'-position and the 4'-position, and such a nucleoside structure is also referred to as an amide-bridged nucleic acid, amide BNA (Bridged Nucleic Acid), or AmNA.

In the formulae (I-1) and (I-2), $R^1$ represents a hydrogen atom, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the α0 group and may have a heteroatom, or an aralkyl group with an aryl moiety having 3 to 12 carbon atoms that may have any one or more substituents selected from the α group and may have a heteroatom. More favorably, $R^1$ represents a hydrogen atom, a methyl group, an ethyl group, an n-propyl group, an isopropyl group, a phenyl group, or a benzyl group, and $R^1$ is even more preferably a hydrogen atom or a methyl group.

In the formula (I-1), m is an integer of 0 to 2; and in the formula (I-2), n is an integer of 0 to 1. That is, a ring containing the 2'-position, 3'-position, 4'-position, and the bridging moiety may constitute a 5-membered ring to a 7-membered ring.

In the formula (I-2), X is an oxygen atom, a sulfur atom, an amino group, or a methylene group. Favorably, X is an oxygen atom or an amino group. Note that, when X is an amino group or a methylene group, X may be substituted by a lower alkyl group.

In an embodiment, the nucleoside structure represented by the formula (I) is a structure represented by the formula (I-1), and in the formula (I-1), m is 0, and $R^1$ is a hydrogen atom, a methyl group, an ethyl group, an n-propyl group, an isopropyl group, a phenyl group, or a benzyl group.

In the compounds represented by the formulae (I-1) and (I-2), an amide bond is formed between the amino group at the 2'-position of the sugar moiety and the carbonyl group extending from the 4'-position. Because the nucleoside structure has an amide bond with little structural fluctuation and high hydrophilicity in this manner, the structure of the sugar moiety of the nucleoside is immobilized through bridging.

Examples of the nucleoside structure represented by the formula (I) above include the formulae (I-3) to (I-7) below, for example, in addition to the formulae (I-1) and (I-2):

[Chemical Formula 17]

(I-3)

(I-4)

(I-5)

(I-6)

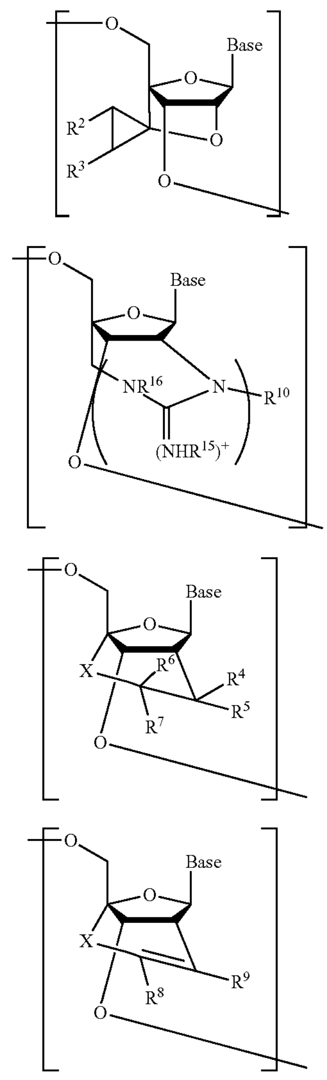

-continued (I-7)

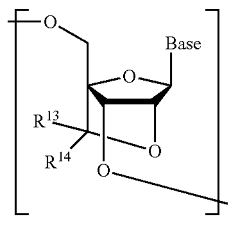

where Base, $R^2$, $R^3$, $R^4$, $R^5$, $R^6$, $R^7$, $R^8$, $R^9$, $R^{10}$, $R^{13}$, $R^{14}$, $R^{15}$, $R^{16}$, and p are the same as described above for the formula (I). The formula (I-7) corresponds to a nucleoside structure that is referred to as 2',4'-BNA or LNA (Locked Nucleic Acid) (also referred to as "2',4'-BNA/LNA" or "LNA" in this specification) (as an example, both $R^{13}$ and $R^{14}$ are hydrogen atoms). The formula (I-3) has a structure in which a spirocyclopropane group is introduced at the 6'-position of the bridging moiety of 2',4'-BNA/LNA, and is also referred to as a spirocyclopropane bridged nucleic acid (scpBNA). The formula (I-4) has a structure in which guanidine is introduced into the bridging moiety of 2',4'-BNA/LNA, and is also referred to as guanidine bridged nucleic acid (GuNA). Note that the formula (I-4) encompasses the following formulae (I-4-1) (when p=0 holds true) and (I-4-2) (when p=1 holds true):

[Chemical Formula 18]

(I-4-1)

(I-4-2)

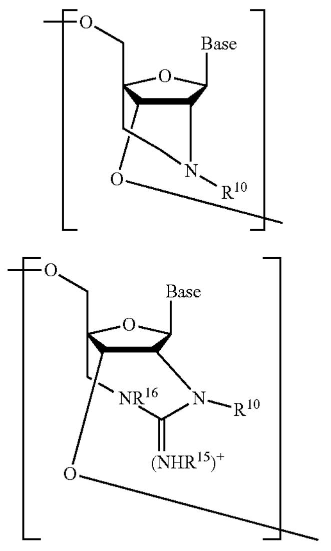

"Base" mentioned above is a purine base (i.e., a purin-9-yl group) or a pyrimidine base (i.e., a 2-oxo-1,2-dihydropyrimidin-1-yl group). These bases may have any one or more substituents selected from the α group consisting of a hydroxy group, linear alkyl groups having 1 to 6 carbon atoms, linear alkoxy groups having 1 to 6 carbon atoms, a mercapto group, linear alkylthio groups having 1 to 6 carbon atoms, an amino group, linear alkylamino groups having 1 to 6 carbon atoms, and halogen atoms.

Specific examples of the "Base" above include an adeninyl group, a guaninyl group, a cytosinyl group, an uracilyl group, a thyminyl group, a 6-aminopurin-9-yl group, a 2,6-diaminopurin-9-yl group, a 2-amino-6-chloropurin-9-yl group, a 2-amino-6-fluoropurin-9-yl group, a 2-amino-6-bromopurin-9-yl group, a 2-amino-6-hydroxypurin-9-yl group, a 6-amino-2-methoxypurin-9-yl group, a 6-amino-2-chloropurin-9-yl group, a 6-amino-2-fluoropurin-9-yl group, a 2,6-dimethoxypurin-9-yl group, a 2, 6-dichloropurin-9-yl group, a 6-mercaptopurin-9-yl group, a 2-oxo-4-amino-1,2 -dihydropyrimidin-1-yl group, a 4-amino-2-oxo-5-fluoro-1, 2-dihydropyrimidin-1-yl group, a 4-amino-2-oxo-5-chloro-1,2-dihydropyrimidin-1-yl group, a 2-oxo -4-methoxy-1,2-dihydropyrimidin-1-yl group, a 2-oxo -4-mercapto-1,2-dihydropyrimidin-1-yl group, a 2-oxo-4-hydroxy-1,2-dihydropyrimidin-1-yl group, a 2-oxo-4-hydroxy-5-methyl-1,2-dihydropyrimidin-1-yl group, and a 4-amino-5-methyl-2-oxo-1,2-dihydropyrimidin-1-yl group.

In particular, from the viewpoint of introducing "Bases" into an oligonucleotide therapeutic, the "Bases" are preferably groups (i.e., a thyminyl group, a cytosinyl group, an adeninyl group, a guaninyl group, a 5-methylcytosinyl group, and an uracilyl group) represented by structural formulae below:

[Chemical Formula 19]

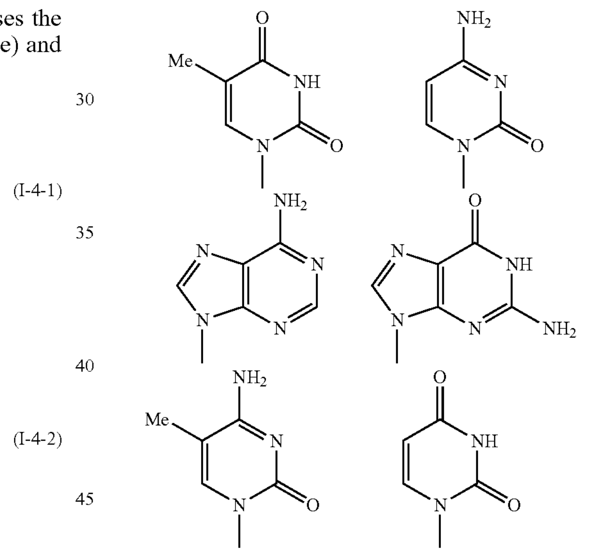

as well as a 2-oxo-4-hydroxy-5-methyl-1,2-dihydropyrimidin-1-yl group, a 2-oxo-4-amino-1,2-dihydropyrimidin-1-yl group, a 6-aminopurin-9-yl group, a 2-amino-6-hydroxypurin-9-yl group, a 4-amino -5-methyl-2-oxo-1,2-dihydropyrimidin-1-yl group, and a 2-oxo-4-hydroxy-1,2-dihydropyrimidin-1-yl group. In particular, a 2-oxo-4-hydroxy-5-methyl-1,2-dihydropyrimidin-1-yl group and a thyminyl group are favorable. It is preferable that a hydroxy group and an amino group are protected by a protecting group during oligonucleotide synthesis.

Note that, in an embodiment, when the oligonucleotide according to the present invention has a nucleoside structure represented by the formula (I-4), the formula (I-4-1), or the formula (I-4-2) as a sugar-modified nucleoside, the nucleoside structure represented by the formula (I-4), (I-4-1), or (I-4-2) is kept electrically neutral by a pharmaceutically acceptable anion (which can be represented by $Z^{31}$ , for example) that is not represented in the formula (I-4), the formula (I-4-1), or the formula (I-4-2). Examples of such anions include halide ions (e.g., chloride ion) and phosphate ions.

An oligonucleotide that contains at least one sugar-modified nucleoside structure as described above can be synthesized using a sugar-modified nucleoside compound, for example, and using methods such as those described in WO 2011/052436, JP 2014-043462A, WO 2014/046212, and WO 2015/125783, for example.

Examples of the sugar-modified nucleoside compound include compounds represented by a formula (II) below and salts thereof:

[Chemical Formula 20]

(11)

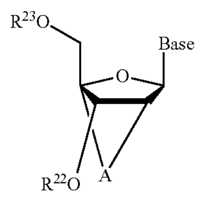

where

Base represents a purin-9-yl group that may have any one or more substituents selected from an α group, or a 2-oxo-1,2-dihydropyrimidin-1-yl group that may have any one or more substituents selected from the α group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, A represents a divalent group represented by the following formulae:

(a-1)

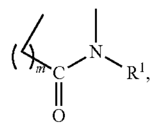

(a-2)

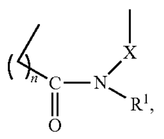

(b-1)

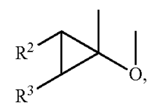

(c-1)

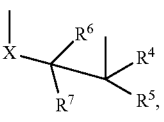

-continued (c-2)

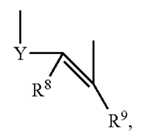

(d-1)

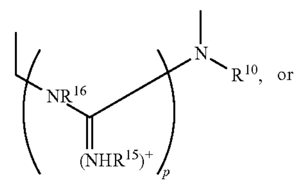

or (e-1)

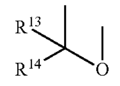

$R^1$ represents a hydrogen atom, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the α group and may have a heteroatom, an aralkyl group with an aryl moiety having 3 to 12 carbon atoms that may have any one or more substituents selected from the α group and may have a heteroatom, or an amino group protecting group for nucleic acid synthesis;

$R^2$ and $R^3$ each independently represent a hydrogen atom; an alkyl group having 1 to 7 carbon atoms that may form a branch or a ring and may have undergone substitution by an aryl group having 3 to 12 carbon atoms that may have a heteroatom; or an aralkyl group with an aryl moiety having 3 to 12 carbon atoms that may have a heteroatom; or $R^2$ and $R^3$ together represent $-(CH_2)_q-$, where q is an integer of 2 to 5;

$R^4$ and $R^5$ each independently represent one selected from the group consisting of a hydrogen atom; a hydroxy group; an alkyl group having 1 to 7 carbon atoms that may form a branch or a ring; an alkoxy group having 1 to 7 carbon atoms that may form a branch or a ring; an amino group; and an amino group protected by a protecting group for nucleic acid synthesis, alternatively, $R^4$ and $R^5$ together represent $=C(R^{11})R^{12}$, where $R^{11}$ and $R^{12}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a linear or branched alkoxy group having 1 to 6 carbon atoms, a linear or branched alkylthio group having 1 to 6 carbon atoms, a cyanoalkoxy group having 1 to 6 carbon atoms, or a linear or branched alkylamino group having 1 to 6 carbon atoms;

$R^6$ and $R^7$ each independently represent a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^8$ represents a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^9$ represents a hydrogen atom, a hydroxy group, an alkyl group having 1 to 7 carbon atoms that may form a branch or a ring, an alkoxy group having 1 to 7 carbon atoms that may form a branch or a ring, an amino group, or an amino group protected by a protecting group for nucleic acid synthesis;

$R^{10}$ represents a hydrogen atom, an alkyl group having 1 to 7 carbon atoms that may form a branch or a ring, an amino group protecting group, or the following,

[Chemical Formula 22]

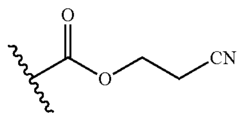

or, —(C═(NHR$^{17}$)$^+$)—NR$^{18}$R$^{19}$, where $R^{17}$, $R^{18}$, and $R^{19}$ each independently represent a hydrogen atom, an alkyl group having 1 to 7 carbon atoms that may form a branch or a ring, an amino group protecting group, or the following;

[Chemical Formula 23]

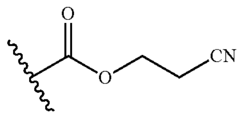

$R^{13}$ and $R^{14}$ each independently represent one selected from the group consisting of a hydrogen atom; a hydroxy group; an alkyl group having 1 to 7 carbon atoms that may form a branch or a ring; an alkoxy group having 1 to 7 carbon atoms that may form a branch or a ring; an amino group; and an amino group protected by a protecting group for nucleic acid synthesis;

m is an integer of 0 to 2; and n is an integer of 0 to 1;

when $R^{10}$ represents a hydrogen atom, an alkyl group having 1 to 7 carbon atoms that may form a branch or a ring, an amino group protecting group, or the following,

[Chemical Formula 24]

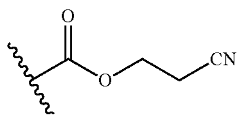

p is 1, and $R^{15}$ and $R^{16}$ each independently represent a hydrogen atom, an alkyl group having 1 to 7 carbon atoms that may form a branch or a ring, an amino group protecting group, or the following,

[Chemical Formula 25]

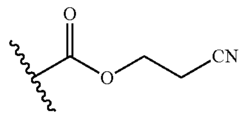

alternatively, when $R^{10}$ represents —(C═(NHR$^{17}$)$^+$)—NR$^{18}$R$^{19}$, where $R^{17}$, $R^{18}$, and $R^{19}$ each independently represent a hydrogen atom, an alkyl group having 1 to 7 carbon atoms that may form a branch or a ring, an amino group protecting group, or the following,

[Chemical Formula 26]

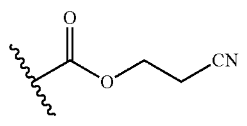

p is 0;

X is an oxygen atom, a sulfur atom, or an amino group; and

Y is an oxygen atom or a sulfur atom; and $R^{22}$ and $R^{23}$ each independently represent a hydrogen atom, a hydroxy group protecting group for nucleic acid synthesis, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the α group and may have a heteroatom, an aralkyl group with an aryl moiety having 3 to 12 carbon atoms that may have any one or more substituents selected from the α group and may have a heteroatom, an acyl group that may have any one or more substituents selected from the α group, a silyl group that may have any one or more substituents selected from the α0 group, a phosphate group that may have any one or more substituents selected from the a group, a phosphate group protected by a protecting group for nucleic acid synthesis, or —P(R$^{24}$)R$^{25}$, where $R^{24}$ and $R^{25}$ each independently represent a hydroxy group, a hydroxy group protected by a protecting group for nucleic acid synthesis, a mercapto group, a mercapto group protected by a protecting group for nucleic acid synthesis, an amino group, an alkoxy group having 1 to 5 carbon atoms, an alkylthio group having 1 to 5 carbon atoms, a cyanoalkoxy group having 1 to 6 carbon atoms, or a dialkylamino group that has undergone substitution by an alkyl group having 1 to 6 carbon atoms.

A sugar-modified nucleotide can be easily prepared using the sugar-modified nucleosides described above. Triphosphorylation can be easily performed in accordance with the method described in M. Kuwahara et al., Nucleic Acids Res., 2008, vol.36, No.13, pp.4257-65, for example.

The nucleotide modifications known in the art other than the above-mentioned modifications to sugar can also be used. A modification to phosphate and a modification to a nucleobase are known as the nucleotide modifications. Such modifications to a nucleic acid can be performed based on methods known in the art.

Examples of the modification to phosphate include a phosphodiester bond included in a native nucleic acid, S-oligo(phosphorothioate), D-oligo(phosphodiester), M-oligo(methylphosphonate), and boranop hosp hate. S-oligo(phosphorothioate) includes a PS backbone in which an oxygen atom in the phosphate group moiety of the phosphodiester bond between nucleosides is substituted by a sulfur atom. This modification is introduced into an oligonucleotide in accordance with a known method. An antisense oligonucleotide that includes this modification at one or more positions in the oligonucleotide is referred to as an 5-oligo type (phosphorothioate type).

Examples of the modification to a nucleobase include 5-methylcytosine, 5-hydroxymethylcytosine, and 5-propynylcytosine.

There is no particular limitation on the positions and number of the sugar-modified nucleosides in the oligonucleotide of the present invention, and the oligonucleotide can be designed as appropriate depending on the purpose. Two or more sugar-modified nucleosides may be the same or different, for example. Oligonucleotides can be designed using sugar-modified nucleosides and unmodified nucleosides such that sugar-modified nucleosides and unmodified nucleosides are arranged alternately. It is preferable that, with regard to the oligonucleotide according to the present invention, a sugar-modified nucleoside is arranged next to a region constituted by 1 to 3 unmodified nucleoside residues. As a result, RNA to which an oligonucleotide binds is unlikely to be cleaved by RNase H.

In an embodiment, the nucleoside structure represented by the formula (I) above is the following:

[Chemical Formula 27]

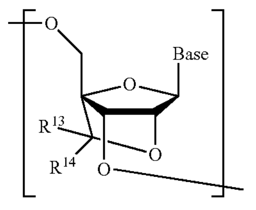

where both $R^{13}$ and $R^{14}$ are hydrogen atoms; or

[Chemical Formula 28]

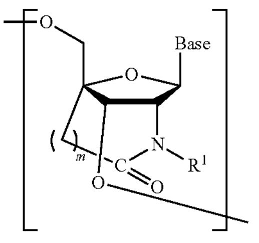

where m is 0, and $R^1$ represents a hydrogen atom, a methyl group, an ethyl group, an n-propyl group, an isopropyl group, a phenyl group, or a benzyl group.

In an embodiment, the oligonucleotide according to the present invention is an oligonucleotide that includes a base sequence represented by any one of the base sequences of SEQ ID Nos. 3 to 11 and SEQ ID Nos. 40 to 49 described above, and in which at least one of the bases is the above sugar-modified nucleoside. Examples of such an oligonucleotide include the following:

AmNA[+1/+18]

(SEQ ID No. 18)
A(Y)^a^T(Y)^g^G(Y)^t^A(Y)^t^5(Y)^t^A(Y)^t^A(Y)^t^5(Y)^t^5(Y)^a

AmNA[+5/+22]

(SEQ ID No. 19)
A(Y)^c^5(Y)^a^A(Y)^a^T(Y)^g^G(Y)^t^A(Y)^t^5(Y)^c^A(Y)^t^A(Y)^c

AmNA[+13/+30]

(SEQ ID No. 20)
T(Y)^a^A(Y)^a^T(Y)^a^T(Y)^t^A(Y)^c^5(Y)^a^A(Y)^a^T(Y)^g^G(Y)^t

AmNA[+15/+32]

(SEQ ID No. 21)
A(Y)^g^T(Y)^a^A(Y)^a^T(Y)^a^T(Y)^t^A(Y)^c^5(Y)^a^A(Y)^a^T(Y)^g

AmNA[+19/+36]

(SEQ ID No. 22)
5(Y)^^5(Y)^t^A(Y)^g^T(Y)^a^A(Y)^a^T(Y)^a^T(Y)^t^A(Y)^c^5(Y)^a

AmNA[+23/+40]

(SEQ ID No. 23)
5(Y)^a^5(Y)^a^5(Y)^t^5(Y)^t^A(Y)^t^T(Y)^a^A(Y)^a^T(Y)^a^T(Y)^t

AmNA[+27/+44]

(SEQ ID No. 24)
A(Y)^g^A(Y)^t^5(Y)^a^5(Y)^a^5(Y)^t^5(Y)^t^A(Y)^t^T(Y)^a^A(Y)^a

AmNA[+31/+48]

(SEQ ID No. 25)
A(Y)^t^5(Y)^t^A(Y)^g^A(Y)^t^5(Y)^a^5(Y)^a^5(Y)^t^5(Y)^t^A(Y)^g

AmNA[+35/-2(3')]

(SEQ ID No. 26)
A(Y)^c^5(Y)^c^A(Y)^t^5(Y)^t^A(Y)^t^A(Y)^t^5(Y)^a^5(Y)^a^5(Y)^t

In the above sequences, a lowercase letter indicates DNA, and N(Y) indicates AmNA, 5(Y) indicates AmNA_mC, and ^ indicates being phosphorothioated (PS backbone).

AmNA[+23/+42]:

(SEQ ID No. 53)
A(Y)^t^5(Y)^a^5(Y)^a^5(Y)^t^5(Y)^t^A(Y)^g^T(Y)^a^A(Y)^a^T(Y)^a^T(Y)^t

AmNA[+21/+40]:

(SEQ ID No. 54)
5(Y)^a^5(Y)^a^5(Y)^t^5(Y)^t^A(Y)^g^T(Y)^a^A(Y)^a^T(Y)^a^T(Y)^t^A(Y)^c

AmNA[+23/+38]:

(SEQ ID No. 55)
5(Y)^a^5(Y)^t^5(Y)^t^A(Y)^g^T(Y)^a^A(Y)^a^T(Y)^a^T(Y)^t

-continued

AmNA[+25/+40]:

(SEQ ID No. 56)
5(Y)^a^5(Y)^a^5(Y)^t^5(Y)^t^A(Y)^g^T(Y)^a^A(Y)^a^T(Y)^a

AmNA[+27/+46]:

(SEQ ID No. 57)
5(Y)^t^A(Y)^g^A(Y)^t^5(Y)^a^5(Y)^a^5(Y)^t^5(Y)^t^A(Y)^g^T(Y)^a^A(Y)^a

AmNA[+25/+44]:

(SEQ ID No. 58)
A(Y)^g^A(Y)^t^5(Y)^a^5(Y)^a^5(Y)^t^5(Y)^t^A(Y)^g^T(Y)^a^A(Y)^a^T(Y)^a

AmNA[+27/+42]:

(SEQ ID No. 59)
A(Y)^t^5(Y)^a^5(Y)^a^5(Y)^t^5(Y)^t^A(Y)^g^T(Y)^a^A(Y)^a

AmNA[+29/+44]:

(SEQ ID No. 60)
A(Y)^g^A(Y)^t^5(Y)^a^5(Y)^a^5(Y)^t^5(Y)^t^A(Y)^g^T(Y)^a

AmNA[+23/+44]:

(SEQ ID No. 61)
A(Y)^g^A(Y)^t^5(Y)^a^5(Y)^a^5(Y)^t^5(Y)^t^A(Y)^g^T(Y)^a^A(Y)^a^T(Y)^a^T(Y)^t

AmNA[+26/+43]:

(SEQ ID No. 62)
G(Y)^a^T(Y)^c^A(Y)^c^A(Y)^c^T(Y)^c^T(Y)^a^G(Y)^t^A(Y)^a^A(Y)^t

AmNA[+27/+44]_1/3:

(SEQ ID No. 63)
A(Y)^g^a^T(Y)^c^a^5(Y)^a^c^T(Y)^c^t^A(Y)^g^t^A(Y)^a^a

In the above sequences, a lowercase letter indicates DNA, and N(Y) indicates AmNA, 5(Y) indicates AmNA_mC, and ^ indicates being phosphorothioated (PS backbone).

Also, in the names of the above sequences, numeral values in the square brackets [ ] indicate a sequence targeted by that oligonucleotide, and the sequence is expressed by the positions of both ends where the position of the base at the 5'-end of the sequence of SEQ ID No. 1 in human REST pre-mRNA is 1, and the number of bases toward the 3'-end is regarded as + (positive). Note that, when the number of bases outside the base at the 5'-end or the 3'-end of the sequence of SEQ ID No. 1 is expressed by a value with a − (negative) sign, and a negative value alone indicates the number of bases from the 5'-end, whereas a negative value with (3') added thereto indicates the number of bases from the 3'-end.

The oligonucleotide according to the present invention can be synthesized using a sugar-modified nucleoside and a natural nucleoside as described above and using an ordinary method, and can be easily synthesized using a commercially available automated polynucleotide synthesizer (e.g., manufactured by Applied Biosystems, GeneDesign, Inc. or the like), for example. Examples of a synthesis method includes solid-phase synthesis using a phosphoramidite and solid-phase synthesis using hydrogen phosphonate. Synthesis methods are disclosed in Tetrahedron Letters, 1981, vol. 22. pp.1859-1862, WO 2011/052436, WO 2014/046212, WO 2015/125783, and the like, for example.

Pharmaceutical Composition

A pharmaceutical composition according to the present invention contains the above oligonucleotide or a pharmacologically acceptable salt thereof. The pharmaceutical composition according to the present invention is useful for treating or preventing diseases associated with REST processing (splicing), for example. Examples of target diseases of the pharmaceutical composition according to the present invention include cancer diseases and heart failure. Examples of the cancer diseases associated with REST processing include SRRM4-mediated cancers (e.g., small cell lung cancer, prostate cancer (e.g., castration-resistant prostate cancer (CRPC)), breast cancer). Such cancer diseases may originate from neuroendocrine cells. Further, the present invention encompasses a cancer therapeutic agent containing the above oligonucleotide or a pharmacologically acceptable salt thereof. Also, the present invention encompasses a heart failure therapeutic agent containing the above oligonucleotide or a pharmacologically acceptable salt thereof.

Any administration method and formulation known in the art can be used for a method for administrating a pharmaceutical composition, a cancer therapeutic agent, or a heart failure therapeutic agent according to the present invention (also collectively referred to as a "pharmaceutical composition" and the like hereinafter), and a formulation thereof.

The pharmaceutical composition and the like according to the present invention can be administrated using various methods depending on topical or systemic treatment or a region to be treated. Examples of the administration method include topical administration (including ocular instillation, intravaginal administration, intrarectal administration, intranasal administration, and percutaneous administration), oral administration, and parenteral administration. Examples of parenteral administration include intravenous injection, intravenous instillation, subcutaneous transfusion, intraabdominal transfusion, intramuscular transfusion, pulmonary administration via the airway through aspiration or inhalation.

The pharmaceutical composition and the like of the present invention can be topically administrated using formulations such as a percutaneous patch, ointment, lotion, cream, gel, drops, suppository, spray, liquid medicine, and powder medicine.

Examples of compositions for oral administration include powder medicine, granular medicine, a suspension or solution obtained through dissolution in water or a non-aqueous medium, a capsule, powdered medicine, and a tablet.

Examples of compositions for parenteral administration include sterile aqueous solutions containing a buffer, a diluent, and other appropriate additives.

The pharmaceutical composition and the like of the present invention can be obtained by mixing an effective dose of the oligonucleotide mentioned above or a pharmacologically acceptable salt thereof, and various pharmaceutical additives suitable for the dosage form, such as a vehicle, a binding agent, a moistening agent, a disintegrating agent, a lubricant, and a diluent. In the case of an injection, it is sufficient that a formulation is prepared by performing sterilization together with an appropriate carrier.

The present invention provides a method for inducing N-exon skipping during REST processing. The present invention also provides a method for treating or preventing diseases associated with REST processing. In an embodiment, these methods are used for treating or preventing the above-described target diseases. These methods include a step of administrating the oligonucleotide mentioned above or a pharmacologically acceptable salt thereof to an individual. The "individual" is preferably a mammal, more preferably a human, monkey, dog, cat, rat, or mouse, and even more preferably a human. In these methods, there is no limitation on the administration method and dosage form as long as an effective dose of the oligonucleotide of the present invention is administrated. Although the effective administration dose depends on the individual to which the oligonucleotide is to be administrated, the effective administration dose can be determined as desired in accordance with the sex, age, weight, symptom and the like of the individual, and the method, route, frequency and the like of the administration. The administration methods and the like are as described above.

EXAMPLES

Hereinafter, the present invention will be described by way of examples, but the present invention is not limited thereto.

Example 1: Antisense Oligonucleotide Synthesis

An oligonucleotide relating to the present invention was synthesized using the method described in Tetrahedron Letters 22, 1859-1862 (1981), WO 2011/052436, and the like. An oligonucleotide containing amide BNA (AmNA) represented by a formula below was synthesized with reference to the method described in WO 2011/052436 based on a design in Example 1.

[Chemical Formula 29]

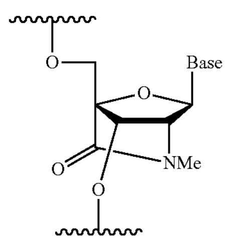

where Base is a 5-methylcytosinyl group, a thyminyl group, an adeninyl group, or a guaninyl group, and Me is a methyl group.

An 18-mer oligonucleotide containing an amide BNA (AmNA) was synthesized on a 0.2 nmol scale using an automated polynucleotide synthesizer (type nS-8 manufactured by GeneDesign, Inc.). The strand length was elongated in accordance with a standard phosphoroamidite protocol (solid support: CPG resin; DDT (3H-1,2-benzodithiole-3-one,1,1-dioxide) or the like was used in sulfurization for forming a phosphorothioated (PS) backbone), and thus an oligonucleotide in which a hydroxy group at the 5'-end was protected by a DMTr (dimethoxytrityl) group and the 3'-end was held in the solid phase was obtained. Next, the DMTr group was removed through acid treatment, and base treatment was performed to remove target products from the solid support. After neutralization using dilute acid, the solvent was distilled off, and then the resultant crude product was purified using gel filtration column chromatography and reversed phase HPLC. The target products were thus obtained.

The structure of the bridging moiety of the AmNA used in this example and the purities and structures of the obtained oligonucleotides were confirmed using HPLC and MALDI-TOF-MS (manufactured by BRUKER DALTONICS).

Example 2: Design of Antisense Oligonucleotide for Human REST Pre-mRNA

Antisense oligonucleotides targeting the pre-mRNA (precursor mRNA) of human REST gene (NCBI Reference Sequence: NG_029447.1 Homo sapiens RE1 silencing transcription factor (REST), ReSeqGene on chromosome 4.) were designed.

In order to select target regions, the reverse sequences (CG, GGA, and GCA) of CG, TCC, and TGC were excluded since CG, TCC, and TGC are toxic in an antisense strand. Then, regions such as a loop structure that are easy for an antisense oligonucleotide to reach were selected based on the secondary structure prediction using mfold (mfold: http://unafold.rna.albany.edu/?q=mfold). Next, regions where homology between human and mouse REST pre-mRNAs is high were mainly selected using Blast (BLAST: https://blast.ncbi.nlm.nih.gov/Blast.cgi?PAGE_TYPE=BlastSearch) so that the evaluation results obtained using mice could be applied to humans. In this manner, eighteen candidate sequences were selected.

Oligonucleotides having base sequences complementary to the candidate sequences selected as mentioned above were designed as antisense oligonucleotides. Each of the antisense oligonucleotides had a length of 18 bases and was designed such that artificial nucleic acid (AmNA) containing a sugar-modified nucleoside was provided at the 5' end, and artificial nucleic acids and DNA were arranged alternately.

Also, in particular, the sequence length was changed, the positions of AmNAs and natural nucleic acids were switched, and/or the number of AmNAs introduced was changed based on two types of candidate sequences (AmNA[+23/+40] and AmNA[+27/+44]) with high activity of inducing N-exon skipping, and therefore eleven new candidate sequences were selected.

The following indicates the sequences of the designed antisense oligonucleotides in the direction from 5' toward 3' (5'→3'):

```
AmNA[-44/-27]:
                                      (SEQ ID No. 12)
A(Y)^a^A(Y)^c^G(Y)^g^A(Y)^a^A(Y)^t^T(Y)^
g^A(Y)^c^A(Y)^t^T(Y)^t

AmNA[-32/-15]:
                                      (SEQ ID No. 13)
T(Y)^g^5(Y)^a^T(Y)^a^G(Y)^t^A(Y)^g^A(Y)^
a^A(Y)^a^A(Y)^c^G(Y)^g

AmNA[-24/-7]:
                                      (SEQ ID No. 14)
5(Y)^a^A(Y)^t^G(Y)^g^A(Y)^a^T(Y)^g^5(Y)^
a^T(Y)^a^G(Y)^t^A(Y)^g
```

-continued

AmNA[-20/-3]:
(SEQ ID No. 15)
G(Y)^g^T(Y)^c^5(Y)^a^A(Y)^t^G(Y)^g^A(Y)^a^T(Y)^g^5(Y)^a^T(Y)^a

AmNA[-18/-1]:
(SEQ ID No. 16)
5(Y)^t^G(Y)^g^T(Y)^c^5(Y)^a^A(Y)^t^G(Y)^g^A(Y)^a^T(Y)^g^5(Y)^a

AmNA[-8/+10]:
(SEQ ID No. 17)
5(Y)^c^A(Y)^t^A(Y)^c^5(Y)^c^5(Y)^a^5(Y)^t^G(Y)^g^T(Y)^c^5(Y)^a

AmNA[+1/+18]:
(SEQ ID No. 18)
A(Y)^a^T(Y)^g^G(Y)^t^A(Y)^t^5(Y)^c^A(Y)^t^A(Y)^c^5(Y)^c^5(Y)^a

AmNA[+5/+22]:
(SEQ ID No. 19)
A(Y)^c^5(Y)^a^A(Y)^a^T(Y)^g^G(Y)^t^A(Y)^t^5(Y)^c^A(Y)^t^A(Y)^c

AmNA[+13/+30]:
(SEQ ID No. 20)
T(Y)^a^A(Y)^a^T(Y)^a^T(Y)^t^A(Y)^c^5(Y)^a^A(Y)^a^T(Y)^g^G(Y)^t

AmNA[+15/+32]:
(SEQ ID No. 21)
A(Y)^g^T(Y)^a^A(Y)^a^T(Y)^a^T(Y)^t^A(Y)^c^5(Y)^a^A(Y)^a^T(Y)^g

AmNA[+19/+36]:
(SEQ ID No. 22)
5(Y)^t^5(Y)^t^A(Y)^a^T(Y)^a^A(Y)^a^T(Y)^a^T(Y)^t^A(Y)^c^5(Y)^a

AmNA[+23/+40]:
(SEQ ID No. 23)
5(Y)^a^5(Y)^a^5(Y)^t^5(Y)^t^A(Y)^g^T(Y)^a^A(Y)^a^T(Y)^a^T(Y)^t

AmNA[+27/+44]:
(SEQ ID No. 24)
A(Y)^g^A(Y)^t^5(Y)^a^5(Y)^a^5(Y)^t^5(Y)^t^A(Y)^g^T(Y)^a^A(Y)^a

AmNA[+31/+48]:
(SEQ ID No. 25)
A(Y)^t^5(Y)^t^A(Y)^g^A(Y)^t^5(Y)^a^5(Y)^a^5(Y)^a^5(Y)^a^A(Y)^g

AmNA[+35/-2(3')]:
(SEQ ID No. 26)
A(Y)^c^5(Y)^c^A(Y)^t^5(Y)^t^A(Y)^g^A(Y)^t^5(Y)^a^5(Y)^a^5(Y)^t

AmNA[+43/-10(3')]:
(SEQ ID No. 27)
G(Y)^a^A(Y)^t^A(Y)^c^A(Y)^t^A(Y)^c^5(Y)^c^A(Y)^t^5(Y)^t^A(Y)^g

AmNA[-5(3')/-22(3')]:
(SEQ ID No. 28)
T(Y)^a^5(Y)^a^T(Y)^t^5(Y)^t^A(Y)^c^5(Y)^t^G(Y)^a^A(Y)^t^A(Y)^c

AmNA[-17(3')/-34(3')]:
(SEQ ID No. 29)
G(Y)^c^A(Y)^t^A(Y)^a^G(Y)^a^G(Y)^t^A(Y)^a^T(Y)^a^5(Y)^a^T(Y)^t

AmNA[+23/+42]:
(SEQ ID No. 53)
A(Y)^t^5(Y)^a^5(Y)^a^5(Y)^t^5(Y)^t^A(Y)^g^T(Y)^a^A(Y)^a^T(Y)^a^T(Y)^t

AmNA[+21/+40]:
(SEQ ID No. 54)
5(Y)^a^5(Y)^a^5(Y)^t^5(Y)^t^A(Y)^g^T(Y)^a^A(Y)^a^T(Y)^a^T(Y)^t^A(Y)^c

AmNA[+23/+38]:
(SEQ ID No. 55)
5(Y)^a^5(Y)^t^5(Y)^t^A(Y)^g^T(Y)^a^A(Y)^a^T(Y)^a^T(Y)^t

AmNA[+25/+40]:
(SEQ ID No. 56)
5(Y)^a^5(Y)^a^5(Y)^t^5(Y)^t^A(Y)^g^T(Y)^a^A(Y)^a^T(Y)^a

AmNA[+27/+46]:
(SEQ ID No. 57)
5(Y)^t^A(Y)^g^A(Y)^t^5(Y)^a^5(Y)^a^5(Y)^t^5(Y)^t^A(Y)^g^T(Y)^a^A(Y)^a

AmNA[+25/+44]:
(SEQ ID No. 58)
A(Y)^g^A(Y)^t^5(Y)^a^5(Y)^a^5(Y)^t^5(Y)^t^A(Y)^g^T(Y)^a^A(Y)^a^T(Y)^a

AmNA[+27/+42]:
(SEQ ID No. 59)
A(Y)^t^5(Y)^a^5(Y)^a^5(Y)^t^5(Y)^t^A(Y)^g^T(Y)^a^A(Y)^a

AmNA[+29/+44]:
(SEQ ID No. 60)
A(Y)^g^A(Y)^t^5(Y)^a^5(Y)^a^5(Y)^t^5(Y)^t^A(Y)^g^T(Y)^a

AmNA[+23/+44]:
(SEQ ID No. 61)
A(Y)^g^A(Y)^t^5(Y)^a^5(Y)^a^5(Y)^t^5(Y)^t^A(Y)^g^T(Y)^a^A(Y)^a^T(Y)^a^T(Y)^t

AmNA[+26/+43]:
(SEQ ID No. 62)
G(Y)^a^T(Y)^c^A(Y)^c^A(Y)^c^T(Y)^c^T(Y)^a^G(Y)^t^A(Y)^a^A(Y)^t

AmNA[+27/+44]_1/3:
(SEQ ID No. 63)
A(Y)^g^a^T(Y)^c^a^5(Y)^a^c^T(Y)^c^t^A(Y)^g^t^A(Y)^a^a

In the above sequences, a lowercase letter indicates DNA, and N(Y) indicates AmNA, 5(Y) indicates AmNA mC, and ^ indicates being phosphorothioated (PS backbone).

Also, in the names of the above sequences, numeral values in the square brackets [ ] indicate a sequence targeted by that oligonucleotide, and the sequence is expressed by the positions of both ends where the position of the base at the 5'-end of the sequence of SEQ ID No. 1 in human REST pre-mRNA is 1, and the number of bases toward the 3'-end is regarded as + (positive). Note that, when the number of bases outside the base at the 5'-end or the 3'-end of the sequence of SEQ ID No. 1 is expressed by a value with a −(negative) sign, and a negative value alone indicates the number of bases from the 5'-end, whereas a negative value with (3') added thereto indicates the number of bases from the 3'-end.

Note that the term "phosphorothioated" means that a structure is formed in which an oxygen atom in a phosphate group in a phosphodiester bond is substituted by a sulfur atom (a group corresponding to a phosphate group is referred to as a "phosphorothioate group"). In this specification, an oligonucleotide in which all the phosphate groups in the oligonucleotide are substituted by phosphorothioate groups is particularly referred to as an "S-oligonucleotide".

Example 3: Evaluation of Splicing Control (N-exon Skipping) Effects of Antisense Oligonucleotide in SCLC Cells With regard to ten types of antisense oligonucleotides designed in Example 2, in vitro expression of REST and sREST in human SCLC cells (STC1) was examined through RT-PCR, and the sREST/REST expression ratio was obtained. It was determined that the lower the sREST/REST expression ratio was, the more N-exon skipping had occurred, and splicing control (N-exon skipping) effects of these antisense oligonucleotides were evaluated.

Twenty four hours after introduction of a test oligonucleotide (1.0 nmol) into STC1 cells ($1.0\times10^6$ cells) through electroporation, the cells were collected and analyzed according to standard methods. Sterile water was used as a control (mock).

The results are shown in FIG. 1. Splice-switching oligonucleotides (SSOs) were further screened based on the results.

Example 4: Evaluation of Splicing Control (N-exon Skipping) Effects of Antisense Oligonucleotide in Prostate Cancer VCaP Cells SRRM4, which is abnormally expressed in SCLC cells, is also expressed in neuroendocrine prostate cancer (NEPC). In view of this, in order to further expand indications, prostate cancer cell line (VCaP) in which SRRM4 expression had been confirmed was evaluated.

After VCaP cells ($1.0\times10^6$ cells) were cultured for 24 hours, a test oligonucleotide was introduced into the cells through a lipofection method. When 48 hours passed, the cells were collected and analyzed according to standard methods. The sREST/REST expression ratio was obtained in the same manner as in Example 3, and splicing control (N-exon skipping) effects of the antisense oligonucleotides were evaluated.

The results are shown in FIG. 2. With oligonucleotides AmNA[+1/+18], AmNA[+5/+22], AmNA[+13/+30], AmNA[+15/+32], AmNA[+19/+36], AmNA[+23/+40], AmNA[+27/+44], AmNA[+31/+48], and AmNA[+35/+2 (3')], for example, the sREST/REST expression ratios were lower than 1, and N-exon skipping effects were confirmed.

In this example, splicing control (N-exon skipping) effects of the oligonucleotides were confirmed not only in SCLC cells but also in VCaP cells. The antisense oligonucleotides with confirmed splicing control effects are referred to as splice-switching oligonucleotides (SSOs).

Example 5: Evaluation of REST Splicing Control of Splice-Switching Oligonucleotide (SSO) in SCLC Cells and Cell Viability An SSO (AmNA [+31/+48]) (0.1, 1.0, 2.0 nmol) and control AmNA_26 were introduced into H146 cells ($1.0\times10^6$ cells) through electroporation, and cells were collected after 96 hours. RNA was extracted, RT-PCR was performed using primers for β-actin and REST, and REST and sREST were analyzed through polyacrylamide gel electrophoresis.

First, with REST splicing, for the H146 cells ($1.0\times10^6$ cells), the control AmNA_26 (0.1, 1.0 nmol) did not change the REST band, but AmNA_[+31/+48] reduced sREST and increased the REST band intensity (FIG. 3A).

Also, the cell viability did not change with the increase in the dose of the control AmNA_26 (0.1, 1.0 nmol) to the H146 cells ($1.0'10^6$ cells), but the cell viability decreased to 78.2% with AmNA_[+31/+48] (2.0 nmol) (FIG. 3B).

Example 6: Evaluation of Concentration Dependence of REST Splicing Control of Splice-Switching Oligonucleotide (SSO)

Twelve types of antisense oligonucleotides were added to prostate cancer cells (VCaP) at various concentrations, the expressions of REST and sREST in vitro were examined through RT-PCR, the sREST/REST expression ratios were obtained, and splicing control (N-exon skipping) effects of the antisense oligonucleotides were evaluated.

A test oligonucleotide (2.5 nM, 5 nM, 10 nM) was introduced into VCaP cells ($1.0\times10^6$ cells) through electroporation, and the cells were collected after 72 hours and analyzed according to standard methods. Sterile water was used as a control (mock).

The results are shown in FIG. 4. Based on the results, it was found that the N-exon skipping facilitating effect of the SSOs exhibited concentration dependence.

Example 7: Evaluation 2 of Concentration Dependence of REST Splicing Control of Splice-Switching Oligonucleotide (SSO)

The same experiment as in Example 6 was performed with a different number of cells seeded and a different SSO introducing method. Twelve types of antisense oligonucleotides were added to prostate cancer cells (VCaP) at various concentrations, the expressions of REST and sREST in vitro were examined through RT-PCR, "%exclusion" was obtained, and splicing control (N-exon skipping) effects of the antisense oligonucleotides were evaluated. The "%exclusion" refers to the ratio of the REST band intensity to the "sum of the REST band intensity and the sREST band intensity" of the oligonucleotide.

A test oligonucleotide (2.5 nM, 5 nM, 10 nM) was introduced into VCaP cells ($1.0\times10^5$ cells) through a lipofection method, and the cells were collected after 48 hours and analyzed according to standard methods. Sterile water was used as a control (mock).

The results are shown in FIG. 5. Based on the results, it was found that the N-exon skipping facilitating effect of the SSOs exhibited concentration dependence even when the number of cells seeded was 1/10. The N-exon skipping facilitating effect was expressed by "relative exon skipping activity" calculated by dividing "%exclusion" of an oligonucleotide by "%exclusion" of the control (no SSO was added).

Example 8: Evaluation of Concentration Dependence of REST Splicing Control of Splice-Switching Oligonucleotides (AmNA[+23/+40] and AmNA[+27/ 44])

With regard to AmNA[+23/+40] and AmNA[+27/+44] having high relative exon skipping activity revealed in Example 7, splicing control effects were examined with more varying concentrations. The above SSOs were added to prostate cancer cells (VCaP) at various concentrations, the expressions of REST and sREST in vitro were examined through RT-PCR, "%exclusion" was obtained, and splicing control (N-exon skipping) effects were evaluated.

A test oligonucleotide (0.1 nM, 0.2 nM, 0.5 nM, 1 nM, 2 nM, 5 nM, 10 nM) was introduced into VCaP cells ($1.0\times10^5$ cells) through a lipofection method, and the cells were collected after 48 hours and analyzed according to standard methods. Sterile water was used as a control (mock).

The results are shown in FIG. 6. Based on the results, it was found that the N-exon skipping facilitating effect of AmNA[+23/+40] and AmNA[+27/+44] exhibited concentration dependence, and AmNA[+23/+40] and AmNA[+27/+44] were effective even at concentrations as low as 0.1 nM. The N-exon skipping facilitating effect was expressed by "relative exon skipping activity" calculated by dividing "%exclusion" of an oligonucleotide by "%exclusion" of the control (no SSO was added).

Example 9: EC50 Analysis of Splice-Switching Oligonucleotides (AmNA[+23/+40] and AmNA[+27/+44])

EC50 (50% effective concentration) of AmNA[+23/+40] (AmNA_2340) and AmNA[+27/+44] (AmNA_2744) having high relative exon skipping activity revealed in Example 7 was analyzed. The above SSOs were added to prostate cancer cells (VCaP) at various concentrations, the expressions of REST and sREST in vitro were examined through RT-PCR, "%exclusion" was obtained, and splicing control (N-exon skipping) effects were evaluated.

A test oligonucleotide (0.1 nM, 0.2 nM, 0.5 nM, 1 nM, 2 nM, 5 nM, 10 nM) was introduced into VCaP cells ($1.0\times10^5$ cells) through a lipofection method, and the cells were collected after 48 hours and analyzed according to standard methods. The "relative exon skipping activity" was calculated at the above concentrations and plotted on a graph, and curve regression was performed.

The results are shown in FIG. 7. Based on the results, EC50 values of AmNA[+23/+40] and AmNA[+27/ 44] were 1 nM or less, and thus it is expected that these SSOs are effective at low concentrations.

Example 10: Optimization Studies of Splice-Switching Oligonucleotides (SSOs)

The sequence length was changed, the positions of AmNAs and natural nucleic acids were switched, and/or the number of AmNAs introduced was changed based on AmNA[+23/+40] (AmNA_2340) and AmNA[+27/+44] (AmNA_2744) with high relative exon skipping activity revealed in Example 7, and thus optimization of SSOs was examined. The overview of the sequence lengths and the like of the examined SSOs are shown in FIG. 8. The negative control SSOs were also examined. Four scrambled sequences (Table 1) were designed without changing ATGC ratio and artificial nucleic acid introduction percentage (for each base) of AmNA[+35/−2], each test oligonucleotide (10 nM) was introduced into VCaP cells ($1.0\times10^5$ cells) through a lipofection method, and the cells were collected after 48 hours and analyzed according to standard methods. Sterile water was used as a control (mock). The results are shown in FIG. 9. In particular, NC3 having the same activity as NT and mock (i.e., %exclusion was close to 1) was selected.

TABLE 1

| Name | Sequence (5'→3') | SEQ ID No. |
|---|---|---|
| NC1 | 5(Y)^a^5(Y)^c^T(Y)^a^T(Y)^c^G(Y) ^t^A(Y)^a^A(Y)^c^A(Y)^c^T(Y)^c | 64 |
| NC2 | 5(Y)^c^A(Y)^c^5(Y)^t^A(Y)^g^5(Y) ^a^A(Y)^t^A(Y)^t^5(Y)^a^5(Y)^t | 65 |
| NC3 | 5(Y)^g^5(Y)^c^A(Y)^c^A(Y)^a^5(Y) ^t^A(Y)^t^5(Y)^a^5(Y)^t^A(Y)^t | 66 |
| NC4 | 5(Y)^a^5(Y)^g^A(Y)^a^A(Y)^t^5(Y) ^t^A(Y)^t^5(Y)^c^5(Y)^c^A(Y)^t | 67 |

In the above sequences, a lowercase letter indicates DNA, and N(Y) indicates AmNA, 5(Y) indicates AmNA_mC, and ^ indicates being phosphorothioated (PS backbone).

The above SSOs were added to prostate cancer cells (VCaP) at a concentration of 1.0 nM, the expressions of REST and sREST in vitro were examined through RT-PCR, "%exclusion" was obtained, and splicing control (N-exon skipping) effects were evaluated. Sterile water was used as a control (mock), and NC3 was used as a control (NC).

The results are shown in FIGS. 10 and 11. The results indicate that most of the SSOs used in this example exhibited relative exon skipping activity at a concentration of 1.0 nM, and that SSOs (AmNA[+23/+42] (AmNA_2342), AmNA[+21/+40] (AmNA 2140), AmNA[+23/+44] (AmNA_2344), and AmNA[+26/+43] (AmNA_2643)) exhibiting higher relative exon skipping activity than AmNA_2340 and AmNA_2744 were obtained. The results of this example are summarized in FIG. 12.

Example 11: Evaluation of REST Splicing Control of Splice-Switching Oligonucleotide (SSO) in 22Rv1 Cells Whether or not AmNA[+23/+40] (AmNA_2340), AmNA [+27/ 44] (AmNA_2744), and AmNA[+21/+40] (AmNA_2140) and AmNA[+23/+44] (AmNA_2344) that had splicing control effects verified in Example 10 had similar splicing control effects even in different cell types was examined. The cells used in this example were 22Rv1 cells, and the cells were a human prostate cancer epithelial cell line originating from xenografts grown continuously in mice. The above SSOs were added to prostate cancer cells (22Rv1) at a concentration of 1.0 nM, the expressions of REST and sREST in vitro were examined through RT-PCR, "%exclusion" was obtained, and splicing control (N-exon skipping) effects were evaluated.

A test oligonucleotide (1.0 nM) was introduced into 22Rv1 cells ($1.0\times10^5$ cells) through a lipofection method, and the cells were collected after 48 hours and analyzed according to standard methods. Sterile water was used as a control (mock), and NC3 was used as a control (NC).

The results are shown in FIG. 13. The results indicate that AmNA_2340, AmNA_2744, AmNA_2140, and AmNA_2344 also had high relative exon skipping activity in 22Rv1 cells.

Example 12: Examination of Influence of Splice-Switching Oligonucleotides (SSOs) on SRRM4 Gene Expression Whether or not administration of AmNA_2340, AmNA_2744, AmNA_2140, and AmNA_2344 to cells affected the SRRM4 gene expression was examined. The SRRM4 gene has an RE1 sequence whose expression is controlled by REST, and high expression of REST suppresses the SRRM4 gene expression. Further, SRRM4 protein is a protein that controls REST pre-mRNA splicing, and it is known that sREST is highly expressed in SCLC cells by SRRM4 protein (FIG. 15).

A test oligonucleotide (1.0 nM) was introduced into 22Rv1 cells ($1.0\times10^5$ cells) through a lipofection method, the cells were collected after 48 hours, and a relative SRRM4 mRNA expression level was measured compared to a control (no SSO was added) through RT-PCR. Sterile water was used as a control (mock), and NC3 was used as a control (NC).

The results are shown in FIG. 14. The results indicate that an SSO having splicing control (N-exon skipping) effects may suppress the expression of SRRM4 mRNA (AmNA_2140 reduced the amount of mRNAby approximately 30%).

Example 13: Evaluation of Anti-tumor Effect In Vivo

Whether AmNA_2140 having high splicing effects and an SRRM4 mRNA expression suppression effect in Example 12 exhibited anti-tumor effects in vivo was examined. Physiological saline was used as a control. Body weight (g), the long diameter (mm) and the short diameter (mm) of tumor, and tumor size (volume) ($mm^3$) were measured on days 3, 6, 9, and 12 after transplantation of tumor cells into mice (day 0). The tumor size was calculated by dividing the long diameter×the short diameter$^2$ by 2. The results are shown in FIG. 16 and Table 2. n=1 holds true for each group.

TABLE 2

| N417-Luc | | | | | | |
|---|---|---|---|---|---|---|
| Date | Elapsed Time | Group | Body weight [g] | Long Diameter [mm] | Short Diameter [mm] | Volume [$mm^3$] |
| 2022 Jan. 17 | 0 day | SSO | 23 | Administration of Tumor Cells | | |
| | | control | 24 | | | |
| 2022 Jan. 28 | 11 day | SSO | 24 | 5 | 5 | 62.5 |
| | | control | 23 | 7 | 5 | 87.5 |
| 2022 Jan. 31 | 14 day | SSO | 24 | 6 | 5.5 | 90.75 |
| | | control | 23 | 8 | 5.5 | 121 |
| 2022 Feb. 3 | 17 day | SSO | 24 | 6 | 6 | 108 |
| | | control | 23 | 9 | 6 | 162 |
| 2022 Feb. 6 | 20 day | SSO | 25 | 6 | 5.5 | 90.75 |
| | | control | 23 | 10 | 8 | 320 |
| 2022 Feb. 9 | 23 day | SSO | 24 | 5.5 | 5.5 | 83.1875 |
| | | control | 23 | 11 | 9 | 445.5 |

FIG. 16 and Table 2 showed that AmNA_2140 exhibited anti-tumor effects in vivo.

Procedures used in this example will be described below.

Cell Culture

Cell lines were purchased from American Type Culture Collection (ATCC). SCLC cells (H146, H209) were cultured as floating cells, and prostate cancer cells (VCaP, 22Rv1) were cultured as adherent cells. A culture medium was prepared by adding FBS (Gibco™ fetal bovine serum, qualified, Brazil: Ref 10270106: LOT 42F0288K) to RPMI-1640 (4,500 mg/l glucose, L-glutamine, phenol red, HEPES, sodium pyruvate were contained: Ref 187-02705: LOT ESH7003) to 10%. Conditions inside an incubator were set to 37° C. and 5%$CO_2$. The used cell lines are as follows. SCLC cell lines: H146 (HTB-173) and H209 (HTB-172), and prostate cancer cell lines: VCaP (CRL-2876) and 22Rv1 (CRL-2505).

Transfection

Transfection of ASO into SCLC Cells:

SCLC cells ($0.5\times10^6$ cells) were transfected using Neon (registered trademark) Transfection System (manufactured by Thermo Fisher Scientific) in accordance with accompanying documents. As a result of optimizing electroporation parameters, a pulse voltage of 1200 V, a pulse width of 20 ms, and a number of pulses of 2 pulses were selected.

Transfection of ASO into Prostate Cancer Cells:

In SRRM4 expression analysis through qRT-PCR, $0.5\times10^6$ cells were seeded on a 6-well plate provided with 1750 μl of RPMI-1640 24 hours before the transfection. To each well, 250 μl of a mixture of SRRM4-ASO and Lipofectamine™ 3000 Reagent (manufactured by Thermo Fisher Scientific) prepared according to accompanying documents except that the amount of Lipofectamine™ 3000 added was 7.5 μl/well. Twenty four hours before the transfection, $0.1\times10^6$ cells were seeded on a 24-well plate with 450 μl of RPMI-1640. To each well, 50 μl of a mixture of Lipofectamine™ 3000 (manufactured by Thermo Fisher Scientific) prepared according to accompanying documents except that the amount of Lipofectamine™ 3000 added was 1.5 μl/well. In the evaluation of cell viability, twenty four hours before the transfection, $5.0\times10^4$ cells were seeded on a 96-well plate with 100 μl of RPMI-1640. To each well, 10 μl of a mixture of SRRM4-ASO and Lipofectamine™ 3000 (manufactured by Thermo Fisher Scientific) prepared according to instructions of the manufacturer except that the amount of Lipofectamine™ 3000 added was 0.3 μl/well.

Total RNA Extraction and cDNA Synthesis

RNeasy Plus Micro Kit (Qiagen) was used to extract Total RNA, following a procedure according to accompanying documents. Total RNA was quantified spectrophotometrically at 260 nm and adjusted to 100 ng/16 μl using RNase-free water, and a reverse transcription reaction (42° C., 60 minutes) was carried out by adding 4 μl of SuperScript VILO (manufactured by Thermo Fischer Scientific).

mRNA Expression Analysis through RT-qPCR

Quantitative PCR was performed using StepOnePlus™ Real-Time PCR Systems (Thermo Fisher Scientific). A master mix was prepared using TaqMan™ Fast Advanced Master Mix (manufactured by Thermo Fisher Scientific).

With regard to SRRM4, a 20-μl reaction solution was prepared such that the amount of each primer was 10 pmol. β-actin was prepared according to the accompanying documents of TaqMan™ β-Actin Detection Reagents (manufactured by Thermo Fisher Scientific). 1/100 of the cDNA obtained through the reverse transcription reaction was analyzed through RT-qPCR. The reaction was carried out under the reaction conditions as follows: 40 cycles of 20 seconds at 95° C., 3 seconds at 95° C., and 30 seconds at 60° C. Relative mRNA levels were corrected with 13-actine and analyzed using the −ΔΔCt method based on ΔCt values. All experiments were performed at least three times, and the mean±SD was calculated. Statistical significance was calculated through t-test. PCR products were subjected to agarose gel electrophoresis and sequence analysis:

```
hSRRM4 For.Primer:
                                    (SEQ ID No. 30)
5'-tgacaaagacttgacacccc-3';

hSRRM4 Rev.Primer:
                                    (SEQ ID No. 31)
5'-acctgcgtcgcttgtgttt-3';

TaqMan Probe:
                                    (SEQ ID No.32)
5'-FAM-aggtcctcatcctatagcccatcgcct-TAMRA-3'
```

mRNA Expression Analysis through RT-PCR

1/10 of the cDNA obtained through the RT reaction was amplified using Hot Start Taq DNA polymerase (manufactured by New England Biolabs). The reaction was carried out under the reaction conditions as follows: 20 cycles of 30 seconds at 95° C., 15 seconds at 95° C., 15 seconds at 58° C., and 30 seconds at 68° C. for β-actin, and 35 cycles thereof and 2 minutes at 68° C. for REST and sREST. A 25 -μl reaction solution was prepared such that the amount of each primer was 5 pmol. PCR products were subjected to electrophoresis using 5%Mini-PROTEAN TBE Precast Gels (BIO RAD). 10×Tris-Borate-EDTA Buffer (manufactured by Nacalai Tesque, Inc.) was diluted to 0.5 times and used as a running buffer.

Mini-PROTEAN Tetra System (BIO RAD) was used as an electrophoresis device. The I Bright FL1500 Imaging System was used for imaging the gel and quantifying bands. A value representing the brightness of a band per unit area was quantified from the image using the function of the I Bright FL1500 Imaging System, and the REST value relative to the sum of the sREST and REST values was used as an evaluation index. This value is shown in FIG. 3B as %exclusion. Also, the primer sequences were as follows:

REST For.Primer: 5'-gaacgcccatataaatgtgaa-3' (SEQ ID No. 33);

REST Rev.Primer: 5'-tttgaagttgcttctatctgctgt-3' (SEQ ID No. 34);

β-actin For.Primer: 5'-ggccgtcttcccctccatcg-3' (SEQ ID No. 35);

β-actin Rev.Primer: 5'-ccagttggtgacgatgccgtgc-3' (SEQ ID No. 36).

Evaluation of Cell Viability

The cell viability was evaluated using WST8 (Cell Counting Kit-8, Dojindo) according to accompanying documents. After the cells were cultured for 72 hours, a reagent was added, and absorbance at 450nm was analyzed using Infinite M1000 (Tecan). Assay was performed at least three times, and reproducibility was checked. (Gap mer Antisense Oligonucleotide)

An antisense DNA targeting SRRM4 mRNA synthesized and purified by GeneDesign, Inc. was used.

The sequence is shown in Table 3 below:

TABLE 3

| |
|---|
| 5'-TGAACAAAATAATAC-3'<br>(AmNA_26) (SEQ ID No. 37) |

The underlined bases indicate AmNA. All linkages between bases are PS bonds.

EC50 Analysis

The data obtained in Example 9 was introduced into graphing software GraphPad Prism, curve regression was performed by 4 Parameter Logistic (4PL), and EC50 was calculated.

Evaluation of Anti-tumor Effects In Vivo hSCLC cells (N417, 1×10$^6$ cells) were subcutaneously transplanted into the back of a seven-week-old BALB/c Slc-nu/nu nude mouse (male) to form a tumor. The SSO (AmNA_2140) was administrated intraperitoneally to the mouse 11 days after the transplantation. Intraperitoneal administration (10 mg/kg) was performed every three days four times in total. Physiological saline was administrated as a control. The tumor size of the mouse was observed up to 12 days after the administration of the SSO. Temporal changes in the obtained tumor size were graphed, and compared to an increase in the tumor size in the saline-administrated control group, the effect of suppressing an increase in the tumor size in the SSO administrated group was confirmed.

INDUSTRIAL APPLICABILITY

The present invention is useful for manufacturing medicines for treatment of cancer.

This application is based on JP 2021-29327 (filing date: Feb. 25, 2021) filed in Japan, the contents of which are fully incorporated herein.

The invention claimed is:

1. An oligonucleotide or a pharmacologically acceptable salt thereof comprising a nucleotide sequence complementary to a continuous sequence of at least 12 bases in a target region consisting of a base sequence of SEQ ID No. 1;

wherein the oligonucleotide or pharmacologically acceptable salt thereof induces N-exon skipping in human RE1-silencing transcription factor (REST) pre-mRNA processing, and wherein the oligonucleotide has a length of 12 to 35 bases.

2. The oligonucleotide or pharmacologically acceptable salt thereof according to claim 1, wherein the oligonucleotide or pharmacologically acceptable salt thereof has at least one nucleoside structure represented by a formula (I) below:

[Chemical Formula 1]

(I)

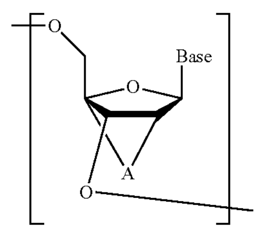

where in the formula (I),

Base represents a purin-9-yl group that may have any one or more substituents selected from an a group, or a 2-oxo-1,2-dihydropyrimidin-1-yl group that may have any one or more substituents selected from the a group, the α group consisting of a hydroxy group, a hydroxy group protected by a protecting group for nucleic acid synthesis, linear alkyl groups having 1 to 6 carbon atoms, linear alkoxy groups having 1 to 6 carbon atoms, a mercapto group, a mercapto group protected by a protecting group for nucleic acid synthesis, linear alkylthio groups having 1 to 6 carbon atoms, an amino group, linear alkylamino groups having 1 to 6 carbon atoms, an amino group protected by a protecting group for nucleic acid synthesis, and halogen atoms, A represents a divalent group represented by the following formulae:

[Chemical Formula 2]

(a-1)

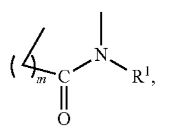

(a-2)

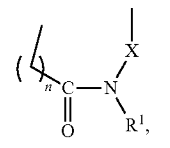

(b-1)

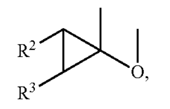

(c-1)

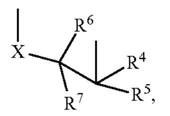

(c-2)

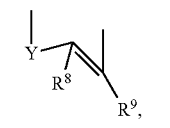

(d-1)

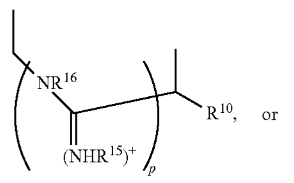

or (e-1)

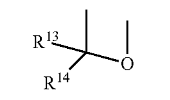

$R^1$ represents a hydrogen atom, an alkyl group having 1 to 7 carbon atoms that may form a branch or a ring, an alkenyl group having 2 to 7 carbon atoms that may form a branch or a ring, an aryl group having 3 to 12 carbon atoms that may have any one or more substituents selected from the a group and may have a heteroatom, an aralkyl group with an aryl moiety having 3 to 12 carbon atoms that may have any one or more substituents selected from the a group and may have a heteroatom, or an amino group protecting group for nucleic acid synthesis;

$R^2$ and $R^3$ each independently represent a hydrogen atom; an alkyl group having 1 to 7 carbon atoms that may form a branch or a ring and may have undergone substitution by an aryl group having 3 to 12 carbon atoms that may have a heteroatom; or an aralkyl group with an aryl moiety having 3 to 12 carbon atoms that may have a heteroatom; or $R^2$ and $R^3$ together represent $—(CH_2)_q—$, where q is an integer of 2 to 5;

$R^4$ and $R^5$ each independently represent one selected from the group consisting of a hydrogen atom; a hydroxy group; an alkyl group having 1 to 7 carbon atoms that may form a branch or a ring; an alkoxy group having 1 to 7 carbon atoms that may form a branch or a ring; an amino group; and an amino group protected by a protecting group for nucleic acid synthesis, alternatively, $R^4$ and $R^5$ together represent $=C(R^{11})\,R^{12}$, where $R^{11}$ and $R^{12}$ each independently represent a hydrogen atom, a hydroxy group, a hydroxy group protected by a protecting group for nucleic acid synthesis, a mercapto group, a mercapto group protected by a protecting group for nucleic acid synthesis, an amino group, a linear or branched alkoxy group having 1 to 6 carbon atoms, a linear or branched alkylthio group having 1 to 6 carbon atoms, a cyanoalkoxy group having 1 to 6 carbon atoms, or a linear or branched alkylamino group having 1 to 6 carbon atoms;

$R^6$ and $R^7$ each independently represent a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^8$ represents a hydrogen atom, an alkyl group having 1 to 7 carbon atoms that may form a branch or a ring, an alkoxy group having 1 to 7 carbon atoms that may form a branch or a ring, or a linear or branched alkylthio group having 1 to 6 carbon atoms;

$R^9$ represents a hydrogen atom, a hydroxy group, an alkyl group having 1 to 7 carbon atoms that may form a branch or a ring, an alkoxy group having 1 to 7 carbon atoms that may form a branch or a ring, an amino group, or an amino group protected by a protecting group for nucleic acid synthesis;

$R^{10}$ represents a hydrogen atom, an alkyl group having 1 to 7 carbon atoms that may form a branch or a ring, an amino group protecting group, or the following,

[Chemical Formula 3]

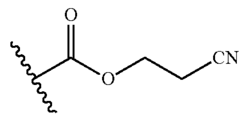

or, $—(C{=}(NHR^{17})^+)—NR^{18}R^{19}$, where $R^{17}$, $R^{18}$, and $R^{19}$ each independently represent a hydrogen atom, an alkyl group having 1 to 7 carbon atoms that may form a branch or a ring, an amino group protecting group, or the following;

[Chemical Formula 4]

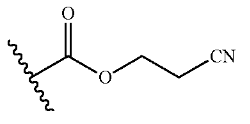

$R^{13}$ and $R^{14}$ each independently represent one selected from the group consisting of a hydrogen atom; a hydroxy group; an alkyl group having 1 to 7 carbon atoms that may form a branch or a ring; an alkoxy group having 1 to 7 carbon atoms that may form a branch or a ring; an amino group; and an amino group protected by a protecting group for nucleic acid synthesis;

m is an integer of 0 to 2;

n is an integer of 0 to 1;

when $R^{10}$ represents a hydrogen atom, an alkyl group having 1 to 7 carbon atoms that may form a branch or a ring, an amino group protecting group, or the following,

[Chemical Formula 5]

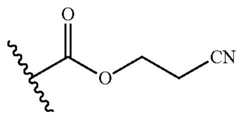

p is 1, and $R^{15}$ and $R^{16}$ each independently represent a hydrogen atom, an alkyl group having 1 to 7 carbon atoms that may form a branch or a ring, an amino group protecting group, or the following,

[Chemical Formula 6]

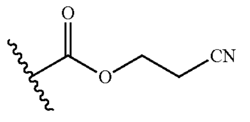

or, when $R^{10}$ represents —(C=(NHR$^{17}$)+)—NR$^{18}$R$^{19}$, p is 0;

X is an oxygen atom, a sulfur atom, or an amino group; and

Y is an oxygen atom or a sulfur atom.

3. The oligonucleotide or pharmacologically acceptable salt thereof according to claim 1, wherein a bond between nucleotides that constitute the oligonucleotide contains a phosphorothioate.

4. The oligonucleotide or pharmacologically acceptable salt thereof according to claim 1, wherein the base sequence of the oligonucleotide includes any of the base sequences of SEQ ID Nos. 3 to 11 and SEQ ID Nos. 40 to 49.

5. The oligonucleotide or pharmacologically acceptable salt thereof according to claim 2, wherein the nucleoside structure represented by the formula (I) is represented by

[Chemical Formula 7]

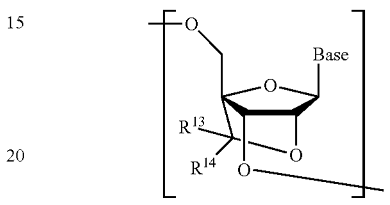

where both $R^{13}$ and $R^{14}$ are hydrogen atoms; or

[Chemical Formula 8]

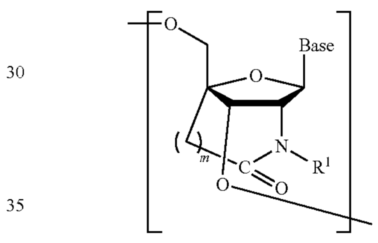

where m is 0, and $R^1$ represents a hydrogen atom, a methyl group, an ethyl group, an n-propyl group, an isopropyl group, a phenyl group, or a benzyl group.

6. A pharmaceutical composition comprising the oligonucleotide or pharmacologically acceptable salt thereof according to claim 1.

7. The pharmaceutical composition according to claim 6, wherein the pharmaceutical composition is a cancer therapeutic agent.

8. The pharmaceutical composition according to claim 7, for use in treatment of at least one cancer selected from the group consisting of small cell lung cancer, prostate cancer, and breast cancer.

9. The pharmaceutical composition according to claim 6, wherein the pharmaceutical composition is a heart failure therapeutic agent.

* * * * *

SEQUENCE LISTING

<160> NUMBER OF SEQ ID NOS: 67

<210> SEQ ID NO 1
<211> LENGTH: 50
<212> TYPE: RNA
<213> ORGANISM: Homo sapiens

<400> SEQUENCE: 1 uggggguaugg auaccauuug guaauauuua cuagagugug aucuagaugg 50

<210> SEQ ID NO 2
<211> LENGTH: 138
<212> TYPE: RNA
<213> ORGANISM: Homo sapiens

<400> SEQUENCE: 2
uuuucauaaa ugucaauuuc cguuuuucua cuaugcauuc cauuggacca gugggguaug 60
gauaccauuu gguaauauuu acuagagugu gaucuagaug gguauguauu cagguagaau 120
guauuacucu uaugccuu 138

<210> SEQ ID NO 3
<211> LENGTH: 18
<212> TYPE: DNA
<213> ORGANISM: Artificial Sequence
<220> FEATURE:
<223> OTHER INFORMATION: [+1/+18]

<400> SEQUENCE: 3
aatggtatcc ataccccca 18

<210> SEQ ID NO 4
<211> LENGTH: 18
<212> TYPE: DNA
<213> ORGANISM: Artificial Sequence
<220> FEATURE:
<223> OTHER INFORMATION: [+5/+22]

<400> SEQUENCE: 4
accaaatggt atccatac 18

<210> SEQ ID NO 5
<211> LENGTH: 18
<212> TYPE: DNA
<213> ORGANISM: Artificial Sequence
<220> FEATURE:
<223> OTHER INFORMATION: [+13/+30]

<400> SEQUENCE: 5
taaatattac caaatggt 18

<210> SEQ ID NO 6
<211> LENGTH: 18
<212> TYPE: DNA
<213> ORGANISM: Artificial Sequence
<220> FEATURE:
<223> OTHER INFORMATION: [+15/+32]

<400> SEQUENCE: 6
agtaaatatt accaaatg 18

<210> SEQ ID NO 7
<211> LENGTH: 18
<212> TYPE: DNA
<213> ORGANISM: Artificial Sequence
<220> FEATURE:
<223> OTHER INFORMATION: [+19/+36]

<400> SEQUENCE: 7
ctctagtaaa tattacca 18

<210> SEQ ID NO 8

<211> LENGTH: 18
<212> TYPE: DNA
<213> ORGANISM: Artificial Sequence
<220> FEATURE:
<223> OTHER INFORMATION: [+23/+40]

<400> SEQUENCE: 8
cacactctag taaatatt 18

<210> SEQ ID NO 9
<211> LENGTH: 18
<212> TYPE: DNA
<213> ORGANISM: Artificial Sequence
<220> FEATURE:
<223> OTHER INFORMATION: [+27/+44]

<400> SEQUENCE: 9
agatcacact ctagtaaa 18

<210> SEQ ID NO 10
<211> LENGTH: 18
<212> TYPE: DNA
<213> ORGANISM: Artificial Sequence
<220> FEATURE:
<223> OTHER INFORMATION: [+31/+48]

<400> SEQUENCE: 10
atctagatca cactctag 18

<210> SEQ ID NO 11
<211> LENGTH: 18
<212> TYPE: DNA
<213> ORGANISM: Artificial Sequence
<220> FEATURE:
<223> OTHER INFORMATION: [+35/-2(3')]

<400> SEQUENCE: 11
acccatctag atcacact 18

<210> SEQ ID NO 12
<211> LENGTH: 18
<212> TYPE: DNA
<213> ORGANISM: Artificial Sequence
<220> FEATURE:
<223> OTHER INFORMATION: AmNA[-44/-27]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: a = AmNA_a
<220> FEATURE:
<221> NAME/KEY: modified_base
<222> LOCATION: (5)..(5)
<223> OTHER INFORMATION: g = AmNA_g
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)
<223> OTHER INFORMATION: t = AmNA_t
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: a = AmNA_a
<220> FEATURE:
<221> NAME/KEY: modified_base
<222> LOCATION: (17)..(17)
<223> OTHER INFORMATION: t = AmNA_t

<400> SEQUENCE: 12
aaacggaaat tgacattt 18

<210> SEQ ID NO 13
<211> LENGTH: 18
<212> TYPE: DNA
<213> ORGANISM: Artificial Sequence
<220> FEATURE:
<223> OTHER INFORMATION: AmNA[-32/-15]
<220> FEATURE:
<221> NAME/KEY: modified_base
<222> LOCATION: (1)..(1)
<223> OTHER INFORMATION: t = AmNA_t
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: t = AmNA_t
<220> FEATURE:
<221> NAME/KEY: modified_base
<222> LOCATION: (7)..(7)
<223> OTHER INFORMATION: g = AmNA_g
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: a = AmNA_a
<220> FEATURE:
<221> NAME/KEY: modified_base
<222> LOCATION: (17)..(17)
<223> OTHER INFORMATION: g = AmNA_g

<400> SEQUENCE: 13
tgcatagtag aaaaacgg 18

<210> SEQ ID NO 14
<211> LENGTH: 18
<212> TYPE: DNA

<213> ORGANISM: Artificial Sequence
<220> FEATURE:
<223> OTHER INFORMATION: AmNA[-24/-7]
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: a = AmNA_a
<220> FEATURE:
<221> NAME/KEY: modified_base
<222> LOCATION: (5)..(5)
<223> OTHER INFORMATION: g = AmNA_g
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: t = AmNA_t
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (13)..(13)
<223> OTHER INFORMATION: t = AmNA_t
<220> FEATURE:
<221> NAME/KEY: modified_base
<222> LOCATION: (15)..(15)
<223> OTHER INFORMATION: g = AmNA_g
<220> FEATURE:
<221> NAME/KEY: modified_base
<222> LOCATION: (17)..(17)
<223> OTHER INFORMATION: a = AmNA_a

<400> SEQUENCE: 14
caatggaatg catagtag 18

<210> SEQ ID NO 15
<211> LENGTH: 18
<212> TYPE: DNA
<213> ORGANISM: Artificial Sequence
<220> FEATURE:
<223> OTHER INFORMATION: AmNA[-20/-3]
<220> FEATURE:
<221> NAME/KEY: modified_base
<222> LOCATION: (1)..(1)
<223> OTHER INFORMATION: g = AmNA_g
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: t = AmNA_t
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: g = AmNA_g
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: t = AmNA_t
<220> FEATURE:
<221> NAME/KEY: modified_base
<222> LOCATION: (15)..(15)
<223> OTHER INFORMATION: c = AmNA_c
<220> FEATURE:
<221> NAME/KEY: modified_base
<222> LOCATION: (17)..(17)
<223> OTHER INFORMATION: t = AmNA_t

<400> SEQUENCE: 15
ggtccaatgg aatgcata 18

<210> SEQ ID NO 16
<211> LENGTH: 18
<212> TYPE: DNA
<213> ORGANISM: Artificial Sequence
<220> FEATURE:
<223> OTHER INFORMATION: AmNA[-18/-1]
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: g = AmNA_g
<220> FEATURE:
<221> NAME/KEY: modified_base
<222> LOCATION: (5)..(5)
<223> OTHER INFORMATION: t = AmNA_t
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)

-continued

<223> OTHER INFORMATION: g = AmNA_g
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: t = AmNA_t
<220> FEATURE:
<221> NAME/KEY: modified_base
<222> LOCATION: (17)..(17)
<223> OTHER INFORMATION: c = AmNA_c
<220> FEATURE:
<221> NAME/KEY: modified_base
<222> LOCATION: (17)..(17)
<223> OTHER INFORMATION: m5c

<400> SEQUENCE: 16
ctggtccaat ggaatgca 18

<210> SEQ ID NO 17
<211> LENGTH: 18
<212> TYPE: DNA
<213> ORGANISM: Artificial Sequence
<220> FEATURE:
<223> OTHER INFORMATION: AmNA[-8/+10]
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(13)
<223> OTHER INFORMATION: g = AmNA_g
<220> FEATURE:
<221> NAME/KEY: modified_base
<222> LOCATION: (15)..(15)
<223> OTHER INFORMATION: t = AmNA_t
<220> FEATURE:
<221> NAME/KEY: modified_base
<222> LOCATION: (17)..(17)
<223> OTHER INFORMATION: c = AmNA_c
<220> FEATURE:
<221> NAME/KEY: modified_base
<222> LOCATION: (17)..(17)
<223> OTHER INFORMATION: m5c

<400> SEQUENCE: 17 ccataccccca ctggtcca 18

<210> SEQ ID NO 18
<211> LENGTH: 18
<212> TYPE: DNA
<213> ORGANISM: Artificial Sequence
<220> FEATURE:
<223> OTHER INFORMATION: AmNA[+1/+18]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: t = AmNA_t
<220> FEATURE:
<221> NAME/KEY: modified_base
<222> LOCATION: (5)..(5)
<223> OTHER INFORMATION: g = AmNA_g
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (15)..(15)
<223> OTHER INFORMATION: c = AmNA_c
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (17)..(17)
<223> OTHER INFORMATION: c = AmNA_c
<220> FEATURE:
<221> NAME/KEY: modified_base
<222> LOCATION: (17)..(17)
<223> OTHER INFORMATION: m5c

<400> SEQUENCE: 18
aatggtatcc atacccca 18

<210> SEQ ID NO 19
<211> LENGTH: 18
<212> TYPE: DNA
<213> ORGANISM: Artificial Sequence
<220> FEATURE:
<223> OTHER INFORMATION: AmNA[+5/+22]
<220> FEATURE:

<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: t = AmNA_t
<220> FEATURE:
<221> NAME/KEY: modified_base
<222> LOCATION: (9)..(9)
<223> OTHER INFORMATION: g = AmNA_g
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: c = AmNA_c
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (15)..(15)
<223> OTHER INFORMATION: a = AmNA_a
<220> FEATURE:
<221> NAME/KEY: modified_base
<222> LOCATION: (17)..(17)
<223> OTHER INFORMATION: a = AmNA_a

<400> SEQUENCE: 19
accaaatggt atccatac 18

<210> SEQ ID NO 20
<211> LENGTH: 18
<212> TYPE: DNA
<213> ORGANISM: Artificial Sequence
<220> FEATURE:
<223> OTHER INFORMATION: AmNA[+13/+30]
<220> FEATURE:
<221> NAME/KEY: modified_base
<222> LOCATION: (1)..(1)
<223> OTHER INFORMATION: t = AmNA_t
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: a = AmNA_a
<220> FEATURE:
<221> NAME/KEY: modified_base
<222> LOCATION: (5)..(5)
<223> OTHER INFORMATION: t = AmNA_t
<220> FEATURE:
<221> NAME/KEY: modified_base
<222> LOCATION: (7)..(7)
<223> OTHER INFORMATION: t = AmNA_t
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: t = AmNA_t
<220> FEATURE:
<221> NAME/KEY: modified_base
<222> LOCATION: (17)..(17)
<223> OTHER INFORMATION: g = AmNA_g

<400> SEQUENCE: 20
taaatattac caaatggt 18

<210> SEQ ID NO 21
<211> LENGTH: 18
<212> TYPE: DNA
<213> ORGANISM: Artificial Sequence
<220> FEATURE:
<223> OTHER INFORMATION: AmNA[+15/+32]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: t = AmNA_t
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: t = AmNA_t
<220> FEATURE:
<221> NAME/KEY: modified_base
<222> LOCATION: (9)..(9)
<223> OTHER INFORMATION: t = AmNA_t
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: c = AmNA_c
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (15)..(15)
<223> OTHER INFORMATION: a = AmNA_a
<220> FEATURE:
<221> NAME/KEY: modified_base
<222> LOCATION: (17)..(17)

<223> OTHER INFORMATION: t = AmNA_t

<400> SEQUENCE: 21
agtaaatatt accaaatg 18

<210> SEQ ID NO 22
<211> LENGTH: 18
<212> TYPE: DNA
<213> ORGANISM: Artificial Sequence
<220> FEATURE:
<223> OTHER INFORMATION: AmNA[+19/+36]
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: t = AmNA_t
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)
<223> OTHER INFORMATION: t = AmNA_t
<220> FEATURE:
<221> NAME/KEY: modified_base
<222> LOCATION: (13)..(13)
<223> OTHER INFORMATION: t = AmNA_t
<220> FEATURE:
<221> NAME/KEY: modified_base
<222> LOCATION: (15)..(15)
<223> OTHER INFORMATION: a = AmNA_a
<220> FEATURE:
<221> NAME/KEY: modified_base
<222> LOCATION: (17)..(17)
<223> OTHER INFORMATION: c = AmNA_c
<220> FEATURE:
<221> NAME/KEY: modified_base
<222> LOCATION: (17)..(17)
<223> OTHER INFORMATION: m5c

<400> SEQUENCE: 22
ctctagtaaa tattacca 18

<210> SEQ ID NO 23
<211> LENGTH: 18
<212> TYPE: DNA
<213> ORGANISM: Artificial Sequence
<220> FEATURE:
<223> OTHER INFORMATION: AmNA[+23/+40]
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)
<223> OTHER INFORMATION: t = AmNA_t
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: t = AmNA_t
<220> FEATURE:
<221> NAME/KEY: modified_base
<222> LOCATION: (17)..(17)
<223> OTHER INFORMATION: t = AmNA_t

<400> SEQUENCE: 23
cacactctag taaatatt 18

<210> SEQ ID NO 24
<211> LENGTH: 18
<212> TYPE: DNA
<213> ORGANISM: Artificial Sequence
<220> FEATURE:
<223> OTHER INFORMATION: AmNA[+27/+44]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: a = AmNA_a
<220> FEATURE:

<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: t = AmNA_t
<220> FEATURE:
<221> NAME/KEY: modified_base
<222> LOCATION: (17)..(17)
<223> OTHER INFORMATION: a = AmNA_a

<400> SEQUENCE: 24
agatcacact ctagtaaa 18

<210> SEQ ID NO 25
<211> LENGTH: 18
<212> TYPE: DNA
<213> ORGANISM: Artificial Sequence
<220> FEATURE:
<223> OTHER INFORMATION: AmNA[+31/+48]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(13)
<223> OTHER INFORMATION: c = AmNA_c
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (15)..(15)
<223> OTHER INFORMATION: c = AmNA_c
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (17)..(17)
<223> OTHER INFORMATION: a = AmNA_a

<400> SEQUENCE: 25
atctagatca cactctag 18

<210> SEQ ID NO 26
<211> LENGTH: 18
<212> TYPE: DNA
<213> ORGANISM: Artificial Sequence
<220> FEATURE:
<223> OTHER INFORMATION: AmNA[+35/-2(3')]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m3c
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m3c
<220> FEATURE:
<221> NAME/KEY: modified_base
<222> LOCATION: (9)..(9)

<223> OTHER INFORMATION: a = AmNA_a
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: c = AmNA_c
<220> FEATURE:
<221> NAME/KEY: modified_base
<222> LOCATION: (13)..(13)
<223> OTHER INFORMATION: m3c
<220> FEATURE:
<221> NAME/KEY: modified_base
<222> LOCATION: (15)..(15)
<223> OTHER INFORMATION: c = AmNA_c
<220> FEATURE:
<221> NAME/KEY: modified_base
<222> LOCATION: (15)..(15)
<223> OTHER INFORMATION: m3c
<220> FEATURE:
<221> NAME/KEY: modified_base
<222> LOCATION: (17)..(17)
<223> OTHER INFORMATION: c = AmNA_c

<400> SEQUENCE: 26
acccatctag atcacact 18

<210> SEQ ID NO 27
<211> LENGTH: 18
<212> TYPE: DNA
<213> ORGANISM: Artificial Sequence
<220> FEATURE:
<223> OTHER INFORMATION: AmNA[+43/-10(3')]
<220> FEATURE:
<221> NAME/KEY: modified_base
<222> LOCATION: (1)..(1)
<223> OTHER INFORMATION: g = AmNA_g
<220> FEATURE:
<221> NAME/KEY: modified_base
<222> LOCATION: (3)..(3)
<223> OTHER INFORMATION: a = AmNA_a
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: c = AmNA_c
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (17)..(17)
<223> OTHER INFORMATION: a = AmNA_a

<400> SEQUENCE: 27
gaatacatac ccatctag 18

<210> SEQ ID NO 28
<211> LENGTH: 18
<212> TYPE: DNA
<213> ORGANISM: Artificial Sequence
<220> FEATURE:
<223> OTHER INFORMATION: AmNA[-5(3')/-22(3')]
<220> FEATURE:
<221> NAME/KEY: modified_base
<222> LOCATION: (1)..(1)
<223> OTHER INFORMATION: t = AmNA_t
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: t = AmNA_t
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (17)..(17)
<223> OTHER INFORMATION: a = AmNA_a

<400> SEQUENCE: 28
tacattctac ctgaatac 18

<210> SEQ ID NO 29
<211> LENGTH: 18
<212> TYPE: DNA
<213> ORGANISM: Artificial Sequence
<220> FEATURE:
<223> OTHER INFORMATION: AmNA[-17(3')/-34(3')]
<220> FEATURE:
<221> NAME/KEY: modified_base
<222> LOCATION: (1)..(1)
<223> OTHER INFORMATION: g = AmNA_g
<220> FEATURE:
<221> NAME/KEY: modified_base
<222> LOCATION: (3)..(3)
<223> OTHER INFORMATION: a = AmNA_a
<220> FEATURE:

-continued

<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: g = AmNA_g
<220> FEATURE:
<221> NAME/KEY: modified_base
<222> LOCATION: (9)..(9)
<223> OTHER INFORMATION: g = AmNA_g
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: t = AmNA_t
<220> FEATURE:
<221> NAME/KEY: modified_base
<222> LOCATION: (15)..(15)
<223> OTHER INFORMATION: t = AmNA_t
<220> FEATURE:
<221> NAME/KEY: modified_base
<222> LOCATION: (15)..(15)
<223> OTHER INFORMATION: c = AmNA_c
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (17)..(17)
<223> OTHER INFORMATION: t = AmNA_t

<400> SEQUENCE: 29
gcataagagt aatacatt 18

<210> SEQ ID NO 30
<211> LENGTH: 21
<212> TYPE: DNA
<213> ORGANISM: Artificial Sequence
<220> FEATURE:
<223> OTHER INFORMATION: hSRRM4 For.Primer

<400> SEQUENCE: 30
tgacaaagac ttgacaccac c 21

<210> SEQ ID NO 31
<211> LENGTH: 19
<212> TYPE: DNA
<213> ORGANISM: Artificial Sequence
<220> FEATURE:
<223> OTHER INFORMATION: hSRRM4 Rev.Primer

<400> SEQUENCE: 31
acctgcgtcg cttgtgttt 19

<210> SEQ ID NO 32
<211> LENGTH: 27
<212> TYPE: DNA
<213> ORGANISM: Artificial Sequence
<220> FEATURE:
<223> OTHER INFORMATION: TaqMan Probe

<400> SEQUENCE: 32
aggtcctcat cctatagccc atcgcct 27

<210> SEQ ID NO 33
<211> LENGTH: 21

<212> TYPE: DNA
<213> ORGANISM: Artificial Sequence
<220> FEATURE:
<223> OTHER INFORMATION: REST For.Primer

<400> SEQUENCE: 33
gaacgcccat ataaatgtga a 21

<210> SEQ ID NO 34
<211> LENGTH: 24
<212> TYPE: DNA
<213> ORGANISM: Artificial Sequence
<220> FEATURE:
<223> OTHER INFORMATION: REST Rev.Primer

<400> SEQUENCE: 34
tttgaagttg cttctatctg ctgt 24

<210> SEQ ID NO 35
<211> LENGTH: 20
<212> TYPE: DNA
<213> ORGANISM: Artificial Sequence
<220> FEATURE:
<223> OTHER INFORMATION: beta-actin For.Primer

<400> SEQUENCE: 35
ggccgtcttc ccctccatcg 20

<210> SEQ ID NO 36
<211> LENGTH: 22
<212> TYPE: DNA
<213> ORGANISM: Artificial Sequence
<220> FEATURE:
<223> OTHER INFORMATION: beta-actin Rev.Primer

<400> SEQUENCE: 36
ccagttggtg acgatgccgt gc 22

<210> SEQ ID NO 37
<211> LENGTH: 15
<212> TYPE: DNA
<213> ORGANISM: Artificial Sequence
<220> FEATURE:
<223> OTHER INFORMATION: AmNA_26
<220> FEATURE:
<221> NAME/KEY: modified_base
<222> LOCATION: (1)..(3)
<223> OTHER INFORMATION: AmNA
<220> FEATURE:
<221> NAME/KEY: modified_base
<222> LOCATION: (2)..(15)
<223> OTHER INFORMATION: phosphorotioated
<220> FEATURE:
<221> NAME/KEY: modified_base
<222> LOCATION: (13)..(14)
<223> OTHER INFORMATION: AmNA

<400> SEQUENCE: 37
tgaacaaaat aatac 15

<210> SEQ ID NO 38
<211> LENGTH: 26
<212> TYPE: RNA
<213> ORGANISM: Homo sapiens

<400> SEQUENCE: 38
guaauauuua cuagagugug aucuag 26

<210> SEQ ID NO 39
<211> LENGTH: 24
<212> TYPE: RNA
<213> ORGANISM: Homo sapiens

<400> SEQUENCE: 39
guaauauuua cuagagugug aucu 24

<210> SEQ ID NO 40
<211> LENGTH: 20
<212> TYPE: DNA
<213> ORGANISM: Artificial Sequence
<220> FEATURE:
<223> OTHER INFORMATION: [+23/+42]

<400> SEQUENCE: 40
atcacactct agtaaatatt 20

<210> SEQ ID NO 41
<211> LENGTH: 20
<212> TYPE: DNA
<213> ORGANISM: Artificial Sequence
<220> FEATURE:
<223> OTHER INFORMATION: [+21/+40]

<400> SEQUENCE: 41
cacactctag taaatattac 20

<210> SEQ ID NO 42
<211> LENGTH: 16
<212> TYPE: DNA
<213> ORGANISM: Artificial Sequence
<220> FEATURE:
<223> OTHER INFORMATION: [+23/+38]

<400> SEQUENCE: 42
cactctagta aatatt 16

<210> SEQ ID NO 43
<211> LENGTH: 16
<212> TYPE: DNA
<213> ORGANISM: Artificial Sequence
<220> FEATURE:
<223> OTHER INFORMATION: [+25/+40]

<400> SEQUENCE: 43
cacactctag taaata 16

<210> SEQ ID NO 44
<211> LENGTH: 20
<212> TYPE: DNA
<213> ORGANISM: Artificial Sequence
<220> FEATURE:
<223> OTHER INFORMATION: [+27/+46]

<400> SEQUENCE: 44
ctagatcaca ctctagtaaa 20

<210> SEQ ID NO 45
<211> LENGTH: 20
<212> TYPE: DNA
<213> ORGANISM: Artificial Sequence
<220> FEATURE:
<223> OTHER INFORMATION: [+25/+44]

<400> SEQUENCE: 45
agatcacact ctagtaaata 20

<210> SEQ ID NO 46
<211> LENGTH: 16
<212> TYPE: DNA
<213> ORGANISM: Artificial Sequence
<220> FEATURE:
<223> OTHER INFORMATION: [+27/+42]

<400> SEQUENCE: 46
atcacactct agtaaa 16

<210> SEQ ID NO 47
<211> LENGTH: 16
<212> TYPE: DNA
<213> ORGANISM: Artificial Sequence
<220> FEATURE:
<223> OTHER INFORMATION: [+29/+44]

<400> SEQUENCE: 47
agatcacact ctagta 16

<210> SEQ ID NO 48
<211> LENGTH: 22
<212> TYPE: DNA
<213> ORGANISM: Artificial Sequence
<220> FEATURE:
<223> OTHER INFORMATION: [+23/+44]

<400> SEQUENCE: 48
agatcacact ctagtaaata tt 22

<210> SEQ ID NO 49
<211> LENGTH: 18
<212> TYPE: DNA
<213> ORGANISM: Artificial Sequence
<220> FEATURE:
<223> OTHER INFORMATION: [+26/+43]

<400> SEQUENCE: 49
gatcacactc tagtaaat 18

<210> SEQ ID NO 50
<211> LENGTH: 81
<212> TYPE: RNA
<213> ORGANISM: Homo sapiens

<400> SEQUENCE: 50
uucuacuaug cauuccauug gaccaguggg guauggauac cauuugguaa uauuuacuag 60
agugugaucu agaugggua g 81

<210> SEQ ID NO 51
<211> LENGTH: 135
<212> TYPE: RNA
<213> ORGANISM: Homo sapiens

<400> SEQUENCE: 51
ucauaaaugu caauuuccgu uuuucuacua ugcauuccau uggaccagug ggguauggau 60
accauuuggu aauauuuacu agagugugau cuagaugggu auguauucag guagaaugua 120
uuacucuuau gccuu 135

<210> SEQ ID NO 52

<211> LENGTH: 48
<212> TYPE: RNA
<213> ORGANISM: Homo sapiens

<400> SEQUENCE: 52
gauaccauuu gguaauauuu acuagagugu gaucuagaug gguaugua 48

<210> SEQ ID NO 53
<211> LENGTH: 20
<212> TYPE: DNA
<213> ORGANISM: Artificial Sequence
<220> FEATURE:
<223> OTHER INFORMATION: AmNA[+23/+42]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(20)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: t = AmNA_t
<220> FEATURE:
<221> NAME/KEY: modified_base
<222> LOCATION: (15)..(15)
<223> OTHER INFORMATION: a = AmNA_a
<220> FEATURE:
<221> NAME/KEY: modified_base
<222> LOCATION: (17)..(17)
<223> OTHER INFORMATION: t = AmNA_t
<220> FEATURE:
<221> NAME/KEY: modified_base
<222> LOCATION: (19)..(19)
<223> OTHER INFORMATION: t = AmNA_t

<400> SEQUENCE: 53
atcacactct agtaaatatt 20

<210> SEQ ID NO 54
<211> LENGTH: 20
<212> TYPE: DNA
<213> ORGANISM: Artificial Sequence
<220> FEATURE:
<223> OTHER INFORMATION: AmNA[+21/+40]
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(20)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)
<223> OTHER INFORMATION: t = AmNA_t
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: t = AmNA_t
<220> FEATURE:
<221> NAME/KEY: modified_base
<222> LOCATION: (17)..(17)
<223> OTHER INFORMATION: t = AmNA_t
<220> FEATURE:
<221> NAME/KEY: modified_base
<222> LOCATION: (19)..(19)
<223> OTHER INFORMATION: a = AmNA_a

<400> SEQUENCE: 54
cacactctag taaatattac 20

<210> SEQ ID NO 55
<211> LENGTH: 16
<212> TYPE: DNA
<213> ORGANISM: Artificial Sequence
<220> FEATURE:

<223> OTHER INFORMATION: AmNA[+23/+38]
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(16)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: t = AmNA_t
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: t = AmNA_t
<220> FEATURE:
<221> NAME/KEY: modified_base
<222> LOCATION: (15)..(15)
<223> OTHER INFORMATION: t = AmNA_t

<400> SEQUENCE: 55
cactctagta aatatt 16

<210> SEQ ID NO 56
<211> LENGTH: 16
<212> TYPE: DNA
<213> ORGANISM: Artificial Sequence
<220> FEATURE:
<223> OTHER INFORMATION: AmNA[+25/+40]
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(16)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: a = AmNA_a
<220> FEATURE:
<221> NAME/KEY: modified_base
<222> LOCATION: (11)..(11)
<223> OTHER INFORMATION: t = AmNA_t
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: t = AmNA_t

<400> SEQUENCE: 56
cacactctag taaata 16

<210> SEQ ID NO 57
<211> LENGTH: 20
<212> TYPE: DNA
<213> ORGANISM: Artificial Sequence
<220> FEATURE:
<223> OTHER INFORMATION: AmNA[+27/+46]
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(20)
<223> OTHER INFORMATION: phosphorotioated
<220> FEATURE:
<221> NAME/KEY: modified_base
<222> LOCATION: (3)..(3)
<223> OTHER INFORMATION: a = AmNA_a
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: c = AmNA_c
<220> FEATURE:

<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(13)
<223> OTHER INFORMATION: c = AmNA_c
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (15)..(15)
<223> OTHER INFORMATION: a = AmNA_a
<220> FEATURE:
<221> NAME/KEY: modified_base
<222> LOCATION: (17)..(17)
<223> OTHER INFORMATION: t = AmNA_t
<220> FEATURE:
<221> NAME/KEY: modified_base
<222> LOCATION: (19)..(19)
<223> OTHER INFORMATION: a = AmNA_a

<400> SEQUENCE: 57
ctagatcaca ctctagtaaa 20

<210> SEQ ID NO 58
<211> LENGTH: 20
<212> TYPE: DNA
<213> ORGANISM: Artificial Sequence
<220> FEATURE:
<223> OTHER INFORMATION: AmNA[+25/+44]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(20)
<223> OTHER INFORMATION: phosphorotioated
<220> FEATURE:
<221> NAME/KEY: modified_base
<222> LOCATION: (3)..(3)
<223> OTHER INFORMATION: a = AmNA_a
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: t = AmNA_t
<220> FEATURE:
<221> NAME/KEY: modified_base
<222> LOCATION: (17)..(17)
<223> OTHER INFORMATION: a = AmNA_a
<220> FEATURE:
<221> NAME/KEY: modified_base
<222> LOCATION: (19)..(19)
<223> OTHER INFORMATION: t = AmNA_t

<400> SEQUENCE: 58
agatcacact ctagtaaata 20

<210> SEQ ID NO 59
<211> LENGTH: 16
<212> TYPE: DNA
<213> ORGANISM: Artificial Sequence
<220> FEATURE:
<223> OTHER INFORMATION: AmNA[+27/+42]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(16)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)

<223> OTHER INFORMATION: a = AmNA_a
<220> FEATURE:
<221> NAME/KEY: modified_base
<222> LOCATION: (13)..(13)
<223> OTHER INFORMATION: t = AmNA_t
<220> FEATURE:
<221> NAME/KEY: modified_base
<222> LOCATION: (15)..(15)
<223> OTHER INFORMATION: a = AmNA_a

<400> SEQUENCE: 59
atcacactct agtaaa 16

<210> SEQ ID NO 60
<211> LENGTH: 16
<212> TYPE: DNA
<213> ORGANISM: Artificial Sequence
<220> FEATURE:
<223> OTHER INFORMATION: AmNA[+29/+44]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(16)
<223> OTHER INFORMATION: phosphorotioated
<220> FEATURE:
<221> NAME/KEY: modified_base
<222> LOCATION: (3)..(3)
<223> OTHER INFORMATION: a = AmNA_a
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: t = AmNA_t

<400> SEQUENCE: 60
agatcacact ctagta 16

<210> SEQ ID NO 61
<211> LENGTH: 22
<212> TYPE: DNA
<213> ORGANISM: Artificial Sequence
<220> FEATURE:
<223> OTHER INFORMATION: AmNA[+23/+44]
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(22)
<223> OTHER INFORMATION: phosphorotioated
<220> FEATURE:
<221> NAME/KEY: modified_base
<222> LOCATION: (3)..(3)
<223> OTHER INFORMATION: a = AmNA_a
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: c = AmNA_c
<220> FEATURE:
<221> NAME/KEY: modified_base
<222> LOCATION: (11)..(11)
<223> OTHER INFORMATION: m5c
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: t = AmNA_t
<220> FEATURE:
<221> NAME/KEY: modified_base
<222> LOCATION: (17)..(17)
<223> OTHER INFORMATION: a = AmNA_a
<220> FEATURE:
<221> NAME/KEY: modified_base
<222> LOCATION: (19)..(19)
<223> OTHER INFORMATION: t = AmNA_t
<220> FEATURE:
<221> NAME/KEY: modified_base
<222> LOCATION: (21)..(21)
<223> OTHER INFORMATION: t = AmNA_t

<400> SEQUENCE: 61
agatcacact ctagtaaata tt 22

<210> SEQ ID NO 62
<211> LENGTH: 18
<212> TYPE: DNA

<213> ORGANISM: Artificial Sequence
<220> FEATURE:
<223> OTHER INFORMATION: AmNA[+26/+43]
<220> FEATURE:
<221> NAME/KEY: modified_base
<222> LOCATION: (1)..(1)
<223> OTHER INFORMATION: g = AmNA_g
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: t = AmNA_t
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: t = AmNA_t
<220> FEATURE:
<221> NAME/KEY: modified_base
<222> LOCATION: (11)..(11)
<223> OTHER INFORMATION: t = AmNA_t
<220> FEATURE:
<221> NAME/KEY: modified_base
<222> LOCATION: (13)..(13)
<223> OTHER INFORMATION: g = AmNA_g
<220> FEATURE:
<221> NAME/KEY: modified_base
<222> LOCATION: (15)..(15)
<223> OTHER INFORMATION: a = AmNA_a
<220> FEATURE:
<221> NAME/KEY: modified_base
<222> LOCATION: (17)..(17)
<223> OTHER INFORMATION: a = AmNA_a

<400> SEQUENCE: 62
gatcacactc tagtaaat 18

<210> SEQ ID NO 63
<211> LENGTH: 18
<212> TYPE: DNA
<213> ORGANISM: Artificial Sequence
<220> FEATURE:
<223> OTHER INFORMATION: AmNA[+27/+44]_1/3
<220> FEATURE:
<221> NAME/KEY: modified_base
<222> LOCATION: (1)..(1)
<223> OTHER INFORMATION: a = AmNA_a
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (4)..(4)
<223> OTHER INFORMATION: t = AmNA_t
<220> FEATURE:
<221> NAME/KEY: modified_base
<222> LOCATION: (7)..(7)
<223> OTHER INFORMATION: c = AmNA_c
<220> FEATURE:
<221> NAME/KEY: modified_base
<222> LOCATION: (7)..(7)
<223> OTHER INFORMATION: m5c
<220> FEATURE:
<221> NAME/KEY: modified_base
<222> LOCATION: (10)..(10)
<223> OTHER INFORMATION: t = AmNA_t
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (16)..(16)
<223> OTHER INFORMATION: a = AmNA_a

<400> SEQUENCE: 63
agatcacact ctagtaaa 18

<210> SEQ ID NO 64
<211> LENGTH: 18
<212> TYPE: DNA
<213> ORGANISM: Artificial Sequence
<220> FEATURE:
<223> OTHER INFORMATION: NC1
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: t = AmNA_t
<220> FEATURE:
<221> NAME/KEY: modified_base
<222> LOCATION: (7)..(7)
<223> OTHER INFORMATION: t = AmNA_t
<220> FEATURE:
<221> NAME/KEY: modified_base
<222> LOCATION: (9)..(9)
<223> OTHER INFORMATION: g = AmNA_g
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: a = AmNA_a
<220> FEATURE:
<221> NAME/KEY: modified_base
<222> LOCATION: (17)..(17)
<223> OTHER INFORMATION: t = AmNA_t

<400> SEQUENCE: 64
cacctatcgt aaacactc 18

<210> SEQ ID NO 65
<211> LENGTH: 18
<212> TYPE: DNA
<213> ORGANISM: Artificial Sequence
<220> FEATURE:

<223> OTHER INFORMATION: NC2
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: a = AmNA_a
<220> FEATURE:
<221> NAME/KEY: modified_base
<222> LOCATION: (5)..(5)
<223> OTHER INFORMATION: c = AmNA_c
<220> FEATURE:
<221> NAME/KEY: modified_base
<222> LOCATION: (5)..(5)
<223> OTHER INFORMATION: m5c
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: a = AmNA_a
<220> FEATURE:
<221> NAME/KEY: modified_base
<222> LOCATION: (15)..(15)
<223> OTHER INFORMATION: c = AmNA_c
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (17)..(17)
<223> OTHER INFORMATION: c = AmNA_c
<220> FEATURE:
<221> NAME/KEY: modified_base
<222> LOCATION: (17)..(17)
<223> OTHER INFORMATION: m5c

<400> SEQUENCE: 65
ccacctagca atatcact 18

<210> SEQ ID NO 66
<211> LENGTH: 18
<212> TYPE: DNA
<213> ORGANISM: Artificial Sequence
<220> FEATURE:
<223> OTHER INFORMATION: NC3
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(18)
<223> OTHER INFORMATION: phosphorotioated
<220> FEATURE:
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: c = AmNA_c
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (15)..(15)
<223> OTHER INFORMATION: c = AmNA_c
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (17)..(17)
<223> OTHER INFORMATION: a = AmNA_a

<400> SEQUENCE: 66
cgccacaact atcactat 18

<210> SEQ ID NO 67
<211> LENGTH: 18
<212> TYPE: DNA
<213> ORGANISM: Artificial Sequence
<220> FEATURE:
<223> OTHER INFORMATION: NC4
<220> FEATURE:
<221> NAME/KEY: modified_base
<222> LOCATION: (1)..(1)
<223> OTHER INFORMATION: c = AmNA_c
<220> FEATURE:
<221> NAME/KEY: modified_base
<222> LOCATION: (1)..(1)
<223> OTHER INFORMATION: m5c
<220> FEATURE:
<221> NAME/KEY: modified_base
<222> LOCATION: (2)..(18)
<223> OTHER INFORMATION: phosphorotioated
<220> FEATURE:

-continued

```
<221> NAME/KEY: modified_base
<222> LOCATION: (3)..(3)
<223> OTHER INFORMATION: c = AmNA_c
<220> FEATURE:
<221> NAME/KEY: modified_base
<222> LOCATION: (3)..(3)
<223> OTHER INFORMATION: m5c
<220> FEATURE:
<221> NAME/KEY: modified_base
<222> LOCATION: (5)..(5)
<223> OTHER INFORMATION: a = AmNA_a
<220> FEATURE:
<221> NAME/KEY: modified_base
<222> LOCATION: (7)..(7)
<223> OTHER INFORMATION: a = AmNA_a
<220> FEATURE:
<221> NAME/KEY: modified_base
<222> LOCATION: (9)..(9)
<223> OTHER INFORMATION: c = AmNA_c
<220> FEATURE:
<221> NAME/KEY: modified_base
<222> LOCATION: (9)..(9)
<223> OTHER INFORMATION: m5c
<220> FEATURE:
<221> NAME/KEY: modified_base
<222> LOCATION: (11)..(11)
<223> OTHER INFORMATION: a = AmNA_a
<220> FEATURE:
<221> NAME/KEY: modified_base
<222> LOCATION: (13)..(13)
<223> OTHER INFORMATION: c = AmNA_c
<220> FEATURE:
<221> NAME/KEY: modified_base
<222> LOCATION: (13)..(13)
<223> OTHER INFORMATION: m5c
<220> FEATURE:
<221> NAME/KEY: modified_base
<222> LOCATION: (15)..(15)
<223> OTHER INFORMATION: c = AmNA_c
<220> FEATURE:
<221> NAME/KEY: modified_base
<222> LOCATION: (15)..(15)
<223> OTHER INFORMATION: m5c
<220> FEATURE:
<221> NAME/KEY: modified_base
<222> LOCATION: (17)..(17)
<223> OTHER INFORMATION: a = AmNA_a

<400> SEQUENCE: 67

cacgaaatct atccccat                                              18
```